United States Patent
Lohse et al.

(10) Patent No.: US 12,391,981 B2
(45) Date of Patent: **\*Aug. 19, 2025**

(54) CHROMOGENIC PEROXIDASE SUBSTRATES

(71) Applicant: Agilent Technologies, Inc., Santa Clara, CA (US)

(72) Inventors: Jesper Lohse, Kobenhavn NV (DK); Mike Paw Maischnack Hansen, Kobenhavn NV (DK)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/639,734

(22) Filed: Apr. 18, 2024

(65) Prior Publication Data

US 2024/0360495 A1    Oct. 31, 2024

Related U.S. Application Data

(63) Continuation of application No. 17/885,188, filed on Aug. 10, 2022, now Pat. No. 11,993,810, which is a continuation of application No. 16/688,076, filed on Nov. 19, 2019, now Pat. No. 11,466,314, which is a continuation of application No. 15/383,996, filed on Dec. 19, 2016, now Pat. No. 10,526,646.

(60) Provisional application No. 62/269,575, filed on Dec. 18, 2015.

(51) Int. Cl.
| | |
|---|---|
| C12Q 1/68 | (2018.01) |
| C07D 311/82 | (2006.01) |
| C07D 311/90 | (2006.01) |
| C07D 493/10 | (2006.01) |
| C12N 9/08 | (2006.01) |
| C12N 9/96 | (2006.01) |
| C12Q 1/28 | (2006.01) |
| C12Q 1/6841 | (2018.01) |
| G01N 33/58 | (2006.01) |

(52) U.S. Cl.
CPC .......... C12Q 1/6841 (2013.01); C07D 311/82 (2013.01); C07D 311/90 (2013.01); C07D 493/10 (2013.01); C12N 9/0065 (2013.01); C12N 9/96 (2013.01); C12Q 1/28 (2013.01); G01N 33/581 (2013.01)

(58) Field of Classification Search
CPC .. C07D 311/82; C07D 311/90; C07D 493/10; C12Q 1/28
See application file for complete search history.

(56) References Cited

U.S. PATENT DOCUMENTS

| | | | |
|---|---|---|---|
| 5,863,748 A | 1/1999 | Bobrow | |
| 10,526,646 B2 | 1/2020 | Lohse et al. | |
| 11,466,314 B2 | 10/2022 | Lohse et al. | |
| 11,993,810 B2 * | 5/2024 | Lohse | C12N 9/96 |
| 2005/0255475 A1 | 11/2005 | Kumar et al. | |
| 2010/0055761 A1 | 3/2010 | Seed et al. | |
| 2014/0038169 A1 | 2/2014 | Lohse et al. | |
| 2016/0362418 A1 | 12/2016 | Polukhtin | |

FOREIGN PATENT DOCUMENTS

| | | |
|---|---|---|
| CN | 1315938 A | 10/2001 |
| CN | 101358969 A | 2/2009 |
| CN | 101836117 A | 9/2010 |
| CN | 102325895 A | 1/2012 |
| CN | 103502218 A | 1/2014 |
| CN | 103597089 A | 2/2014 |
| CN | 104288777 A | 1/2015 |
| WO | 02055512 A1 | 7/2002 |
| WO | 2007015168 A2 | 2/2007 |
| WO | 2008133728 A2 | 11/2008 |
| WO | 2008133728 A3 | 1/2009 |
| WO | 2009036760 A2 | 3/2009 |
| WO | 2009036760 A3 | 7/2009 |
| WO | 2010094283 A1 | 8/2010 |
| WO | 2010094284 A1 | 8/2010 |
| WO | 2011047680 A1 | 4/2011 |
| WO | 2012062318 A1 | 5/2012 |
| WO | 2012143010 A1 | 10/2012 |

OTHER PUBLICATIONS

Abcam, et al., "Immunohistochemistry Application Guide," Abcam, Apr. 22, 2016, 48 pages.
Afonso, Carlos A. et al., "An Expedient Synthesis of Cationic Rhodamine Fluorescent Probes Suitable for Conjugation to Amino Acids and Peptides," Synthesis, vol. 17, Nov. 21, 2003, 2647-2654.
Beija, Mariana et al., "Synthesis and Applications of Rhodamine Derivatives as Fluorescent Probes," Chem. Soc. Rev., vol. 38, 2009, 2410-2433.
Chen, Xi et al., "An Efficient and Versatile Approach for the Preparation of a Rhodamine B Ester Bioprobe Library," Dyes and Pigments, vol. 94, 2012, 296-303.
Dako, et al., "Immunohistochemical Staining Methods," Dako IHC Guidebook, 6th Ed, 2013, 218 pages.
Fanyong, Yan et al., "Synthesis and Applications of Rhodamine Fluorescent Dyes," Progress in Chemistry, vol. 18, No. 2/3, Mar. 24, 2006 , 252-261.
Huang, Chusen et al., "Versatile Probes for the Selective Detection of Vicinal-Dithiol-Containing proteins: Design, Synthesis, and Application in Living Cells," Chem. Eur. J., vol. 19, 2013, 7739-7747.
Loos, Chris V. et al., "User Protocol: Practical Guide to Multiple Staining," Cambridge Research & Instrumentation, Inc., 2009, 16 pages.

(Continued)

Primary Examiner — Jezia Riley

(57) ABSTRACT

Chromogenic conjugates for color-based detection of targets are described. The conjugates comprise a chromogenic moiety such as a rhodamine, rhodol or fluorescein. The chromogenic moiety is linked to a peroxidase substrate. The chromogenic conjugates can be used in immunohistochemical analysis and in situ hybridization. The conjugates can be used to detect 1, 2, 3 or more targets in a sample by color.

21 Claims, 2 Drawing Sheets

(56) References Cited

OTHER PUBLICATIONS

Nguyen, Trung et al., "A Practical Synthetic Route to Functionalized Rhodamine Dyes," Org. Lett., vol. 18, 2003, 12 pages.
Raap, A K. et al., "Ultra-sensitive FISH Using Peroxidas-Mediated Deposition of Biotin- or Fluorochrome Tyramides," Human Molecular Genetics, vol. 4, No. 4, 1995, 529-534.
Van Der Loos, Chris M. et al., "Multiple Immunoenzyme Staining: Methods and Visualizations for the Observation With Spectral Imaging," Journal of Histochemistry & Cytochemistry, vol. 56, No. 4, Apr. 1, 2008, 313-328.
Yu, Mei-Juan et al., "A Study on Novel Fluorescent Probe Containing Rhodamine Structure (I)—Tautomerism and Spectroscopic Characteristics," Dyestuffs and Coloration, vol. 41, No. 4, Aug. 30, 2004, 187-190.
Adamczyk, Maciej et al., "Synthesis of Novel Spirolactams by Reaction of Fluorescein Methyl Ester With Amines," Tetrahedron Letters, vol. 41, 2000, 807-809.
Nguyen, Trung et al., "Practical Synthetic Route to Functionalized Rhodamine Dyes," Organic Letters, vol. 5, No. 18, Jun. 19, 2003, 4 pages.
EPO, "Extended European Search Report Received mailed on May 8, 2024," Application No. 24152225.9, 11 pages.
Miyagawa-Yamaguchi, Arisa et al., "Each GPI-Anchored Protein Species Forms A Specific Lipid Raft Depending on Its GPI Attachment Signal," Glycoconjugate Journal, Chapman & Hall, Boston, vol. 32, No. 7, XP035601170, May 7, 2015, 531-540.

* cited by examiner

CHROMOGENIC PEROXIDASE SUBSTRATES

CROSS-REFERENCE TO RELATED APPLICATIONS

This application is a continuation of U.S. application Ser. No. 17/885,188, filed Aug. 10, 2022, which is a continuation of U.S. application Ser. No. 16/688,076, filed Nov. 19, 2019, which is a continuation of U.S. application Ser. No. 15/383,996, filed Dec. 19, 2016, which are incorporated by reference herein. This application also claims benefit of the filing date of and right of priority to U.S. Provisional Application No. 62/269,575, filed Dec. 18, 2015, which is incorporated by reference herein.

FIELD OF THE INVENTION

The present disclosure relates to chromogenic conjugates, methods of chromogenic analysis, such as ImmunoHistoChemistry (IHC) and Chromogen In Situ Hybridization (CISH), and methods of making chromogenic conjugates.

BACKGROUND

When analyzing tissue samples on a microscope slide, staining the tissue or certain parts of the tissue with a colored dye can aid the analysis. The ability to visualize or differentially identify microscopic structures is frequently enhanced through the use of histological stains. Hematoxylin and eosin (H&E) stain is the most commonly used stain in light microscopy for histological samples. Hematoxylin is used to stain nuclei blue, and eosin stains cytoplasm and the extracellular connective tissue matrix pink. In addition to H&E stains, other stains or dyes have been applied to provide more specific staining and provide a more detailed view of tissue morphology. Immunohistochemistry (ICH) stains have great specificity, as they use a peroxidase substrate or alkaline phosphotase (AP) substrate for IC stainings, providing a uniform staining pattern that appears to the viewer as a homogeneous color with intracellular resolution of cellular structures. e.g. membrane, cytoplasm, and nucleus.

Formalin Fixed Paraffin Embedded (FFPE) tissue samples, metaphase spreads or histological smears are typically analyzed by staining on a glass slide, where a particular biomarker, such as a protein or nucleic acid of interest, can be stained with H&E and/or with a colored dye, hereafter "chromogen" or "chromogenic moiety". IHC staining is a common tool in evaluation of tissue samples for the presence of specific biomarkers. IHC stains are precise in the recognition of specific targets in throughout the sample and allow quantification of these targets.

IHC staining employs chromogenic and/or fluorescent reporters that mark targets in histological samples. This is carried out by linking the biomarker directly or indirectly with an enzyme, typically either Horse Radish Peroxidase (HRP) or Alkaline Phosphatase (AP), that subsequently catalyzes the formation of an insoluble colored precipitate, at the location of the biomarker from a soluble suitable enzyme substrate, which exhibits a color.

In blotting/capture assays, the biomarker is extracted into solution from its original location and then re-immobilized on a membrane, gel, or chip array, but the biomarker is also stained with a visible color, a chromogen, typically by action of the same HRP or AP enzymes.

Compared to other detection techniques, such as radioactivity, chemo-luminescence or fluorescence, chromogens generally suffer from much lower sensitivity, but have the advantage of a permanent, plainly visible color which can be visually observed, such as with bright field microscopy. Other limitations of enzyme-based chromogenic detection of targets in solid biological samples or targets that are immobilized onto or into a solid support include that there is a very limited number of chromogenic HRP and AP substrates that can be used for target staining, which limits use of these target visualization systems for detection of multiple targets in samples. Also, some chromogens, like the HRP substrate 3,3'-diaminobenzidine (DAB), are not characterized by well-defined spectral features, but rather insoluble light adsorbing brown precipitates. Moreover, where visualization of multiple targets is concerned, it often requires one to use a combination of multiple enzyme-based visualization systems, such as HRP and AP. These limitations make sample staining procedures complex, less robust and expensive and also complicates automated detection of targets and image analyses of stained samples.

Rhodamines, rhodols and fluoresceins are intensely colored and fluorescent, They come in virtually any color, dependent on halogenation and/or substitution pattern. They have been known for more than a century, and several are used as special stains which stain tissue samples without any enzyme activity. For example, Rhodamine 110 is used as a mitochondrial stain, TetraBromoFluorescein, also referred to as Eosin, is used extensively in Haematoxilin/Eosine (H and E) double stains, where Haematoxilin stains nuclei blue and Eosin stains essentially any protein pink or red. So while derivatives of these compounds would seem attractive as potential chromogens due to their distinct and bright color, unspecific tissue staining, even in the absence of any enzyme activity, is an impediment to their use as chromogens. Another impediment is to provide derivatives with suitable solubility in aqueous environments.

Rhodamine and fluorescein compounds are also stable and require forcing conditions to undergo further reaction. A solution has been to introduce extra reactive groups, such as an IsoThioCyanate as in FluoresceinIsoThioCyanate ("FITC") and Tetramethyl Rhodamine IsoThioCyanate ("TRITC") or CarboxyFluorescein and SulphoRhodamine. However, the addition of these reactive groups is not done easily and results in a mixture of two almost inseparable isomers. FITC has become widely associated with reactive fluorescein, the proven way to prepare fluorescein derivatives of antibodies and nucleic acid probes. However such derivatives are expensive, some prohibitively expensive.

In the last decade, there has been progress made within the field of rhodanine and fluorescein 2T-ester derivatives. See, for example Beija, Mariana et al., "Synthesis and applications of Rhodamine derivatives as fluorescent probes." Chem. Soc. Rev., 2009, 38, 2410-2433; Afonso, A. M. Carlos, et al., "An Expedient Synthesis of Cationic Rhodamine Fluorescent Probes Suitable for Conjugation to Amino Acids and Peptides." Synthesis, 2003, 17, 2647-2654; Xi Chen et al., "An efficient and versatile approach for the preparation of a rhodamine B ester bioprobe library." Dyes and Pigments 2012, 94, 296-303.

Both rhodamines and fluoresceins possess a 2' carboxylic acid that can be derivatized as esters or amides under certain conditions. However, 2' primary amides of rhodamines or fluoresceins collapse into colorless spirolactam or spirolactone tautomers, making such derivatives unsuitable as chromogens. Esters and amides of secondary amines do not undergo this tautomerization as they lack the labile N—H proton.

A method of preparing amides of the secondary amine piperazine of Rhodamines and Fluorescein have been reported. See Nguyen T. et al., "Practical synthetic route to rhodamine dyes", Org. Lett. 2003, 18, 3245-48; Huang, Chusem, et al.; "Versatile Probes for the Selective Detection of Vicinal-Dithiol-Containing proteins: Design, Syntheses, and Applications in Living Ceils". Chem. Eur. J. 2013, 19, 7739-7747.

Fluorescein isothiocyanate (FITC) is a derivative of fluorescein used in many applications employing fluorescence, such as flow cytometry. FITC comprises a fluorescein molecule functionalized at its 4' position with a isothiocyanate reactive group (—N=C=S) on the monocyclic phenyl of the structure. This derivative is reactive towards nucleophiles including amine and sulfhydryl groups on proteins.

Use of fluorecein as the detectable part of HRP substrates in histochemical detection of targets has recently been described. WO2007/015168 to Lohse relates to monomeric or polymeric linker molecules useful in biological and chemical applications, their synthesis, and the synthesis and use of derivatives of the linkers conjugated to a variety of detectable labels and other substances. The linkers may be used, for example, in conjunction with fluorescent labels, nucleic acid or nucleic acid analog probes, and solid phase systems, and to enhance the solubility of the conjugated molecules. WO2009/036760, WO2010/094283, WO2010/094284, WO2011/047680 and WO2012/143010 relate to HRP substrates that are conjugated via linker of WO2007/015168 to fluorescein at its 4' position. The latter conjugates are colorless but fluorescent and can be used either for direct fluorescent or indirect histochemical detection of targets: the conjugates are deposited in target sites labeled with HRP activity via the enzymatic reaction, and then the deposited conjugates may be detected optically as fluorescent stain or immunochemically as haptens. Deposition of the conjugates by HRP demands presence of certain amounts of DAB, ferulic acid or alpha-cyano-4-hydroxycinnamic acid (ACHCA) in the deposition medium.

SUMMARY OF THE INVENTION

The present disclosure provides chromogenic conjugate molecules capable of serving as substrates of an enzyme with peroxidase activity, and describes their utility for detecting molecular targets in samples.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

Figure 1:
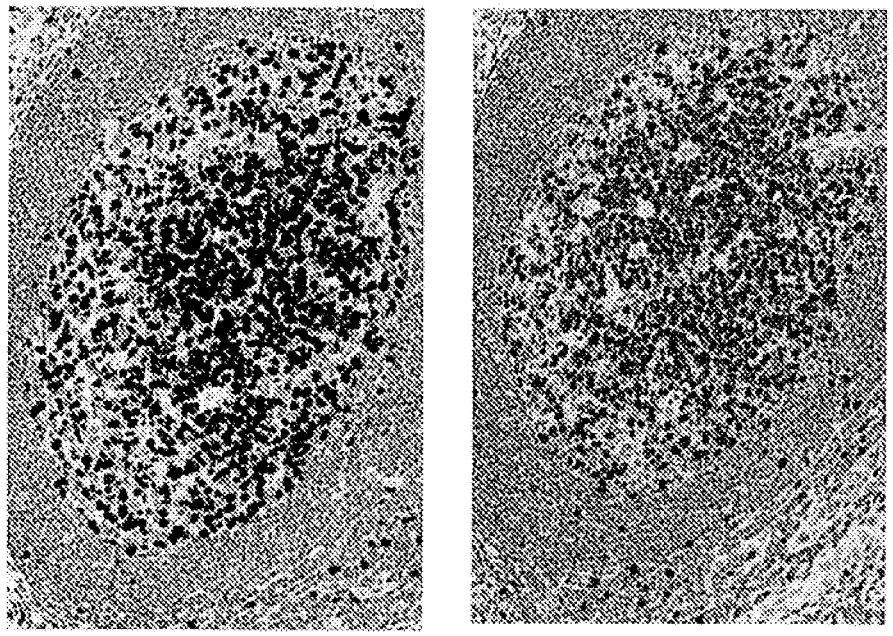
FIG. 1 is a photomicrograph of Ki67 stained tonsil tissue. The photo on the left was stained with Compound 2 (described below); the photo on the right was stained with DAB.

It is to be understood that the terminology used herein is for purposes of describing particular embodiments only, and is not intended to be limiting. The defined terms are in addition to the technical and scientific meanings of the defined terms as commonly understood and accepted in the technical field of the present teachings. For example, definitions of common terms in molecular biology may be found in Benjamin Lewin, *GenesVII*, published by Oxford University Press, 2000 (ISBN019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN0471186341); and other similar references.

As used in the specification and appended claims, the terms "a", "an" and "the" include both singular and plural referents, unless the context clearly dictates otherwise. Thus, for example, "a moiety" includes one device and plural moieties.

As used in the specification and appended claims, and in addition to their ordinary meanings, the terms "substantial" or "substantially" mean to within acceptable limits or degree to one having ordinary skill in the art. For example, "substantially cancelled" means that one skilled in the art considers the cancellation to be acceptable.

As used in the specification and the appended claims and in addition to its ordinary meaning, the terms "approximately" and "about" mean to within an acceptable limit or amount to one having ordinary skill in the art. The term "about" generally refers to plus or minus 15% of the indicated number. For example, "about 10" may indicate a range of 8.7 to 1.15. For example, "approximately the same" means that one of ordinary skill in the art considers the items being compared to be the same.

A "moiety" is a portion of a molecule that retains chemical and/or physical and/or functional features of the entire molecule, that are relevant for performance of the chromogenic conjugates; e.g., "peroxidase substrate moiety" is a portion of a molecule capable of serving as substrate of an enzyme with peroxidase activity; "peroxidase moiety" is a portion of a molecule that has inherent peroxidase activity, e.g. an enzyme.

A "conjugate" refers to two or more molecules (or two or moieties of two or more molecules) that are covalently linked into a larger construct.

The term "linked" in the present context means connected via a chemical bond.

A "target" is an object in a test sample to be detected by use of the present chromogenic conjugates and methods; present targets include chemical and biological molecules and structures. Embodiments of present targets are discussed herein.

A "biological marker" refers to one or more biological objects such as molecules, molecular complexes, structures, particles or organisms which are associated with features that are characteristic for a particular cell type, tissue, cellular structure, physiological condition, etc. Such biological objects are often considered markers of that particular cell type, tissue, cellular structure, or physiological condition. Non-limited examples of such biological markers include but not-limited to particular nucleotide sequences, proteins or other biological molecules, e.g. carbohydrates or lipids, chromosomal or membrane structures, viruses, bacteria, microorganisms etc. In some embodiments, the term target is used interchangeable with the term biological marker and relates to a molecule, molecular complex, structure or particle that is characteristic for a particular cell type, tissue, physiologic condition, etc, wherein the total population of any of the latter biological markers in the test sample is considered to be the target.

"Spectral characteristics" are characteristics of electromagnetic radiation emitted or absorbed due to a molecule or moiety making a transition from one energy state to another energy state, for example from a higher energy state to a lower energy state. Only certain colors appear in a molecule's or moiety's emission spectrum, since certain frequencies of light are emitted and certain frequencies are absorbed. Spectral characteristics may be summarized or referred to as the color of the molecule or moiety.

The term "rhodamine" can refer to the family of related dyes based on xanthene, which includes Rhodamine 6G and Rhodamine B; or the term "rhodamine" can refer to the specific compound:

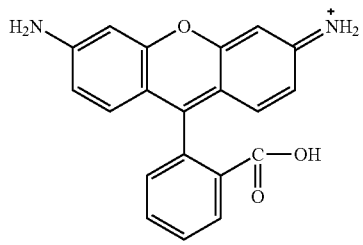 [SMILES: Nc1ccc2c(-c3ccccc3C(=O)O)c3ccc(=[NH2+])cc-3oc2c1]

as context indicates.

The term "fluorescein" can refer to the family of related dyes based on xanthene, which includes fluorescein isothiocyanate, NHS-fluorescein, and O-carboxyfluorescein; or the term "fluorescein" can refer to the specific compound:

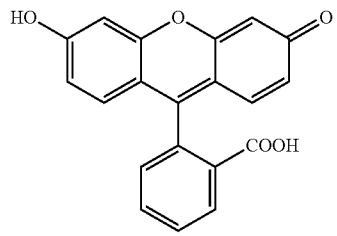 [SMILES: O=C(O)c1ccccc1-c1c2ccc(=O)cc-2oc2cc(O)ccc12]

Certain abbreviations are used for the sake of brevity: "Rho" refers to rhodamine; "TMRho" refers to tetra methyl rhodamine; "Flu" refers to fluorescein; "Pip" refers to piperazine; "Cou" refers to coumarin; "Caf" refers to caffeic acid; "Fer" refers to ferulic acid; "Cin" refers to cinnapinic acid; "Tyr" refers to tyrosine; "Et" refers to ethyl. Other abbreviations may also appear in this disclosure.

"Spectrally narrow" refers to a chromogen having less that 50 nm broadness at its maximum absorbance at half peak height by UV-VIS spectroscopy, measured in +99% water at pH, 6-8 in 10 μM concentration. A "magenta chromogen" is a spectrally narrow chromogen with peak absorbance between 525 and 536 nm, measured in +99% water at pH, 6.0-8.0 in 10 μM concentration. A "greenish-yellow chromogen" is a chromogen with peak absorbance below 475 nm and less than 10% absorbance at 530 nm or above relative to the peak absorbance, measured in +99% water at pH, 6.0-8.0 in 10 μM concentration A "yellow chromogen" is a chromogen with peak absorbance below 505 nm and less than 10% absorbance at 530 nm or above relative to the peak absorbance, measured in +99% water at pH, 6.0-8.0 in 10 μM concentration. A "cyan chromogen" is a chromogen having maximal absorbance above 615 nm and less than 10% relative absorbance at any wavelength between 530 and 400 nm relative to the peak absorbance, measured in +99% water at pH, 6.0-8.0 in 10 μM concentration. An "orange chromogen" is a "spectrally narrow" chromogen that has maximum absorbance between 495 and 520 nm, measured in +99% water at pH, 6-8 in 10 μM concentration. A "dichroic chromogen" is a chromogen that has at least two absorbance maxima, separated by a local minimum at least 50 nm wide and one further global minimum between 390 and 700 nm measured in water between pH 6 and 8.

DETAILED DESCRIPTION

In the following detailed description, for purposes of explanation and not limitation, representative embodiments disclosing specific details are set forth in order to provide a thorough understanding of the present teachings. Descriptions or details of known systems, compounds, materials, methods of use and methods of manufacture may be omitted so as to avoid obscuring the description of the example embodiments. Nonetheless, systems, moieties and methods that are within the purview of one of ordinary skill in the art may be used in accordance with the representative embodiments.

The present disclosure provides chromogenic peroxidase substrate conjugates (interchangeably termed herein as "chromogenic conjugates", "conjugate molecules" or "reporter molecules"). The present conjugate molecules combine one or more of the virtues of DAB, without one or more of the disadvantages.

Embodiments of the present chromogenic conjugates include molecules comprising a peroxidase substrate moiety linked to a chromogenic moiety, that are (a) non-toxic, (b) precipitated from solutions via HRP-mediated reaction as bright and spectrally narrow and intense stains; (c) are stable in aqueous solutions for more than 24 hours once mixed; and/or (d) are insoluble in organic solvents when precipitated.

In some embodiments, the chromogenic conjugates of the present disclosure adsorb and/or emit light in the range from about 450 nm to about 600 nm. In some embodiments, the chromogenic conjugate absorbs light at 536 nm and the color of stain may be defined as magenta. In some embodiments, the chromogenic conjugate is yellow and absorbs light at 450 nm. In some embodiments, the chromogenic conjugate is purple and absorbs light close to 600 nm. The embodiments of the present chromogenic conjugates can serve as substrates of a peroxidase enzyme, e.g. HRP, and they are spectrally narrow, non-dichromatic, and do not change their spectral characteristics upon precipitation; the stains produced via enzymatic precipitation of the chromogenic conjugates are poorly soluble, if at all, in water or organic solutions and do not bleach when exposed to light sources used for imaging of stained samples. These features make the present chromogenic conjugates particularly suitable for automated image analyses and multiplexing. Further, the molecules of the chromogenic conjugates have well-defined chemical structures and can easily be produced by the processes described herein.

Chromogenic Conjugate Molecules

Some embodiments of the present chromogenic conjugate may be represented by the general formula:

(S)-L-(Z), wherein S is a peroxidase substrate moiety,
Z is a chromogenic moiety,
L is a linker, wherein the chromogenic conjugate molecules have one, two, three, four, five or all, and preferably all, of the following features: (1) comprise one substrate moiety of a peroxidase enzyme, such as HRP substrates; (2) comprise one chromogenic moiety, which is a Rho or Flu 2'-ester or 2'-secondary amide derivative; (3) the enzyme substrate and chromogenic moieties are linked together via a water soluble linker compound and are distanced away from each other by at least 5 consecutively interconnected atoms, (4) the linker compound (also termed herein as "linker molecule", "linker" or "L") comprises a chain of 5-29 interconnected atoms (correspondingly abbreviated as "L5-L29"); wherein, in some preferred embodiments, the linker compound comprises two consecutive carbons followed by an oxygen or nitrogen atom; (5) the conjugate is substantially soluble in aqueous solutions; (6) the conjugate is substantially stable as a chromogen both in solution and as precipitate.

Table 1 sets forth some non-limiting examples of the present chromogenic conjugates:

TABLE 1

| Compound No. | Structure |
|---|---|
| 1 | 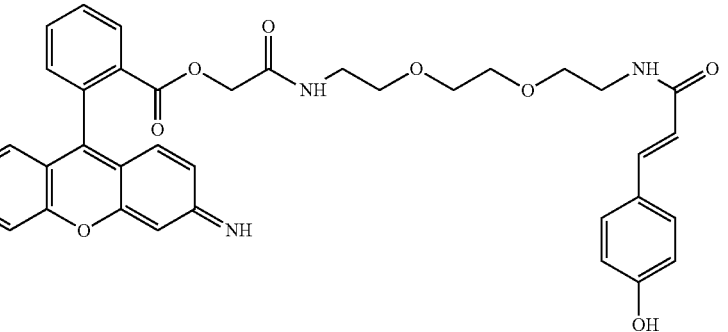<br>1 Rhodamine 110-L12-Cou |
| 2 | 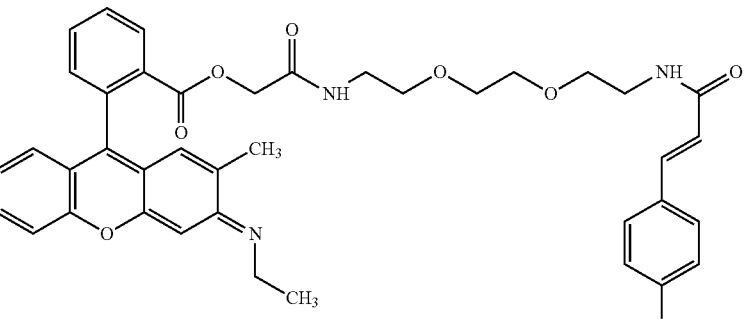<br>2 Rhodamine 6G-L12-Cou |
| 3 | 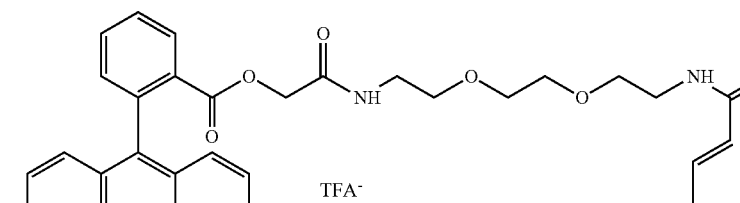<br>3 TetramethylRhodamine-L12-Cou |

TABLE 1-continued
| Compound No. | Structure |
|---|---|
| 4 | 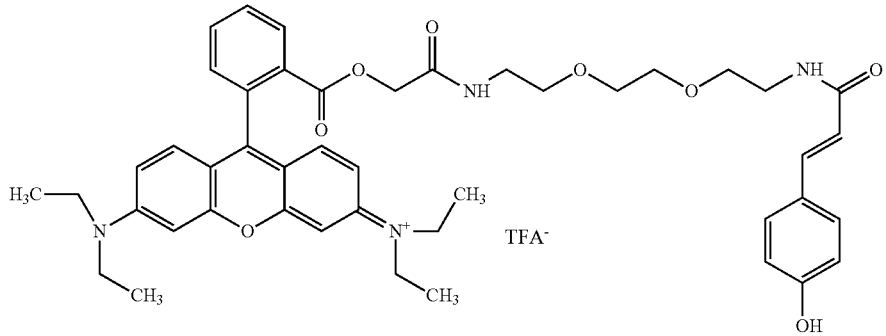<br>4-RhodamineB-L12-Cou |
| 5 | 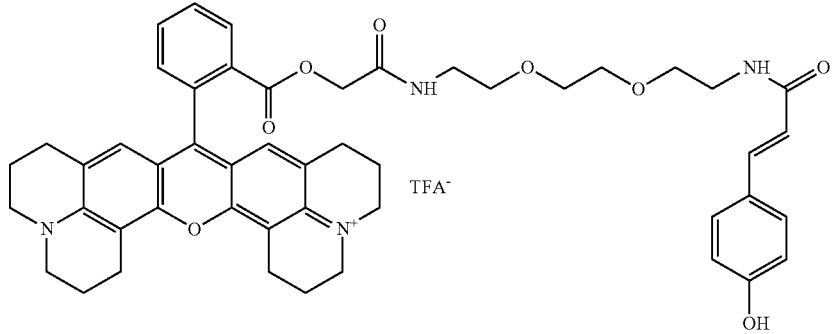<br>5 Rhodamine 101-L-12-Cou |
| 6 | 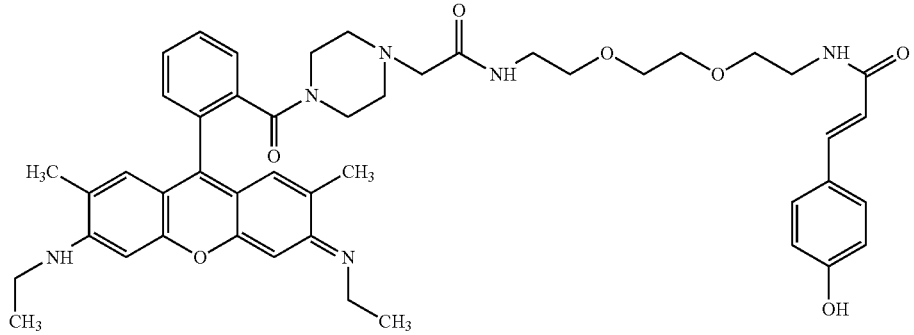<br>6 Rhodamine 6G-Pip-L12-Cou |
| 7 | 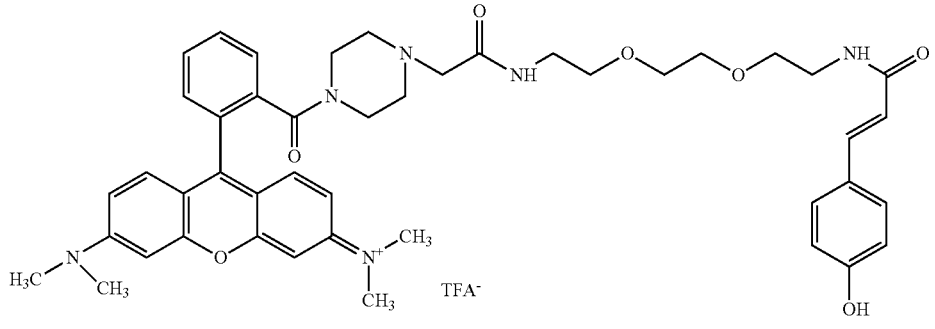<br>7 TM-Rhodamine-Pip-L12-Cou |

TABLE 1-continued
| Compound No. | Structure |
|---|---|
| 8 | 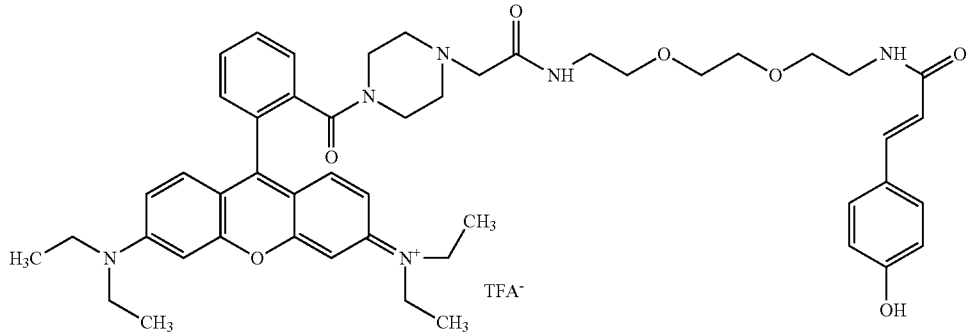<br>8 RhodamineB-Pip-L12-Cou |
| 9 | 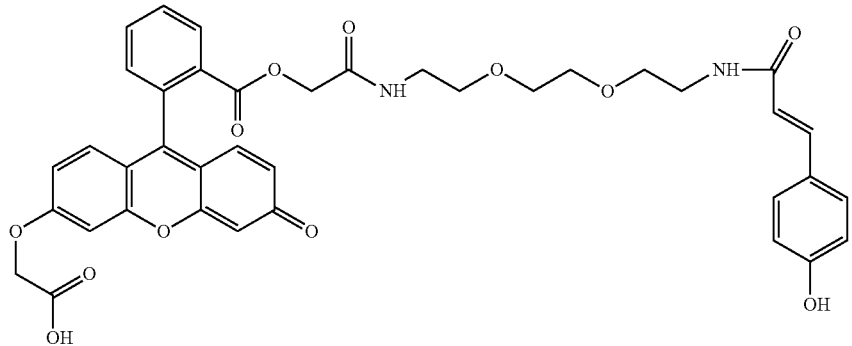<br>9 (O-carboxymethyl)-Flu-L12-Cou |
| 10 | 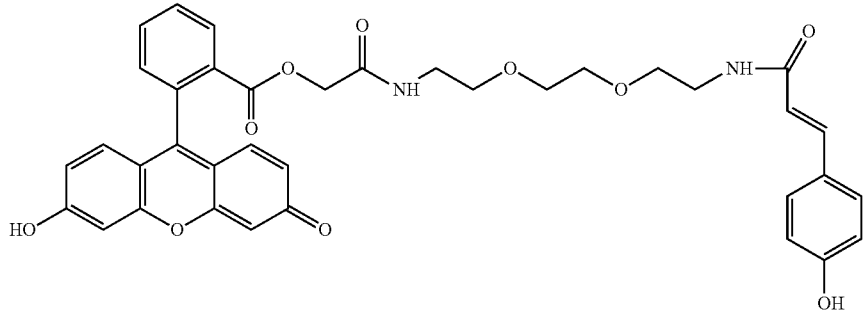<br>10 Flu-L12-Cou |
| 11 | 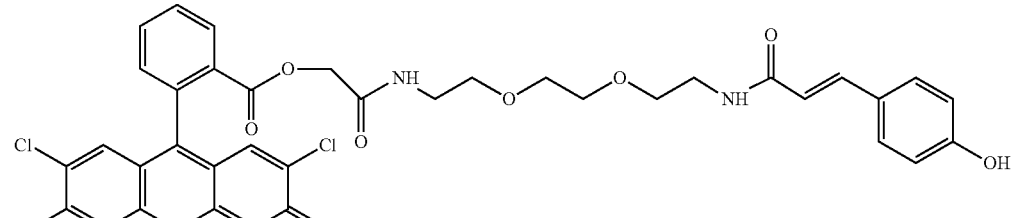<br>11 2,7-Dichloro-Flu-L12-Cou |

TABLE 1-continued
| Compound No. | Structure |
|---|---|
| 12 | 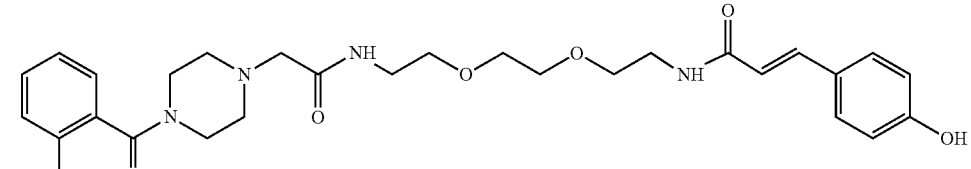<br>12 Flu-Pip-L12-Cou |
| 13 | 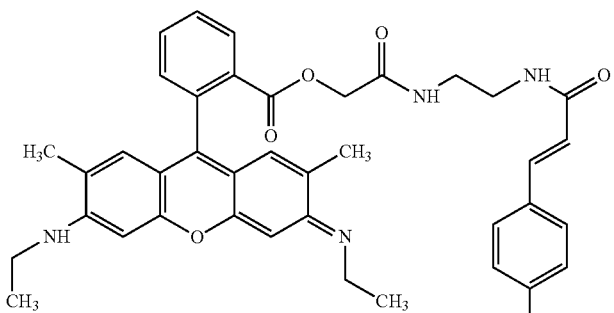<br>13. Rho6G-L6-Cou |
| 14 | 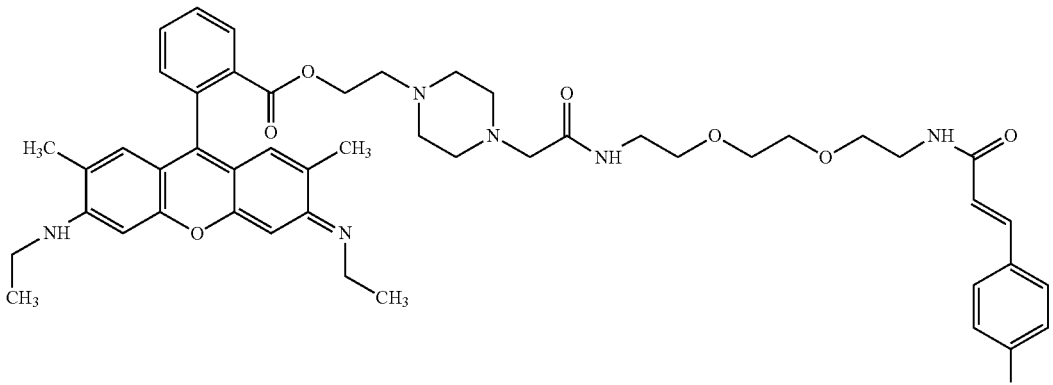<br>14 Rhodamine 6G-Et-Pip-L12-Cou |
| 15 | 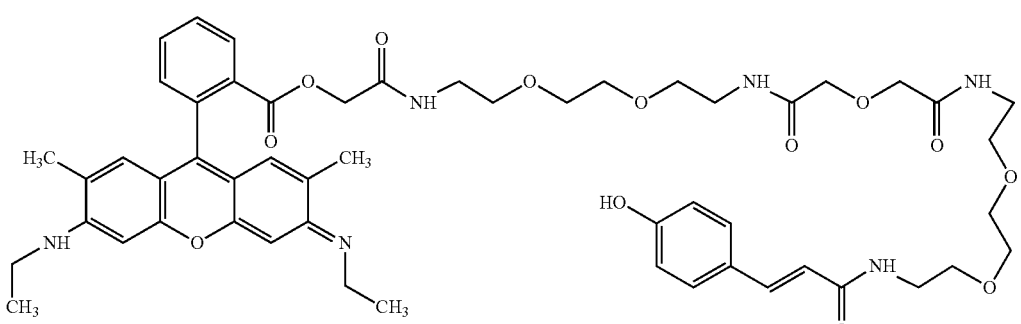<br>15. Rho6G-L27-Cou |

TABLE 1-continued
| Compound No. | Structure |
|---|---|
| 16 | 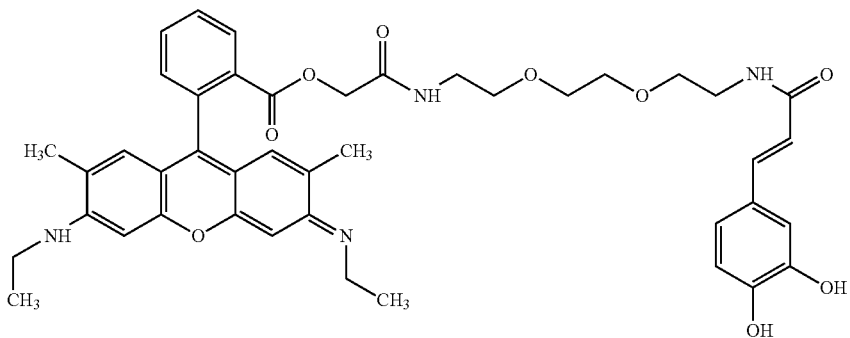<br>16 Rhodamine 6G-L12-Caf |
| 17 | 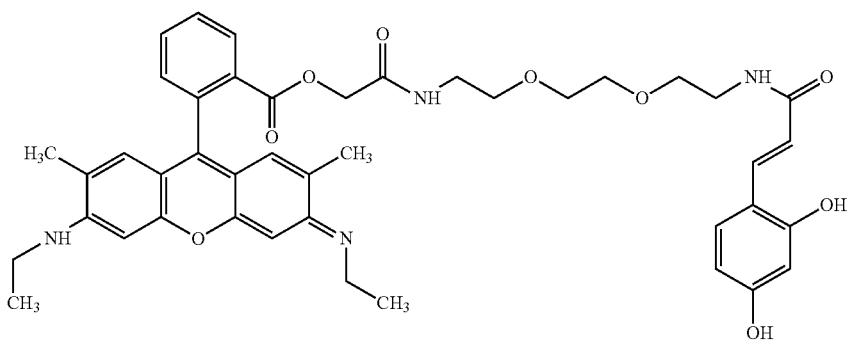<br>17 Rhodamine 6G-L12-2,4-OH-Cin |
| 18 | 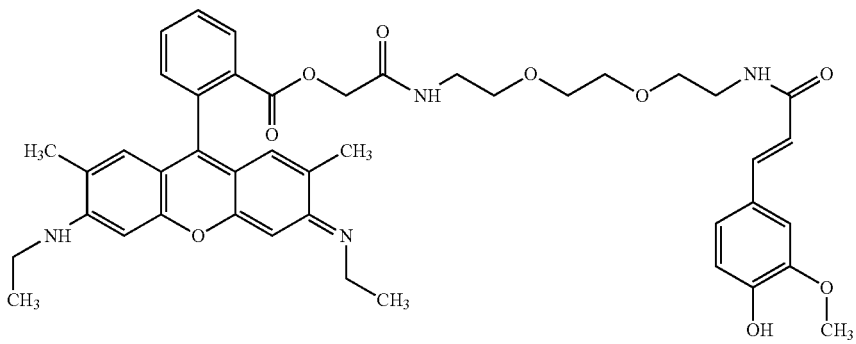<br>18 Rhodamine 6G-L12-Fer |
| 19 | 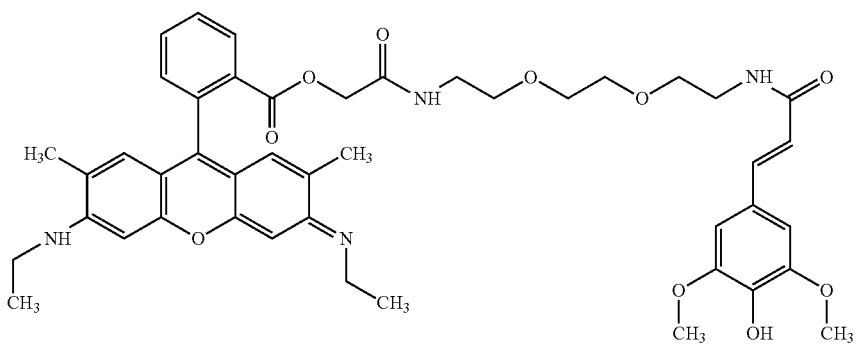<br>19 Rhodamine 6G-L12-Sin |

Table 2 lists the mass and absorption for these conjugates:

TABLE 2

| Cmpd No. | Trivial Name | Formula | Mol Mass (Calc) | Mol Mass (found) | Absp nm (max) |
|---|---|---|---|---|---|
| 1 | Rho110-L12-Cou | $C_{37}H_{36}N_4O_8$ | 664.7037 | 663.31 | 505 |
| 2 | Rho6G-L12-Cou | $C_{43}H_{48}N_4O8$ | 748.8632 | 749.36 | 531 |
| 3 | TMRho-12-Cou | $C_{41}H_{45}N_4O_8{}^Q$ | 721.8175 | 721.69 | 556 |
| 4 | RhoB-L12-Cou | $C_{45}H_{53}N_4O_8{}^Q$ | 777.9377 | 776.34 | 561 |
| 5 | Rho101-L12-Cou | $C_{49}H_{53}N_4O_8{}^Q$ | 825.9666 | 825.50 | 584 |
| 6 | Rho6G-Pip-L12-Cou | $C_{47}H_{56}N_6O_7$ | 816.9835 | 816.81 | 536 |
| 7 | TMRho-Pip-L 12-Cou | $C_{45}H_{53}N_6O_7{}^Q$ | 789.9378 | 790.54 | 561 |
| 8 | RhoB-Pip-L12-Cou | $C_{49}H_{61}N_6O_7{}^Q$ | 846.0441 | 845.79 | 567 |
| 9 | O-(carboxymethyl)-Flu-L12-Cou | $C_{39}H_{36}N_2O_{12}$ | 724.7093 | 725.29 | 458 |
| 10 | Flu-L12-Cou | $C_{37}H_{34}N_2O_{10}$ | 666.6733 | 667.23 | 503 |
| 11 | 2,7-DiChloro-Flu-L12-Cou | $C_{37}H_{32}N_2O_{10}Cl_2$ | 735.564 | 736.77 | 517 |
| 12 | Flu-Pip-L12-Cou | $C_{41}H_{42}N_4O_9$ | 734.7936 | 735.34 | 508 |
| 13 | Rho6G-L6-Cou | $C_{39}H_{40}N_4O_6$ | 660.7581 | 660.81 | 532 |
| 14 | Rho6G-Et-Pip-L12-Cou | $C_{49}H_{60}N_6O_8$ | 861.0361 | 861.34 | 531 |
| 15 | Rho6G-L27-Cou | $C_{53}H_{66}N_6O_{13}$ | 995.1235 | 995.35 | 533 |
| 16 | Rho6G-L12-Caf | $C_{43}H_{48}N_4O_9$ | 764.8626 | 764.68 | 531 |
| 17 | Rho6G-L12-2,4-OH-Cin | $C_{43}H_{48}N_4O_8$ | 764.8626 | 764.68 | 531 |
| 18 | Rho6G-L12-Fer | $C_{44}H_{50}N_4O_9$ | 778.8892 | 779.54 | 531 |
| 19 | Rho6G-L12-Sin | $C_{45}H_{52}N_4O_{10}$ | 808.9152 | 808.83 | 531 |

As shown by Table 2, chromogenic conjugates having distinct absorption maxima have been made. This allows staining of a tissue sample with one or more distinct color. For example a method of analyzing a sample may comprise labeling a first target with Compound 14, so that the first target is detected, or identified at places of the sample, with magenta stain, and labeling a second target with Compound 5, so that the second target is detected or identified as purple stain.

Surprisingly a systematic trend was observed in the peak absorbances of the chromogenic conjugates having piperazine amides and ethers. The piperazine amides absorb approximately 15 nm higher than corresponding rhodamine and fluorescein and ester-comprising conjugates absorb approximately 10 nm above the corresponding rhodamine and fluorescein. This enables fine tuning of the hue of the chromogenic conjugates.

Chromogenic Moiety

The chromogenic conjugates may include a chromogenic moiety capable of providing visible color. The chromogenic moiety may be a xanthene derivative, such as a fluorescein, rhodol or rhodamine residue.

In some embodiments, the chromogenic conjugate comprises (a) a chromogenic moiety, and (b) a peroxidase substrate moiety, wherein the chromogenic moieties and the peroxidase substrate moieties are linked together via a linker, and wherein the linker comprises at least one linear chain of at least 5 consecutively connected atoms. For example, the chromogenic conjugate can be a compound of formula I:

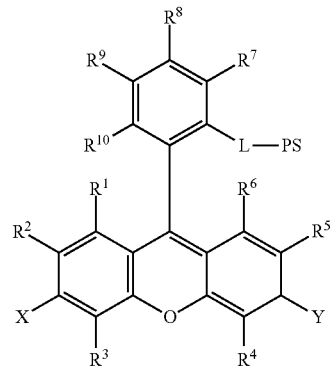

where X is —OH, —OR$^X$ or —NR$^X$R$^{XX}$,
where Y is =O or =N$^+$R$^Y$R$^{YY}$;
wherein R$^1$, R$^2$, R$^3$, R$^4$, R$^5$, R$^6$, R$^7$, R$^8$, R$^9$, R$^{10}$, R$^X$, R$^{XX}$, R$^Y$, and R$^{YY}$ are independently selected from hydrogen and a substituent having less than 40 atoms;
L is a linker; and
PS is a peroxidase substrate moiety.

In some embodiments certain combinations of residues X and Y may be preferred. For example, if X is —OH or —OR$^X$, then the preferred Y is =O. In another preferred combination, if X is —NR$^X$R$^{XX}$, then Y is =N$^+$R$^Y$R$^{YY}$.

In some embodiments of the chromogenic conjugate of Formula I, R$^1$ is selected from hydrogen, R$^{11}$, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different R$^{13}$ or suitable R$^{14}$ groups, or alternatively, R$^1$ may be taken together with R$^2$ to form part of a benzo, naptho or polycyclic aryleno group which is optionally substituted with one or more of the same or different R$^{13}$ or suitable R$^{14}$ groups.

In some embodiments of the chromogenic conjugate of Formula I, R$^2$ is selected from hydrogen, R$^{11}$, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different R$^{13}$ or suitable R$^{14}$ groups, or alternatively, R$^2$ may be taken together with R$^1$, to form part of a benzo, naphtho or polycyclic aryleno group which is optionally substituted with one or more of the same or different R$^{13}$ or suitable R$^{14}$ groups, or alternatively, when X is —NR$^X$R$^{XX}$, R$^2$ may be taken together with R$^X$ to form a 5- or 6-membered ring which is optionally substituted with one or more of the same or different R$^{13}$ or suitable R$^{14}$ groups.

In some embodiments of the chromogenic conjugate of Formula I, R$^X$, when present, is selected from hydrogen, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different R$^{13}$ or suitable R$^{14}$ groups, or, alternatively, R$^X$ may be taken together with R$^2$ to form a 5- or 6-membered ring which is optionally substituted with one or more of the same or different $R^{13}$ or suitable $R^{14}$ groups.

In some embodiments of the chromogenic conjugate of Formula I, $R^{XX}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^{XX}$ may be taken together with $R^3$ to form a 5- or 6-membered ring which is optionally substituted with one or more of the same or different $R^{13}$ or suitable $R^{14}$ groups.

In some embodiments of the chromogenic conjugate of Formula I, $R^3$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, when X is —$NR^X R^{XX}$, $R^3$ may be taken together with $R^{XX}$ to form a 5- or 6-membered ring which is optionally substituted with one or more of the same or different $R^{13}$ or suitable $R^{14}$ groups.

In some embodiments of the chromogenic conjugate of Formula I, $R^4$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, when Y is —$N^+R^Y R^{YY}$, $R^4$ may be taken together with $R^{YY}$ to form a 5- or 6-membered ring which is optionally substituted with one or more of the same or different $R^{13}$ or suitable $R^{14}$ groups; $R^{yy}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively $R^{yy}$ may be taken together with $R^4$ to form a 5- or 6-membered ring which is optionally substituted with one or more of the same or different $R^{13}$ or suitable $R^{14}$ groups.

In some embodiments of the chromogenic conjugate of Formula I, $R^Y$, when present, is selected from hydrogen, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^Y$ may be taken together with $R^5$ to form a 5- or 6-membered ring optionally substituted with one or more of the same or different $R^{13}$ or suitable $R^{14}$ groups.

In some embodiments of the chromogenic conjugate of Formula I, $R^{YY}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^{XX}$ may be taken together with $R^6$ to form a 5- or 6-membered ring which is optionally substituted with one or more of the same or different $R^{13}$ or suitable $R^{14}$ groups.

In some embodiments of the chromogenic conjugate of Formula I, $R^5$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^5$ may be taken together with $R^6$ to form part of a benzo, naptho or polycyclic aryleno group which is optionally substituted with one or more of the same or different $R^{13}$ or suitable $R^{14}$ groups, or alternatively, when Y is —$N^+R^Y R^{YY}$, $R^5$ may be taken together with $R^y$ to form a 5- or 6-membered ring optionally substituted with one or more of the same or different $R^{13}$ or suitable $R^{14}$ groups.

In some embodiments of the chromogenic conjugate of Formula I, $R^6$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^6$ together with $R^5$ may form part of a benzo, naptho or polycyclic aryleno group which is optionally substituted with one or more of the same or different $R^{13}$ or suitable $R^{14}$ groups.

In some embodiments of the chromogenic conjugate of Formula I, $R^7$, $R^8$ and $R^9$ are each, independently of one another, selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups.

In some embodiments of the chromogenic conjugate of Formula I, $R^{10}$ is selected from selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, halo, haloalkyl, —$OR^{12}$, —$SR^{12}$, —$SOR^{12}$, —$SO_2R^{12}$, and nitrile.

In some embodiments, $R^{11}$ is selected from —$NR^{15}R^{15}$, —$OR^{16}$, —$SR^{16}$, halo, haloalkyl, —CN, —NC, —OCN, —SCN, —NO, —$NO_2$, —$N_3$, —$S(O)R^{16}$, —$S(O)_2R^{16}$, —$S(O)_2OR^{16}$, —$S(O)NR^{15}R^{15}$, —$S(O)_2NR^{15}R^{15}$, —$OS(O)R^{16}$, —$OS(O)_2R^{16}$, —$OS(O)_2NR^{15}R^{15}$, —$OP(O)_2R^{16}$, —$OP(O)_3R^{16}R^{16}$, —$P(O)_3R^{16}R^{16}$, —$C(O)R^{16}$, —$C(O)OR^{16}$, —$C(O)NR^{15}R^{15}$, —$C(NH)NR^{15}R^{15}$, —$OC(O)R^{16}$, —$OC(O)OR^{16}$, —$OC(O)NR^{15}R^{15}$ and —$OC(NH)NR^{15}R^{15}$.

In some embodiments, $R^{12}$ is selected from (C1-C20) alkyls or heteroalkyls optionally substituted with lipophilic substituents, (C5-C20) aryls or heteroaryls optionally substituted with lipophilic substituents and (C2-C26) arylalkyl or heteroarylalkyls optionally substituted with lipophilic substituents.

In some embodiments, $R^{13}$ is selected from hydrogen, (C1-C8) alkyl or heteroalkyl, (C5-C20) aryl or heteroaryl and (C6-C28) arylalkyl or heteroarylalkyl.

In some embodiments, $R^{14}$ is selected from —$NR^{15}R^{15}$, =O, —$OR^{16}$, =S, —$SR^{16}$, =$NR^{16}$, =$NOR^{16}$, halo, haloalkyl, —CN, —NC, —OCN, —SCN, —NO, —$NO_2$, =$N_2$, —$N_3$, —$S(O)R^{16}$, —$S(O)_2R^{16}$, —$S(O)_2OR^{16}$, —$S(O)NR^{15}R^{15}$, —$S(O)_2NR^{15}R^{15}$, —$OS(O)R^{16}$, —$OS(O)_2R^{16}$, —$OS(O)_2NR^{15}R^{15}$, —$OS(O)_2OR^{16}$, —$OS(O)_2NR^{15}R^{15}$, —$C(O)R^{16}$, —$C(O)OR^{16}$, —$C(O)NR^{15}R^{15}$, —$C(NH)NR^{15}R^{15}$, —$OC(O)R^{16}$, —$OC(O)OR^{16}$, —$OC(O)NR^{15}R^{15}$ and —$OC(NH)NR^{15}R^{15}$.

In some embodiments, each $R^{15}$ is independently hydrogen or $R^{16}$, or alternatively, each $R^{15}$ is taken together with the nitrogen atom to which it is bonded to form a 5- to 8-membered saturated or unsaturated ring which may optionally include one or more of the same or different additional heteroatoms and which may optionally be substituted with one or more of the same or different $R^{13}$ or $R^{16}$ groups.

In some embodiments, each $R^{16}$ is independently $R^{13}$ or $R^{13}$ substituted with one or more of the same or different $R^{13}$ or $R^{17}$ groups.

In some embodiments, each $R^{17}$ is selected from —$NR^{13}R^{13}$, —$OR^{13}$, =S, —$SR^{13}$, =$NR^{13}$, =$NOR^{13}$, halo, haloalkyl, —CN, —NC, —OCN, —SCN, —NO, —$NO_2$, =$N_2$, —$N_3$, —$S(O)R^{13}$, —$S(O)_2R^{13}$, —$S(O)_2OR^{13}$, —$S(O)NR^{13}R^{13}$, —$S(O)_2NR^{13}R^{13}$, —$OS(O)R^{13}$, —$OS(O)_2R^{13}$, —$OS(O)_2NR^{13}R^{13}$, —$OS(O)_2OR^{16}$, —$OS(O)_2NR^{13}R^{13}$, —$C(O)R^{13}$, —$C(O)OR^{13}$, —$C(O)NR^{13}R^{13}$, —$C(NH)NR^{15}R^{13}$, —$OC(O)R^{13}$, —$OC(O)OR^{13}$, —$OC(O)NR^{13}R^{13}$ and —$OC(NH)NR^{13}R^{13}$.

Dichroic chromogens are chromogens that change hue or color with concentration. One example of a known dichroic chromogen is pumpkin seed oil. Pumpkin seed oil absorbs predominantly blue light, has an absorbance minimum for green light and a minor second absorbance peak in the far red wave lengths. With a short light path through the oil, the oil appears greenish. As the light path is increased, the color changes from brown to red. This change can be valuable if one is to measure the concentration of pumpkin seed oil by spectrophotometry. In low concentrations, precise measurements can be based on the blue absorbance. Furthermore, as the absorbance increases with concentration, rendering blue absorbance inaccurate (since blue light is substantially absorbed), one can switch to red absorbance (which is substantially inaccurate at low concentrations since no red light is substantially absorbed). Therefore, the technical effect of dichroic chromogens is that dichroic chromogens have an expanded dynamic range of human and instrument perception.

Dichroic effects can be obtained by mixing two or more chromogens of present disclosure. Since most are very spectrally narrow and absorb within the visible spectrum, any mixture of two chromogens with sufficiently separated absorbance maxima would be dichroic.

Various examples of mixing dichroic chromogens to produce chromogens that change hue with concentration are described below, referred to as dichroic orange and dichroic red.

In some embodiments, two or more chromogenic moieties are linked to each other so as to form a molecule or conjugate having two different absorptions. Suitable compounds include those of Formula XIV:

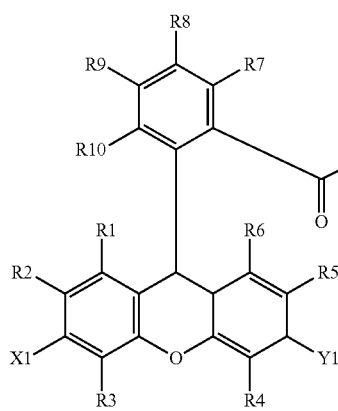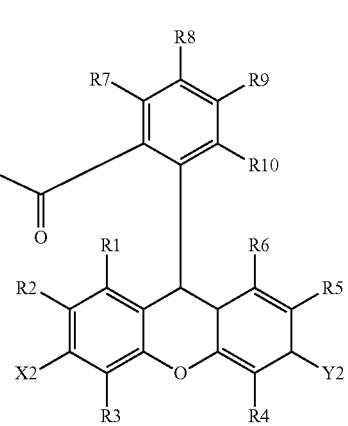

Formula XIV

In some embodiments, $R^1$, $R^2$, $R^3$, $R^4$, $R^5$, $R^6$, $R^7$, $R^8$, $R^9$, and $R^{10}$, are independently selected from —H, -halogen, -methyl, -ethyl, -propyl, -isopropyl, -vinyl, —$SO_3H$, —$PO_3H$, —$NO_2$, —COOH, —$NH_2$, —CN, —OH, —OMe and —OEt.

In some embodiments, the chromogenic moiety may be selected from the group consisting of rhodamine, rhodamine 6G, tetramethylrhodamine, rhodamine B, rhodamine 101, rhodamine 110, fluorescein, and O-carboxymethyl fluorescein and salts thereof. In some other embodiments, the chromogenic moiety may be selected from rhodamine 116, rhodamine 123, rhodamine 19. In some other embodiments the chromogenic moiety is a rhodamine salt comprising an anion selected from Cl⁻, Br⁻, TFA⁻, and $ClO_4^-$.

where X1 and X2 are selected from —OH, —$OR^X$ and —$NR^XR^{XX}$, and X1 and X2 are preferably different, where Y1 and Y2 are selected from =O or =NR and Y1 and Y2 are preferably different, wherein $R^1$, $R^2$, $R^3$, $R^4$, $R^5$, $R^6$, $R^7$, $R^8$, $R^9$, $R^{10}$, $R^X$, $R^{XX}$, R, and R are independently selected from hydrogen and a substituent having less than 40 atoms, or are as defined elsewhere in the present disclosure; and where $R^{34}$ is methyl, ethyl, propyl, $OCH_2$, $CH_2OCH_2$, $(CH_2OCH_2)_2$, $NHCH_2$, $NH(CH_2)_2$, $CH_2NHCH_2$, cycloalkyl, alkyl-cycloalkyl, alkyl-cycloalkyl-alkyl, heterocyclyl (such as nitrogen-containing rings of 4 to 8 atoms), alkyl-heterocyclyl, or alkyl-heterocyclyl-alkyl, preferably piperazine, piperidine, pyrrolidine, imidazolidine, pyrazolidine, azetidine, or other 4- to 8-membered (alternatively 5- to 7-membered) cyclic or heterocyclic group, optionally with an amine, a carboxyl or an ester substituent.

Preferred compounds of Formula XIV absorb light at least two distinct absorption maxima, for example, a first absorption maximum and a second absorption maximum which are separated by at least 5 nm, alternatively at least 10 nm, alternatively at least 20 nm.

For example, a double colored Rhodamine 6G-Fluorescein chromogen according to Formula XIVb has been made:

where $R^{38}$ is 4- to 8-membered cycloalkyl or a 4- to 8-membered heterocyclyl (such as nitrogen-containing rings of 4 to 8 atoms), preferably piperidinyl or piperazinyl.

Preferred compounds of Formula XIVa are those where the emission of a first chromogenic moiety (e.g., a fluorescein derivative) and the absorbance of a second chromogenic moiety (e.g., a rhodamine derivative) overlap.

Formula XIVb

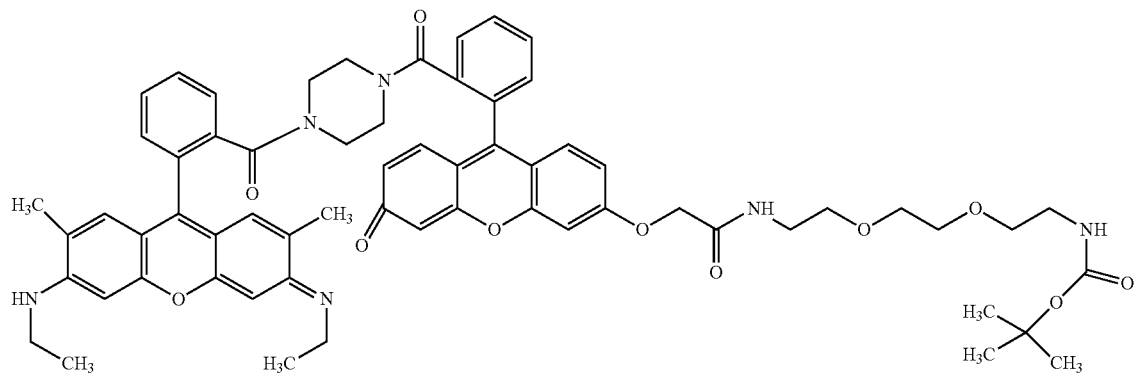

This compound exhibits an orange-red color. It still has a Boc-group, so a peroxidase substrate such as coumaric acid can be added.

In some embodiments where two or more chromogenic moieties are linked to each other in a conjugate, the conjugate having two different absorptions. For example, the present disclosure provides FRET conjugates of Formula XIVa:

In some embodiments of Formulas XIV and XIVa, a conjugate comprises a first chromogenic moiety and a second chromogenic moiety, and the first chromogenic moiety is a carboxy-fluorescein, and the second chromogenic moiety is selected from rhodamine 6G and rhodamine B.

In some embodiments of Formulas XIV and XIVa, one or more of $R^1$ to $R^{10}$ (preferably $R^{10}$) is optionally attached to a linker (L), and the linker is optionally attached to a Formula XIVa

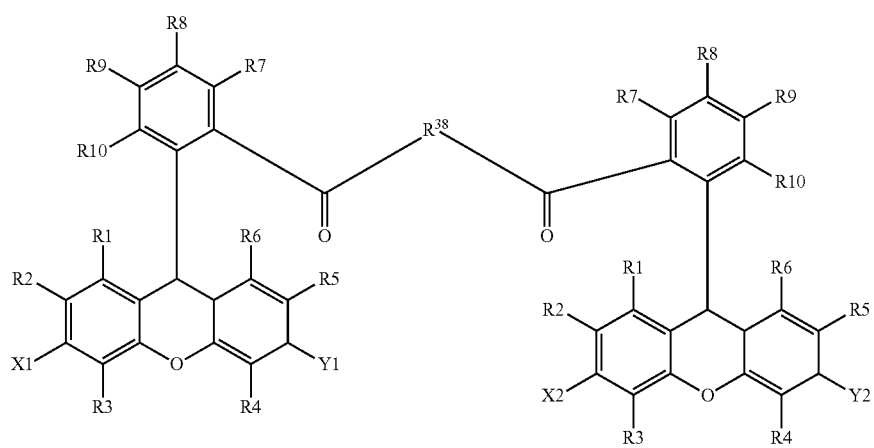

where X1 and X2 are selected from —OH, —OR$^X$ and —NR$^X$R$^{XX}$, and X1 and X2 are preferably different, where Y1 and Y2 are selected from =O or =N$^+$R$^Y$R$^{YY}$ and Y1 and Y2 are preferably different, wherein $R^1$, $R^2$, $R^3$, $R^4$, $R^5$, $R^6$, $R^7$, $R^8$, $R^9$, $R^{10}$, $R^X$, $R^{XX}$, $R^Y$, and $R^{YY}$ are independently selected from hydrogen and a substituent having less than 40 atoms, or are as defined elsewhere in the present disclosure; and peroxidase substrate (PS). Some embodiments of Formulas XIV and XIVa fall within Formula I when they comprise a chromogenic moiety linked to a peroxidase substrate via a linker of less than 30 atoms; such embodiments are not outside Formula I merely because they include a second chromogenic moiety. By having both colors built into the same molecule, the ratio between the two chromogenic moieties at a given site is fixed. In contrast, when mixing two chromogens of different colors, one chromogen may preferentially precipitate depending on diffusion, target intensity, and other factor, which may produce variable colors.

As yet another aspect, a chromogenic conjugate is provided according to Formula IX:

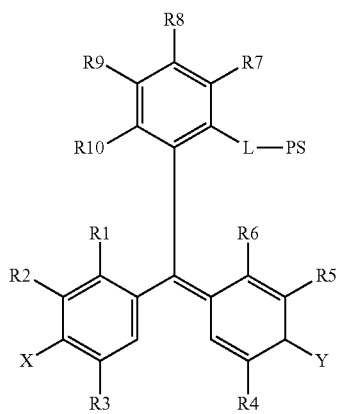

Formula IX where X is —OH, —OR$^X$ or —NR$^X$R$^{XX}$,
where Y is =O or =N$^+$R$^Y$R$^{YY}$;
wherein R$^1$, R$^2$, R$^3$, R$^4$, R$^5$, R$^6$, R$^7$, R$^8$, R$^9$, R$^{10}$, R$^X$, R$^{XX}$, R$^Y$, and R$^{YY}$ are independently selected from hydrogen and a substituent having less than 40 atoms;

L is a linker comprising a linear chain of 5 to 29 consecutively connected atoms; and PS is a peroxidase substrate moiety, such as the peroxidase substrates defined herein.

More particularly, a chromogenic conjugate is provided according to Formula IXa:

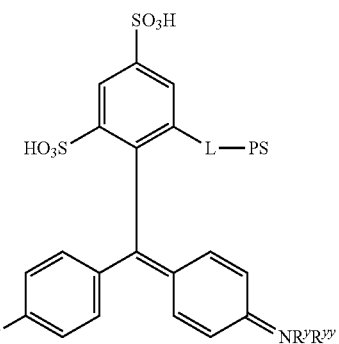

Formula IXa where L is a linker comprising a linear chain of 5 to 29 consecutively connected atoms; and PS is a peroxidase substrate moiety, such as the peroxidase substrates defined herein.

A new chromogen was produced which is referred to as compound 35 and has the following formula IXa:

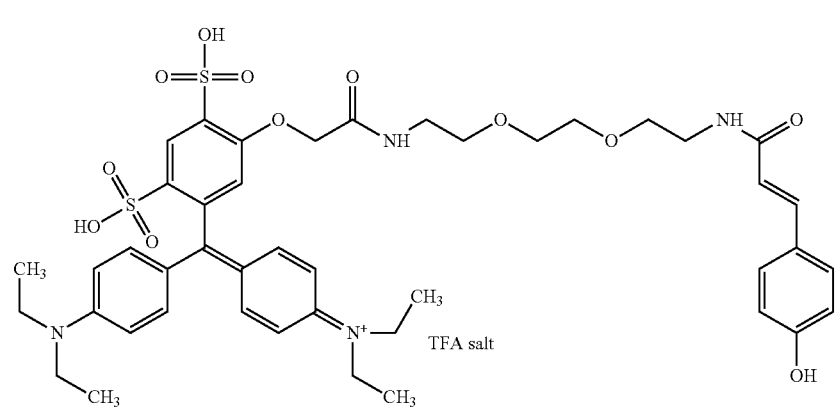

Formula IXb

Compound 35 is a cyan chromogen with an absorbance maximum at 640 nm in neutral water. Compound 35 can be combined with other chromogenic conjugates described herein to stain targets or samples with different colors.

Linker

In the present disclosure, a linker ("L") is a water soluble molecular moiety comprising a chain from 5 to less than 30 contiguous atoms, such as 29, 28, 27, 26, 25, 24, 23, 22, 21, 20, 19, 18, 17, 16, 15, 14, 13, 12, 11, 10, 9, 8, 7, 6 or 5 contiguous atoms. In some embodiments the chain of atoms may be liner, in other embodiments it may comprise one or more ring structures. In preferred embodiments, a linker molecule comprises a contiguous chain of 5 to 29 atoms, wherein every two connected carbon atoms are followed by a heteroatom, such as an atom of oxygen or nitrogen. In some embodiments, the linker has no more than two consecutively repeating ethyloxy groups.

In some embodiments, the linker is a compound that comprises 1 or 2 repeats of the following formula:

Formula III

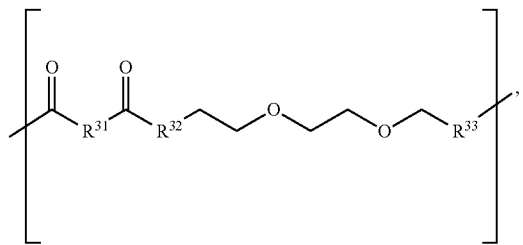

wherein $R^{31}$ is selected from methyl, ethyl, propyl, $OCH_2$, $CH_2OCH_2$, $(CH_2OCH_2)_2$, $NHCH_2$, $NH(CH_2)_2$, $CH_2NHCH_2$, cycloalkyl, alkyl-cycloalkyl, alkyl-cycloalkyl-alkyl, heterocyclyl (such as nitrogen-containing rings of 4 to 8 atoms), alkyl-heterocyclyl, alkyl-heterocyclyl-alkyl, and wherein no more than three consecutively repeating ethyloxy groups, and $R^{32}$ and $R^{33}$ are independently elected from NH and O. More particularly, in some embodiments, the linker is selected from Formulas IIIa, IIIb or IIIc:

Formula IIIa

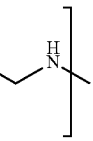

Formula IIIb

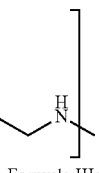

Formula IIIc

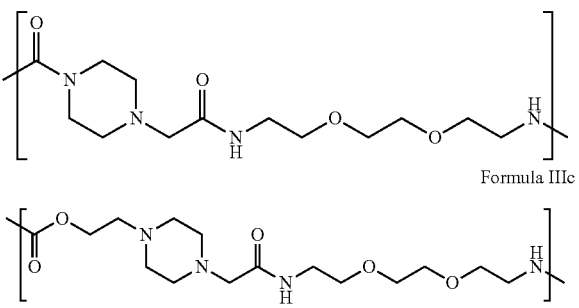

Linkers can be based on linker precursors such as Compound 22, wherein the linker precursors are adapted for reaction with peroxidase substrate moieties and chromogenic moieties or reactive precursors of peroxidase substrate moieties and chromogenic moieties. For example, Compound 22 can be used in the preparation of conjugates containing the linker of Formulas IIIa to IIIc by reacting Compound 22 with a peroxidase substrate moiety precursor such as COMU activated coumaric acid, and a chromogenic moiety precursor, such as tetramethylrhodamine piperazine amide hydrobromide.

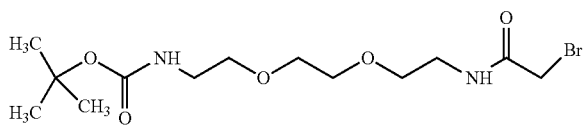 [SMILES: CC(C)(C)OC(=O)NCCOCCOCCNC(=O)CBr]

22   tert-butyl-N-[2-[2-[2-[(2-bromoacetyl)amino]ethoxy]ethoxy]ethyl]carbamate, $C_{13}H_{25}BrN_2O_5$ MW 369.252

Compound 22 can be prepared as described in Example 3 below or by other procedures. Other linkers and linker precursors can be prepared by the procedures set forth in WO2007/015168 to Lohse and elsewhere.

Properties of the linker can be modified to obtain desired performance, such as by altering the length or branching of the linker. Furthermore, the linker may be chemically modified to carry various substituents. The substituents may be further chemically protected and/or activated, allowing the linker to be derivatized further.

Peroxidase Substrate Moieties

The present chromogenic conjugates comprise a peroxidase substrate moiety. The term "peroxidase" relates to an enzyme having enzymatic activity catalyzing a reaction of the form:

ROOR'+electron donor($2e^-$)+$2H^+$→ROH+R'OH

For many peroxidases the optimal substrate is hydrogen peroxide, but others are more active with organic hydroperoxides such as organic peroxides. The nature of the electron donor is very dependent on the structure of the enzyme, e.g. Horseradish peroxidase (HRP)/EC 1.11.1.7) can use a variety of organic compounds both as electron donors and acceptors. HRP has an accessible active site, and many compounds can reach the site of the reaction.

The enzyme with peroxidase activity may be represented by a molecule of a peroxidase enzyme which is directly or indirectly linked to the molecule of a binding agent, or a fragment of the enzyme containing the enzymatic activity, e.g. 51% to 99.9% of the full size of the peroxidase molecule, or less than 51%.

The peroxidase may be directly or indirectly conjugated with other molecules, e.g. agents that are capable of binding targets of interest in a sample, such as a biological sample, e.g. a histological sample. The term "directly conjugated" means that the enzyme moiety is linked (e.g. chemically conjugated) to another molecule via a chemical bond; the term "indirectly conjugated" means that the peroxidase is linked to the molecule via a linker molecule, which has one chemical bond with binding agent and another chemical bond with peroxidase. Methods of conjugating enzyme moieties are well known in the art.

In one embodiment the moiety of peroxidase is a moiety of HRP, e.g. the whole HRP molecule a fragment thereof that is capable of the HRP enzymatic activity. It may also be a recombinant protein comprising the part of HRP that possesses the enzymatic activity, etc. In another embodiment the peroxidase may be soybean peroxidase (SP).

Non-limiting examples of agents which comprise an enzyme with peroxidase activity may be an antibody molecule, such as a primary or secondary antibody molecule or a derivative thereof, e.g. a Fab, directly or indirectly conjugated with one or more moieties of HRP, and nucleic acid binding agents conjugated with HRP. Such binding agents may bind directly or indirectly to targets and form thereby complexes, each comprising a target and one or more molecules of binding agents that comprise an enzyme with peroxidase activity.

The number of HRP or other peroxidase moiety per molecule of binding agent may vary from 1 to 10 or more, e.g. 20-50 or more.

A location of a solid sample (e.g. a histological sample) or a solid support (e.g. a membrane or microscopic slide) comprising peroxidase activity is sometimes termed herein "target site". In one embodiment the target site may comprise a peroxidase activity, such as a moiety of a peroxidase enzyme, which is directly immobilized onto or within a solid support. In another embodiment the target site may comprise a peroxidase activity which is immobilized onto or within a solid support indirectly, i.e. a moiety of a peroxidase enzyme is linked to an agent capable of directly or indirectly binding to a target that is immobilized onto or within the support.

In some embodiments, the peroxidase substrate moiety is a moiety of a substrate of horse radish peroxidase (HRP) or soybean peroxidase (SP). In some embodiments, the peroxidase substrate moiety (also identified as S or PS in some formulas) is a moiety of a non-chromogenic or colorless HRP or SP substrate. In some embodiments, the moiety of peroxidase enzyme substrate has the following formula (Formula II):

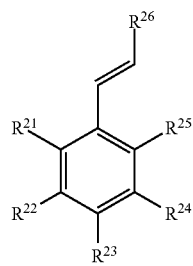

wherein $R_{21}$ is —H, —O—X, or —N(X)$_2$;
$R_{22}$ is —H, —O—X, or —N(X)$_2$;
$R_{23}$ is —OH;
$R_{24}$ is —H, —O—X, or —N(X)$_2$;
$R_{25}$ is —H, —O—X, or —N(X)$_2$;
$R_{26}$ is —CON—(X)$_{(2)}$, —CONH(X), or COO(X);
wherein H is hydrogen; O is oxygen; N is nitrogen; and X is H, alkyl or aryl. In some embodiments S or PS is a residue of ferulic acid. In other embodiments S is a residue of caffeic acid. In other embodiments S or PS is a residue of sinapinic acid. In one preferred embodiment S is a residue of coumaric acid.

Composition Comprising Chromogenic Conjugate

As another aspect, a composition comprising any of the chromogenic conjugates described herein (termed herein as "chromogenic composition" or "chromogenic medium") is provided. Some compositions include one of the chromogenic conjugates described herein. Other compositions include two or more of the chromogenic conjugates described herein, e.g., exactly two chromogenic conjugates (that is, two types of chromogenic molecules, rather than exactly two molecules) or exactly three chromogenic conjugates, or exactly four chromogenic conjugates.

The compositions may comprise one or more solvents, salts, detergents, and other components. In different embodiments the chromogenic composition may further comprise one or more or the following: (i) an organic modifier; (ii) an enzyme enhancer; (iii) an iron chelator; (iv) a detergent; (v) an anti-microbial agent; (vi) organic or inorganic salt; (vii) an enzyme substrate, e.g. peroxidase substrate. The list of additives to the chromogenic composition is not limiting, and any compound that is capable of enhancing or attenuating the performance of the present chromogenic conjugates as peroxidase substrates or chromogenic molecules is contemplated as a part of the composition depending on embodiment of its use.

In some embodiments, the chromogenic composition or medium may comprise any liquid solvent, preferably aqueous solvent (water), where the chromogenic conjugate is initially soluble but capable of reacting to form an insoluble precipitate at the site of peroxidase activity. The liquid solvent may comprise a primary solvent such as water and an organic cosolvent such as NMP or 2-pyrrolidone. The liquid solvent can comprise a buffer with a suitable buffering capacity, for example, phosphate buffered saline (PBS), Tris buffer, and/or imidazole buffer. The composition can be a buffered aqueous solution that has a pH in the range from 3 to 9, alternatively from about 3 to about 6, alternatively about 4 to about 7, alternatively about 5 to about 8.

In some embodiments, the chromogenic composition or medium may comprise an organic or inorganic salt. The inorganic salt may be selected from the group consisting of sodium chloride, magnesium chloride, potassium chloride, calcium chloride, sodium phosphate, or ammonium sulfate, and combinations thereof. The organic salt may be selected from sodium acetate, ammonium acetate or imidazole salts, for example, imidazole hydrochloride, or others. The concentration of salt may range from approximately $10^{-3}$ M to saturation, for example, from approximately 20 mM to approximately 200 mM, or from approximately 25 mM to approximately 100 mM. In some embodiments, the media may comprise salt in a concentration of approximately 10 mM, 20 mM, 50 mM, 75 mM or 100 mM.

In some embodiments the chromogenic composition may comprise a detergent, for example, polyethylenglycol-p-isooctyphenyl ether (NP-40) or a surfactant, for example, selected from the surfactants based on polyoxyethylene sorbitan monolaurate (Tween), or a surfactant based on block copolymers (pluronic etc.) or others. The amount of the detergent may vary from about 0.001% to about 5%, either v/v or w/v.

In some embodiments, an organic modifier may be present in the composition in an amount from about 1% to about 20% (v/v or w/v), however, in some embodiments higher concentrations of the organic modifier may be required. The organic modifier may for example be polyethylene glycol (PEG). Other examples include but are not limited to organic modifiers selected from the group consisting of C1-C4 alcohols, N-Methyl pyrrolidone (NMP), dimethylsulphoxide (DMSO), mono- and diethylene glycol, sulpholane, N,N-dimethylformamide (DMF) and combinations thereof. In some embodiments it may be advantageous to use polyethylene glycol (PEG), for example, PEG2000, or propylene glycol. The amount of polyethylene glycol or other organic modifier in the composition may vary from about 0.1% (v/v) to about 20% (v/v), for example from about 1% (v/v) to about 15% (v/v), such as 5-10% (v/v).

By the term "enzyme enhancer" is meant any compound which enhances the catalytic activity of a peroxidase. Such enzyme enhancers may be selected from the group consisting of phenylboronic acid derivatives and divalent metal ions such as nickel or calcium. The amount of the enzyme enhancer may vary from about $10^{-7}$ to about $10^{-3}$ M.

Examples of an iron chelator include ethylene diamine tetra acetic acid (EDTA) or ethylene diamine hydroxyl phenylacetic acid type chelator (EDHPA). Concentration of the iron chelator may vary from about $10^{-9}$ to about $10^{-6}$ M.

The chromogenic composition can be provided as a stable solution. The term "stable" in the present context means that the capability of the chromogenic composition to serve as reaction media for the peroxidase-mediated conjugate deposition and of the chromogenic conjugate(s) to maintain substantially the same spectral characteristics remain substantially unchanged during substantial periods of time; such as the compositions may be prepared and kept for at least 4 hours at room temperature before the use. The compositions may also be prepared and preserved for longer periods of time, such as from 12 hours to 12 months, or for longer periods of time. To prolong the shelf-life of the chromogenic composition, it may be useful to store the composition at temperatures below 20° C., for example, at 4-10° C., and/or to add to the composition an anti-microbial compound. The anti-microbial compound may be any anti-microbial compound commonly used with chromogenic compounds.

The concentration of the chromogenic conjugate in the composition may vary from about $10^{-9}$ M to about $10^{-2}$ M, depending on the nature of the method of use. For example from about $10^{-5}$ M to about $10^{-3}$ M, such as from about $10^{-4}$ M to about $10^{-3}$ M.

In some embodiments, the chromogenic composition may also comprise a peroxide compound. For example the medium can include hydrogen peroxide ($H_2O_2$) e.g., at a concentration of 0.0002% to 0.04%, or from around 0.5 mM to around 1.5 mM. In some embodiments, when the chromogenic composition comprises a peroxide compound, stability of the composition may be reduced, such as to 1-2 week's storage without changing the features discussed above.

In some embodiments, the present compositions are substantially free of peroxidase substrates other than the peroxidase substrate moieties of the chromogenic conjugates of the present disclosure and peroxide compound.

As mentioned above, in some embodiments, the present compositions may comprise a detergent. In some preferred embodiments, the detergent is a nonionic, non-denaturing detergent. In some embodiments, the composition comprises from 0.001% to 10% detergent, alternatively 0.01% to 1%, alternatively 0.05% to 0.5%.

In some embodiments, a two-component formulation is provided as a kit or used in a method. A first component comprises a chromogenic conjugate as described herein in a buffer with a lower pH (such as pH of 4 to 5, e.g., pH 4.8) to avoid hydrolysis over time. The second component is a buffered solution of hydrogen peroxide with a higher pH (such as a pH of 7-8, e.g., pH 7.4). The two components when mixed form a working solution having an intermediate pH (such as a pH of 6-7, e.g., pH 6.8). Such a two component formulation can be mixed by instrument or manually and can have a shelf life of +2 years at cold room temperature. The formulation has 3 week stability when mixed together at room temperature.

In some embodiments, the chromogenic composition comprises an organic cosolvent, e.g. 2-10% v/v organic co-solvent, which has been found to yield a staining intensity which is significantly enhanced. Suitable organic co-solvents are 2-pyrrolidone and NMP.

Methods of Use

As another aspect, methods are provided for using the chromogenic conjugates described herein and compositions comprising those conjugates in various analyses, techniques and steps where a sample, tissue, or portions thereof are stained or dyed. For example, the present chromogenic conjugates are useful for detection of molecular targets, such biological or chemical molecules, molecular structures, etc, in samples using a host of experimental schemes for detecting and visualizing such targets, for example. immunohistochemistry (IHC), in situ hybridization (ISH), ELISA, Southern, Northern, and Western blotting. Generally, the present chromogenic conjugates may be used in any analysis in which DAB has been used as stain for visualization of targets. Compared to conjugates described in WO2009/036760, WO2010/094283, WO2010/094284, WO2011/047680 and WO2012/143010, the present chromogenic conjugates do not demand the presence of a cross-linker such as DAB, ACHC or ferulic acid to mediate precipitation of the conjugates from chromogenic described above in the presence of peroxidase. The chromogenic conjugates can be used for detection of molecular targets in solid or semi-solid samples or targets that are immobilized onto or into solid supports, such as a microscopic slide, nitrocellulose membrane, microarray chip, gel, and other supports.

For example, the present chromogenic conjugates can be used to stain or dye Formalin Fixed Paraffin Embedded (FFPE) tissue samples, metaphase spreads or histological smears. The present chromogenic conjugates can be used in immunohistochemical analytical methods, where a protein of interest is detected or identified by color. The present chromogenic conjugates can be used in chromogenic in situ hybridization (CISH), where a nucleic acid of interest is detected or identified by color.

The present methods are carried out by linking a target with a molecule or moiety peroxidase activity, typically Horse Radish Peroxidase (HRP) or fragments having the enzymatic activity, then subsequently catalyzing the formation of an insoluble colored precipitate at the location of the target from any of the soluble chromogenic conjugates described herein.

The present conjugates are superior to chromogens such as DAB for use with cells, tissues and other types of samples which have brown coloring. For example, melanomas are already brown by nature, as are many lung cancer specimens due to smoking or urban air pollution. For these samples, DAB is especially ill suited for staining specimens from patients afflicted with these two major types of cancers. Accordingly, as another aspect, methods are provided for staining specimens having a natural brown color by applying the present conjugates, particularly a red, yellow or blue chromogenic conjugate. In some embodiments, one, two, or more of the present chromogenic conjugates are contacted with a sample comprising a brown tissue, for example, a sample comprising lung cancer cells, melanoma cells, melanocytes, mole tissue, tonsil tissue, or liver tissue. Preferably the conjugate is Compound 2. The present conjugates can also advantageously be used for detection of multiple targets in a sample.

In the present methods, one or more binding agents may be applied to a sample before the present conjugates are applied to the sample. The term "binding agent" designates a molecule that is capable of direct or indirect binding to a target, wherein the term "directly" means that the binding agent has affinity to the target and is capable of recognizing the target and specifically binding to it, wherein the term "indirectly" means that the binding agent does not have specific affinity to the target but has affinity to a substance which is associated with the target and is capable of specifically binding to this substance. The binding agent which is capable of direct binding to a target is sometimes referred to as a "primary binding agent". A binding agent which is capable of indirect binding to a target is sometimes referred to as a "secondary binding agent". The primary binding agent is typically used to contact the sample. It may be comprised of any molecule which will specifically bind to the target supposedly present in the sample. The secondary binding agent may be any molecule that binds the primary binding agent. Detection systems employing the present conjugates for visualization of targets may comprise other binding agents, such as a tertiary or quaternary binding agents; the detection may include several primary binding agents directed to detect various targets in the sample, for example, two or more different molecules (such as two or more proteins, or a protein and a nucleic acid) or include several primary binding agent directed to detect the same target in the sample, e.g. multiple molecular probes detecting a gene of interest. The detection systems may also include several secondary binding agents, which may be molecules of same species, e.g. antibodies, or different species, e.g. antibody and nucleic acids.

In cases where the target does not inherently comprise peroxidase activity, at least one of the binding agents used to detect a target in the sample in the present visualization systems comprises a peroxidase activity in order to label the location of target in the sample with the peroxidase activity.

Use of the present conjugate molecules may be particularly advantageous in multiplexed methods where more than one target is to be stained or dyed. As described above, the present conjugate molecules have advantageous optical features that allow clear distinction between targets stained in different colors, both by observing the microscopic field of a stained sample, such as a histological sample, and analyzing a captured image of the stained sample. Another advantage is that the conjugates are substrates of the same enzyme, namely a peroxidase enzyme, such as HRP or SP. This significantly simplifies procedures for staining of multiple targets in samples, increases robustness of staining procedures, as one and the same protocol and the same reagents may be used for detection of the targets by employing different conjugates. It also makes the overall detection procedure less expensive and particularly suited for automated staining, imaging of stained samples and analyses of staining results.

The present methods and kits can comprise any binding agents capable of detecting a target in a solid sample or a target immobilized onto or into a solid support. For example, the binding agent can be an immune-specific binding pair such as an antibody and antigen, or a non-immune specific binding pair such as a nucleic acid probe and a complementary sequence, or another type such as biotin and avidin. Binding agents of various types are common general knowledge in the field, and descriptions of binding agents can be found in Q. Ashton Acton, ed., "Antigens—Advances in Research and Application: 2013 Edition", Scholarly Editions, or Ralph Raply, ed, "The Nucleic Acid Protocols Handbook", Humana Press.

Typically, in the present target detection methods, a sample comprising a target is sequentially incubated in one or more incubation media. The term "incubation medium" means in the present context an aqueous medium comprising particular compounds where a sample is maintained during a certain period of time (termed herein "incubation time") in order to allow a desirable reaction between the particular compounds of the solution and the sample taking place. The incubation media may be the media in which the target is naturally found by a binding agent ("binding agent media"), or it may be one of the present chromogenic compositions (such as those described in the above sections).

Time for maintaining and/or incubating the sample in an incubation medium, i.e. incubating time, may vary from approximately 3 seconds to overnight, for example, around 10 seconds, 20 seconds, 30 seconds, 1 minute, 2 minutes, etc., for example, 3-10 minutes, 10-20 minutes, 20-40 minutes, 40-60 minutes, 1-2 hours or longer, for example, overnight. In one embodiment, the incubating time at all steps of the detection procedure may have the same duration, i.e. every incubating may last 1 min, 2 min, 3 minutes, 5 minutes, 10 minutes, etc. The time may be selected based on the embodiment used. In another embodiment, the incubating time may vary from one step to another, for example, incubating the sample in a media comprising a binding agent may last from 1 minute to overnight, incubating the sample in a media comprising the chromogenic conjugate and a peroxide compound may last from 1 min to 15 minutes or longer.

Incubating may be performed in various temperature conditions, depending on the type of target, binding agent, conjugate, etc. The detection procedures are mainly temperature independent, however, if desired, the temperature may be used for regulating the duration of the incubating time, for example, lower temperatures may be used to prolong the incubating time, and, vice versa, higher temperatures may be used to shorten the time for incubating.

Basically, the binding agent media is a buffered aqueous solution of one or more binding agents that has pH in the range from 4 to 9. In some embodiments the first incubation media may comprise an organic or inorganic salt. The inorganic salt may be selected from for example, sodium chloride, magnesium chloride, potassium chloride, calcium chloride, sodium phosphate, or ammonium sulfate. The organic salt may be selected from for example, sodium acetate, ammonium acetate or imidazole salts, for example, imidazole hydrochloride, etc.

The amount of salt in binding agent media may range from approximately $10^{-3}$ M to saturation, for example, from approximately 20 mM to approximately 200 mM, or from approximately 50 mM to approximately 500 mM. In some embodiments, the media may comprise salt in the amount from approximately 10 mM to 500 mM. In other embodiments the medium may be free of salt.

As mentioned, typically, the pH value of binding agent media may vary from about 4 to about 9, such as between pH 3.5 and pH 9.5, for example, between pH 5 and pH 7, between pH 5.5 and pH 6.5 or between pH 6.5 and 7.5, or between pH 7 and pH 8, or between pH 7.5 and pH 8.5, or pH 8 and pH 9. Any buffer with a suitable buffer capacity may be used, for example, phosphate buffered saline (PBS) and imidazole buffer. Other suitable buffers may be found in Good, NE., et al (1966) Hydrogen ion buffers for biological research. Biochem. 5(2), 467-477. The pH value of the media may be essential for binding of binding agent to the target; it may be optimized depending on the nature of the binding agent and the target.

In some embodiments the binding agent media may comprise an organic modifier (by the term "organic modifier" is meant any non water solvent), for example, N-methyl pyrrolidone (NMP), dimethylsulphoxide (DMSO), mono- and diethylene glycol, sulpholane, N,N-dimethylformamide (DMF), polyethylene glycol (PEG), propylene glycol, etc. The amount of the organic modifier may vary from around 1% to around 20% (v/v or w/v), or, in some embodiments, be higher than 20%.

In some embodiments the binding agent media may comprise a detergent, for example, polyethyleneglycol-p-isooctyphenyl ether (NP-40) or a surfactant for example, selected from the surfactants based on polyoxyethylene sorbitan monolaurate (Tween), or a surfactant based on block copolymers (pluronic etc.), etc. The amount of the detergent may vary from about 0.001% to about 5% v/v or w/v). In some embodiments the binding agent media may comprise a stabilizing agent for the binding agent, for example, bovine serum albumin or dextran. The amount of the stabilizing agent may vary from 0.01% to 20% (w/v).

In some embodiments the binding agent media may comprise an ion chelator (for example, ethylene diamine tetra acetic acid (EDTA) or ethylene diamine hydroxyl phenylacetic acid type chelator (EDHPA), etc.). The amount of the chelator may vary from about $10^{-9}$ M to about $10^{-6}$ M.

In some embodiments, the binding agent media may comprise one or more blocking agents for saturating non-specific binding sites, i.e. sites of the solid support that do not comprise the target. Some non-limiting examples of blocking agents suitable for different embodiments may be the Denhard's solution, bovine serum albumin, skimmed milk, etc.

Because a great variety of species of targets, binding agents and assay formats are contemplated, the composition of the binding agent media may vary and may be adjusted for particular embodiments using the knowledge of the art.

The present methods also comprise one or more wash steps before or after incubation of a sample using a washing media, for example, between the step of incubation of the sample with a binding agent and the step of staining the sample with one or more of the present chromogenic conjugates. Typically, a washing medium will be a medium of the same or similar composition as one that has been used for incubating or otherwise treating the sample in the step preceding the washing step, wherein the washing media lacks the active ingredient, i.e. a particular agent of the incubation step, for example, a binding agent, a conjugate molecule, etc.

The present methods may comprise one or more steps of incubating of the sample in a medium that would quench any undesirable peroxidase activity, e.g. endogeneous peroxidase activity in the sample or residual peroxidase activity associated with the target site. Typically, incubating of the sample in a peroxidase activity quenching medium will precede a step of incubating of the sample with a binding agent, or, in case of detection of several targets in a sample, it will take place after the first target is visualized with a first conjugate and before incubation of the sample with a second binding agent directed to a second target. A peroxidase activity quenching medium would typically comprise an amount of a peroxide compound, such as hydrogen peroxide. The amount of a peroxide compound in the medium may vary from 1% to 10% (v/v or w/v).

The present methods and uses include assays of various formats in which the present chromogenic conjugates are employed. In general, the assays where the conjugates may be used are any of those where DAB can be used. Some non-limiting embodiments of such assay formats are described below.

Target or biomarkers may be present in cells or tissues, and they can be detected employing the methods described herein in any suitable assay format, for example in ImmunoHistoChemistry (IHC), or chromogenic in situ hybridization (CISH), or ELISA.

In some embodiments, the target may be a protein, e.g. a cellular membrane receptor or a cytoplasmic protein, in other embodiments, the target may be a nucleic acid, e.g. a cytoplasmic nucleic acid. Derivatives of any latter mentioned targets, e.g. fragments, precursors, mutants of target proteins or nucleic acids, etc. may also be targets in some embodiments.

Thus, in various embodiments, the target may be a biological or chemical target molecule, or a particle, or a molecular or cellular complex, or molecular or cellular structure, or a virus, or a microorganism, or a fragment of said target molecule, particle, complex, structure, virus or microorganism. Among targets contained in chemical and environmental samples may be different pollutants, toxins, warfare substances, members of molecular libraries, industrial noxious waste compounds, etc.

In some embodiments, the biological sample may be a suspension of cells or a tissue section. Target molecules or structures of cells in suspension may be detected using ELISA, IHC or CISH. When ELISA, IHC or ISH are used for the detection cells of the suspension are to be attached to a solid support, for example, ELISA plate or slide.

Preparation and process steps for cells, tissues or other samples in IHC or CISH are common general knowledge in the field. For descriptions of various steps, see for example "Immunohistochemical Staining Methods", Dako IHC Guidebook, 6th Ed (2013); van der Loos, "User Protocol: Practical Guide to Multiple Staining", Cambridge Research & Instrumentation, Inc. (2009); "Immunohistochemistry (IHC) an Application Guide", Abcam, (2013); "Handbook of Practical Immunohistochemistry", Lin & Prichard ed. (2015); Immunohistochemistry and In Situ Hybridization of Human Carcinomas", Hayat ed. (2005).

In CISH, a sample is taken and exposed to a nucleic acid binding agent which hybridizes by virtue of complementary base pairing to the target nucleic acid. The target nucleic acid in the sample is typically denatured to expose binding sites. In the present assays, the binding agent has or is linked to a peroxidase enzyme, and one or more of the present chromogenic conjugates are thereafter contacted with the sample. The existence or amount of the target nucleic acid is detected by visual recognition of the chromogen manually or automatedly.

In IHC, a sample is taken and exposed to a binding agent such as an antibody or fragment thereof which specifically binds a target molecule such as a cell surface protein. In the present assays, the binding agent has or is linked to a peroxidase enzyme, such as via a secondary antibody, and one or more of the present chromogenic conjugates are thereafter contacted with the sample. The existence or amount of the target molecule is detected by visual recognition of the chromogen manually or automatedly.

In the present assays, a light microscope, often referred to as optical microscope, uses visible light and a system of lenses to magnify images of small samples containing the chromogenic conjugate. Bright-field microscopy is a simple optical microscopy illumination technique. The sample is illuminated by white light, and contrast in the sample is caused by absorbance of some of the transmitted light in dense areas of the sample. The typical appearance of a bright-field microscopy image is a chromogenically colored sample on a bright background.

Automated staining and visualization devices may be used in various embodiments of the present methods, for example for the detection of multiple biological markers. Detection of multiple markers frequently requires balancing of the signals derived from the different chromogenic moieties. Automated staining devices are known in the field and the methods may be adapted for these devices.

In automated methods of analysis, computer-controlled automatic test equipment is used to evaluate the stained samples, using computations to derive quantitative measurements from an image. High-performance charge-coupled device (CCD) cameras can be used for visualizing the chromogenically stained samples having one or more colored precipitates. Image acquisition can be coupled with advanced widefield microscopes and various algorithms for image restoration. Color separation can be obtained using three-CCD devices (3CCD) and a dichroic beam splitter prism that splits the image into red, green and blue components. Each of the three CCDs is arranged to respond to a particular color.

The methods of analysis described herein can include some or all of the following steps: (a) collecting a first tissue or cell sample from an individual diagnosed with or suspected of having a cancer, particularly lung cancer cells, melanoma cells, or liver cancer cells; (b) applying a binding agent for a target, wherein the binding agent has peroxidase activity; (c) staining the first tissue or cell samples with one or more of the present chromogenic conjugates; (d) measuring the optical density of the stained tissue or cell samples from step (c), wherein the stained tissue or cell samples are illuminated with light having a wavelength absorbed by the one or more chromogenic conjugates.

In some embodiments, the present methods are for detecting a target in a sample, for example, an object with peroxidase activity, biological marker, etc, wherein said target or sample is immobilized onto a solid support, wherein the methods comprise steps of (a) incubating a sample supposedly comprising target with one or more binding agents comprising peroxidase activity, wherein said one or more binding agents is/are capable of direct or indirect binding to the target and forming a complex comprising the target and one or more binding agents having peroxidase activity; (b) incubating the sample in a solution comprising one or more of the present chromogenic conjugates; (c) detecting the deposited chromogenic conjugate, and thereby detecting the target.

Yet another aspect of the present disclosure, a method for staining a sample by mixing chromogenic conjugates of the present disclosure with other chromogens. For example, Rhodamine 6G-L12-Cou can be mixed with a fluorescein chromogen to produce a yellow/orange color. This combination is favorable because no single chromogen produces a suitable orange color. Additionally, rhodamine derivatives such as rhodamine 101 derivatives are expensive and chemically troublesome. A chromogen producing a yellow color will be considered weak to the human eye since yellow chromogens based on fluorescein have sharp upper absorbance peaks and absorb little green light, even in high concentration/intense stains. In other words, the yellow color does not change; they remain yellow. On the other hand, yellow dyes with broader absorbance extending weakly into the green absorbance range exhibit dichroism, meaning they produce two colors. In low concentration, these dyes appear yellow since they absorb blue light well; in higher concentrations, the color shifts towards red as green light is absorbed. Therefore, by mixing a green absorbing Rhodamine 6G with a yellow dye, the mixture can yield a designer dichromic dye, where hue changes slightly with intensity to yield an extended dynamic range of color contrast.

Compound 2 alone produced stains that changed from bright magenta at low intensities toward more full reds at higher intensities. In a mixture containing 0.6 mM of compound 2 in 15 mM imidazole, pH 6.8, 4% NMP, 0.1% NP40-Nonidet (octylphenoxypolyetheneoxyethanol), 0.01% Benzalkonium chloride, 0.03% hydrogen peroxide, the mixture is characterized by matching DAB in intensity in the low range by equal staining of low expression targets. Conversely, this mixture never overstains even the highest intensity targets. This can be seen when using various primary antibodies and various types of tissue samples.

As shown above, various dichroic stains of the present disclosure can be made by mixing two or more chromogenic conjugates of the present disclosure. The dichroic effect depends on very high absolute absorbance at the dominant wavelength that saturates the eye and instruments used to observe the dichroic effects of stained samples. If the dominant chromogen is magenta, as in compound 2, then at some point of increasing intensity there must be essentially no perception of green light left for humans or even instruments. Unexpectedly, it was found that 4 µm thick sections of tissue samples could be stained with a single dichroic chromogen so intensely that a color change would be observed by the human eye. So it was theorized that a change from Magenta towards purple would be especially agreeable, since the hue change would be perceived as harmonic and gradual and the by using compound 2 and 32, that neither absorb blue, the colors would stay bright. Another assumption, a reflection on the brownish precipitates produced by chromogens that appear orange in solution, was a dichroic bright orange with an absorbance minimum around 505 nm composed of a greenish-yellow chromogen and again a magenta chromogen. Therefore, it should be appreciated that dichroic chromogens provide an expanded dynamic range; as one channel of information dries out, (i.e. all light of one color is already absorbed at medium intensities) then absorbance of light at other wavelengths begins at higher intensities; thus, producing a color change.

Two useful dicroic stains were produced: a dichroic orange stain that turns red at high intensities and a dichroic red stain that turns bluish purple at high intensities. These compounds have expanded dynamic range, having a more distinct cut-off with respect to intensity and color change.

The dichroic orange stain was made in the following manner: in 50 mM imidazole, pH 6.8, 10% NMP, 0.1% NP40—Nonidet (octylphenoxypolyetheneoxyethanol), 0.01% Benzalkonium chloride, 0.03% hydrogen peroxide 1 mM compound 9 and 0.2 mM compound 2 produced a dichroic orange of good intensity with clear colors. The color change was from pale, slightly salmon orange at low intensities over vibrant deep oranges at medium intensities towards extremely bright reds at the highest intensities. This is valuable since no chromogen alone produces a good orange color when staining tissue, and it is an excellent contrast color to hematoxylin. The dichroic effect is a further aid in determining intensity differences. The degree of color change is moderate since the local shallow minimum is only 72 nm wide but the key point is that this minimum is around 505 nm. The dichroic stain absorbs blue light well and green light very well, yet matches the human color receptors with a drop right in the middle of the tipping point. Hence the bright and vibrant colors look much more pleasing and clear to the eye than single orange chromogens. This dichroic chromogen was measured in water at pH 6.8 and has a local shallow minimum between 459 and 531 nm, 72 nm wide and a global minimum with essentially no absorbance above 575 nm.

The dichroic red stain was made in the following manner: in 50 mM imidazole, pH 6.8, 10% NMP, 0.1% NP40-Nonidet, 0.01% Benzalkonium chloride, 0.03% hydrogen peroxide 1 mM compound 2 and 0.2 mM compound 35 produced an intense, and radically changing, color. The color change was from feeble magenta over bright red at low intensities. At medium intensities the color shifted towards distinctly reddish purple ending in deep bluish purple at the highest intensities. This shift was very clear on Her2 control cell lines. Because of the high intensity even some +0 cells were weakly stained and +1 cells appeared bright red. +2 cells were stained distinctly reddish purple and +3 cells dark bluish purple.

Another striking example was produced by staining tonsils with either antiCD21 or antiCD20. CD21 is an archetypical low expression marker whereas CD20 marks one of the most abundant proteins.

In liver tissue stained with cytokeratin, close range dramatic color changes could be observed between very low expression membranes that were feeble, yet distinctly magenta, and very high expression ductal structures with color changing to intense red to deep purple.

Areas with technical tissue defects as folds that produce increased absorbance demonstrated the ultimate color change towards bluish black. When measured in water at pH 6.8, this composition has a local shallow minimum between 532 nm and 642 nm, 110 nm wide and a global minimum with essentially no absorbance below 460 nm.

The dichroic effect demonstrated by these dichroic chromogens and stains provides an expanded dynamic range. Additionally, for those dichroic conjugates where a cut off in intensity is supported by a change of color, those conjugates provides a distinct method of staining targets. In some embodiments, a chromogenic HRP substrate conjugate is provided that has at least one local minimum at least 50 nm wide and a global minimum between 390 and 700 nm measured in water between pH 6 and 8.

Although the present conjugate molecules are described with respect to their chromogenic properties, it is also contemplated that the conjugate molecules can be used as fluorescent molecules in assays and methods that detect fluorescence.

As yet another aspect, conjugates are disclosed which provide fluorescence Forster Resonance Energy Transfer (FRET) within the conjugate. These FRET conjugates have two different chromogenic moieties that absorb and emit light at different wavelengths (maxima), and the radius of interaction is smaller than the wavelength of light emitted. An excited (first) chromogenic moiety emits energy that is absorbed by a receiving (second) chromogenic moiety, which then emits light at a different wavelength. For FRET conjugates, the distance and angle between the two chromogenic moieties affects the energy transfer, so it is desirable to fix the distance and angle, at least so any rotation or flipping around bonds is much slower than in photochemical reactions. In the present FRET conjugates, the emission of the first chromogenic moiety and the absorbance of the second chromogenic moiety should overlap, as increased overlap yields better energy transfer and better fluorescence.

A suitable FRET conjugate was prepared by reacting the piperazine amides of Rhodamine 6G with carboxy-fluorescein (shown below as Formula XV):

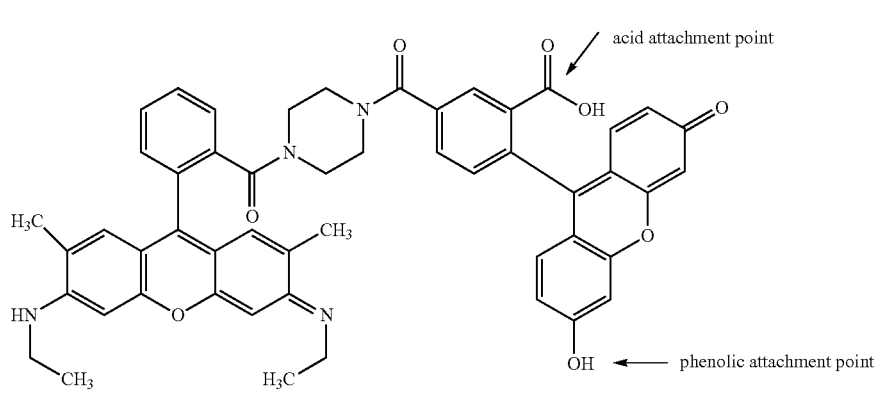

Formula XV

Another FRET conjugate was prepared by reacting Rhodamine B with carboxy-fluorescein. Both FRET conjugates were fluorescent, and both were capable of Forster Resonance Energy Transfer. Both of these FRET conjugates absorb light at the maxima of the fluorescein moiety but emit different light at the emission maxima of the rhodamine 6G and rhodamine B moieties.

In some embodiments, a FRET conjugate according to Formula XIVa, where $R^{38}$ is piperazine or another 5- to 6-membered ring.

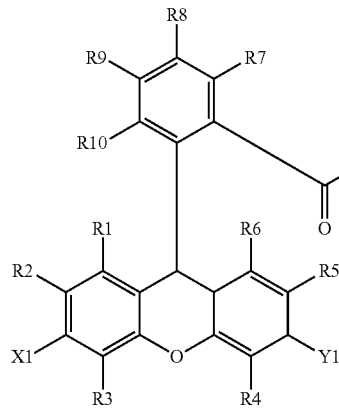
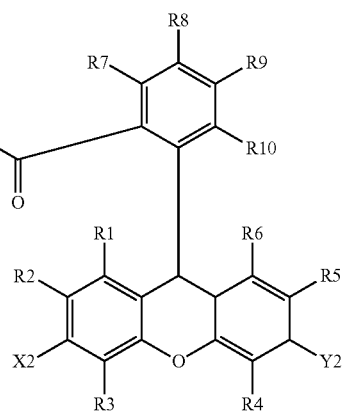

To be capable of FRET, the two chromophores must be close, yet not touch. It is contemplated there will not be energy transmission between such chromophores if a flexible linker is used between them, since a flexible linker would allow them to come into contact; a piperazine ring provides adequate distance and rigidity, and other 4- to 8-membered cyclic or heterocyclic groups are expected to also provide adequate distance and rigidity. The effect is that the fluorescence of the carboxy-fluorescein moiety is transferred to the rhodamine moiety. While these chromogenic moieties retains two excitation maxima, corresponding to their performance as stand-alone fluorophores, a single emission maxima corresponding to the rhodamine moiety is observed.

The Rhodamine B-carboxyfluorescein conjugate can be excited at 500 nm and emits at 585 nm. The present FRET conjugates are extremely useful since they allow several fluorophores to be excited at the same wavelength, yet be detected at different wavelengths. It is contemplated that the present FRET conjugates can be used in multiplexed flow cytometry and in DNA sequencing. These are structurally similar rigid back-to-back fluorescein-rhodamine conjugates that are further attached to nucleotide triphosphates. Additional description of dye terminators based on FRET can be found in US2005/0255475.

The drawback is that the quantum yield is limited. This is consistent with FRET theory: The distance and angles of the two compounds are identical but the overlap smaller between fluorescein and Rhodamine B than between fluorescein and Rhodamine 6G. But the conjugates are intensely fluorescent.

It is contemplated that the Rhodamine B-carboxy-fluorescein conjugate could potentially be a long-sought fourth color for fluorescence microscopy, namely a blue emitting fluorophore. FITC (fluorescein) has been used to provide a green emission or signal, and Rhodamines or CyDyes have been used to provide a red emission or signal, but in practice it is difficult to obtain a yellow fluorophore without unacceptable spill-over of the yellow signal into the green or red signals. This is has limited the use of yellow fluorescent signals. Typically infra-red emitting fluorophores are used as a fourth color, but they have the disadvantage of not being visible to the human eye. A FRET conjugate based on Rhodamine B and carboxy-fluorescein would also be visible with a set excitation and emission filters for red fluorophores. By using a green excitation filter and a red emission filter, only the FRET fluorophore would be visible. Digital image processing can be used to subtract the FRET image from the red image to show the desired red signal.

A linker to a peroxidase substrate may be attached to the FRET conjugates at an acid attachment point or a phenolic attachment point, as shown in Formula XV above. It is contemplated that it will be preferable to attach a linker to the acid position, provided such attachment can be made (see drawing) without eliminating FRET capability. Additionally, as chromogens, these conjugates have highly desirable properties; for example, the 6G compound is orange while the Rhodamine B analogue is true red. These findings emphasize the potential value of the Rhodamine piperazine amides, as their colors and FRET capabilities are unexpected and beneficial.

Kit-of-Parts

A kit-of-parts comprising any of the present chromogenic conjugates or compositions comprising thereof is described herein for detecting a target in a sample. For example, a kit-of-parts can include one or more of the conjugates set forth below as embodiments A1 to A19 or K1 to K5 or in the Examples, alternatively two, three, four or more of those conjugates, in a single composition or container or in separate compositions or containers.

Because the present methods are suitable for detection of a huge variety of targets in a variety samples in a variety assay formats, kits-of-parts may comprise many different items, however all kits-of-parts comprise a chromogenic conjugate, either in a solid form (powder, lyophilized, etc.) or as a composition comprising a chromogenic conjugate molecule or an incubation medium comprising a chromogenic conjugate molecule as described herein. The following are some non-limited exemplary embodiments of a kit-of-parts.

In one embodiment, the kit-of-parts may comprise: (i) a chromogenic conjugate as described herein, either in a solid form (powder, lyophilized, etc.) or in a liquid medium; and (ii) one or more binding agents capable of direct or indirect binding to a target, wherein binding agents may be any binding agents described herein.

In another embodiment the kit-of parts may comprise: (i) a solution of a first chromogenic conjugate as described in the present disclosure, wherein the first conjugate has first spectral characteristics; (ii) a solution of a second chromogenic conjugate as described in the present disclosure, wherein the second chromogenic conjugate has one or more spectral characteristics that are different from one or more spectral characteristics of the first chromogenic conjugate.

Either of the first or the second conjugate can be one of the conjugates set forth below as embodiments A1 to A19 or K1 to K5 or in the Examples.

The present kit-of parts may comprise several parts (1, 2, 3, 4, 5, 6 or more) which are solutions of different chromogenic conjugates as any of the defined above, wherein each of the different conjugates has distinct spectral characteristics that are different from spectral characteristics of the other conjugates that are included in the kit.

In another embodiment the kit-of parts as any of the above may further comprise one or more binding agents capable of direct or indirect binding to a target, wherein binding agents may be any binding agents described herein.

In another embodiment the kit-of parts as any of the above may further comprise instructions for use of the chromogenic conjugate, staining interpretation and/or scoring guidelines.

In other embodiments the kit-of parts as any of the above may further comprise one or more of the following: an aqueous composition comprising DAB, ACHC or another peroxidase substrate; a binding agent capable of specifically binding to the chromogenic detectable label of the conjugate; protocols for staining, visualization and/or quantification of targets; one or more reference materials, e.g. a sample comprising a stained target; an additional stain, e.g. histological stain or a substrate solution for another than peroxidase enzyme; mounting media; incubation media, washing media, etc.

In another embodiment, the kit-of-parts may comprise (i) any of the items or all items of the above embodiments; (ii) means for visualization of targets and/or image capture, or a reference to such means; (iii) software for controlling the instruments; (iv) software for image analysis; (iv) locked image analysis algorithms.

Composition of the present kit-of-part may be designed to suit any of the applications described above of the present chromogenic conjugates.

Methods of Manufacture

As one aspect of the present disclosure, methods for making the present chromogenic conjugates is provided. Such methods are demonstrated in the Examples which follow.

As another aspect of the present disclosure, a highly efficient method for making piperazine amides of rhodamines is provided. Reaction between rhodamines and 2-haloacetylesters yields 2'-alkylcarboxymethyl derivatives of formula IV:

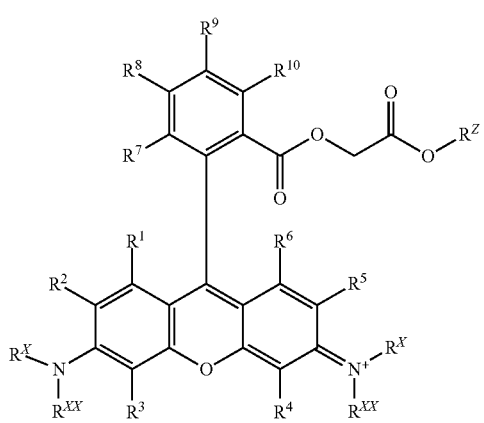

Formula IV where $R^1$ to $R^{10}$, $R^X$, $R^{XX}$, $R^z$, X and Y have the definitions set forth herein.

These 2'-alkylcarboxymethyl derivatives react smoothly with a moderate excess of piperazine at around 100° C. in anhydrous solvents such as acetonitrile or N-methyl pyrrolidone to give the corresponding piperazine amides of the general formulas V or Va, which are useful as intermediates for synthesizing a chromogenic conjugates, as well as being chromogens.

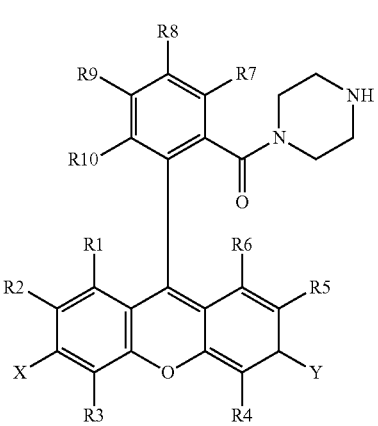

Formula V

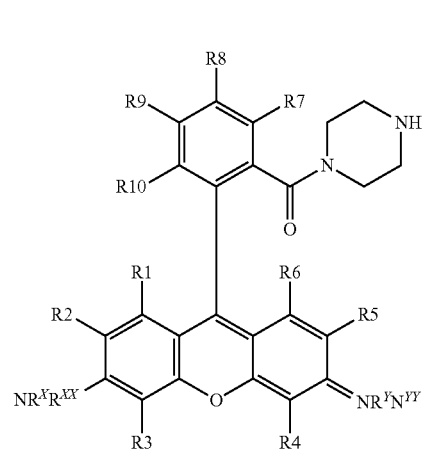

Formula Va where $R^1$ to $R^{10}$, $R^X$, $R^{XX}$, $R^Y$ and $R^{YY}$ have the definitions set forth herein. Excess piperazine was removed by evaporation under reduced pressure and following a precipitation step with diethyl ether the piperazine amides could be isolated in high yield and purity, and no formation of rhodamine dimers was observed.

As another aspect of the present disclosure, methods for making secondary amides of rhodamine, fluorescein and derivatives thereof are provided. Reaction between secondary amines and various esters of rhodamine yield secondary amides of rhodamine. For example, the esters of Formula VII or Formula VIIa (which is rhodamine B) can be reacted with amines to produce amides of rhodamines.

Formula VII

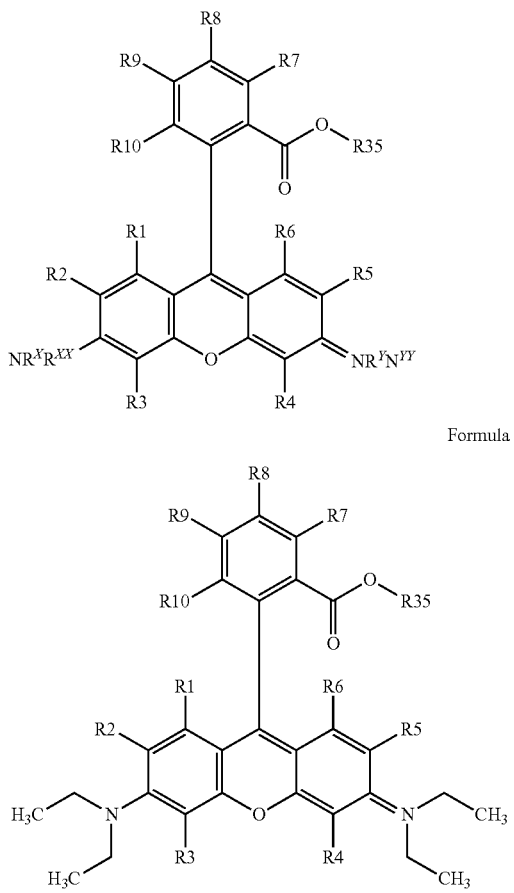

Formula VIIa where R³⁵ can be one of the following compounds 33R1-33R9:

R1, R2, R3, R4 structures

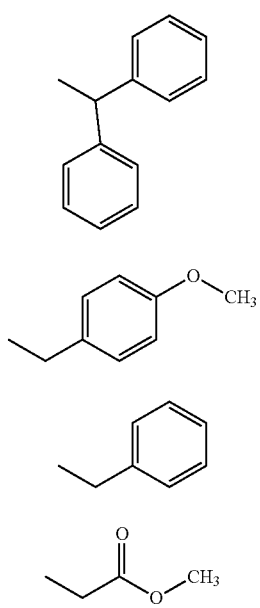

R5, R6, R7, R8, R9 structures

Compounds 33R1-33R9 and in Formula VIIa, $R^1$ though $R^{10}$ preferably are H. Various esters of Formula VIIa (rhodamine B) are listed from 33R1 to 33R9 were tested for reactivity with a secondary amine, and they are listed in order of increasing reactivity with those secondary amines, where $R^1$ is the least reactive of compounds 33R1 and 33R9 is the most reactive of compounds 33R1-33R9. 33R1 and 33R2 reacted slightly or did not react with secondary amines. It is possible that reactivity can be enhanced by stabilizing a cationic leaving group. The benzyl ester, 33R3, showed low, but some reactivity. The alkyl-carboxyl-methyl derivatives 33R4, 33R5, and 33R6 reacted more strongly with secondary amines. However, 33R4 and 33R5 were more prone to side reactions (i.e., hydrolysis), and 33R6 reacted slightly more slowly. The 4-nitrobenzylic ester, 33R7, reacted with secondary amines but was also more prone to hydrolysis, whereas the ethyl-carboxy-methyl ester, 33R8, reacted suitably. 33R8 is prepared from rhodamine B and 2-bromoethylacetate. 33R8 remains stable up to around 140° C. overnight. Derivatives like 33R9 are equally stable and evidently a preferred or suitable precursor to the final chromogens of the present disclosure. Compounds such as rhodamine B with ester 33R8 or 33R9 are stable. They are slightly active esters because they include a β-carbonyl group, yet the β-carbonyl group is a suitable leaving group to allow a secondary amine to react with these rhodamine B conjugates.

As another aspect of the present disclosure, methods for making secondary amides of rhodamine are provided. Reaction between rhodamine esters, such as the esters of Compounds 33R1-33R9, and various secondary amines yields secondary amides of rhodamine. The various secondary amines can be one of the following compounds 34A to 34L, alternatively compounds 34G to 34L, alternatively compounds 34J to 34L, alternatively compounds 34G to 34I:

34A
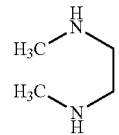

34B
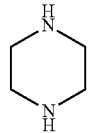

34C

34D
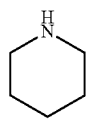

34E
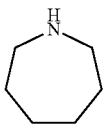

34F
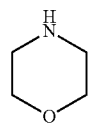

34G
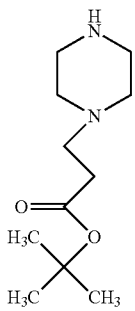

34H
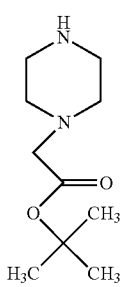

34I
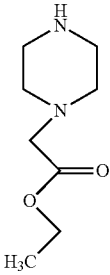

34J

34K
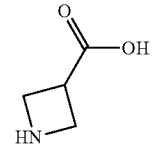

34L
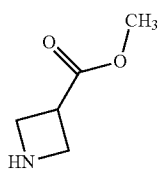

The secondary amines can be a piperazine, piperidine, pyrrolidine, imidazolidine, pyrazolidine, azetidine, or other 4- to 8-membered (alternatively 5- to 7-membered) cyclic or heterocyclic group, optionally with an amine, a carboxyl or an ester substituent.

It is surprising and unexpected that piperazine (Compound 34B) reacts with these esters (which are only slightly active), and that N,N'-dimethyl ethylenediamine (Compound 34A) react also. Further experiments demonstrated that compounds 34C-L were also surprisingly reactive with these esters. Compounds 34A-L are listed in order of experimental (or expected) reactivity with the esters, from most reactive to least reactive, where compound 34A is the most reactive and compound 34L is expected to be the least reactive. Compound 34A, N,N'-dimethyl ethylenediamine, is an alternative to piperazine and absorbs at 531 nm, which is the same absorbance as the esters. Upon reaction with a rhodamine, the secondary amines 34B, 34C, 34D, 34E, and 34F will not undergo a further reaction useful for preparing a conjugate having a peroxidase substrate linked to it. It was observed that reactivity dropped sharply from the 5 ring of 34C to the 7 ring of 34E and that the Rhodamine 6G derivative of 34C had absorbance (533 nm) in between β-carbonyl esters (531 nm) and other secondary amides (535 nm). Therefore, it is contemplated that 34L would react in a similar manner. 34G, 34H and 34I also reflect an effort for a carboxylic acid derivative of a secondary amide of rhodamines, and 34G reacts acceptably. It is contemplated that the positive trend in reactivity would continue with azetidine compounds such as 34J, 34K and 34L. In particular, a compound such as 34K or 34L, which comprise aziridine-3-carboxylate, are contemplated as reacting to form useful synthesis precursors, which in turn can comprise a novel family of desirable rhodamine carboxylic acid derivatives. 34G, 34H and 34I also respond to a need for a carboxylic acid derivative of a secondary amide of rhodamines that reacts sufficiently.

Thus, it has unexpectedly been found that the reactivity between similar secondary amines and β-carbonyl esters of rhodamines can differ by orders of magnitude. In some instances, steric hindrance appears to be affecting reactivity. Furthermore, this can affect the stability of these secondary amides that appear exceptionally unstable towards aqueous base, hence the use of acid labile tert-butyl protection groups on compounds 34G and 34H. This lability/reactivity also extends to β-carbonyl esters that easily hydrolyze.

As another aspect of the present disclosure, methods for making secondary amides of rhodamines is disclosed. Reaction between a β-carbonyl ester of the rhodamine and a secondary amine yields a secondary amide of rhodamine of the general formula VIII:

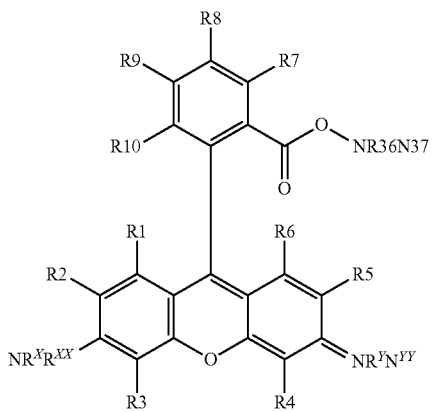

Formula VIII where $R^1$ to $R^{10}$ are as defined herein, but preferably are H, and preferably substituted with (alkyl) carboxylic acid or ester. In some embodiments, $R^{36}$ or $R^{37}$ includes an additional amine (which may be protected), a carboxyl or an ester. In some embodiments, $R^{36}$ and $R^{37}$ can form piperazine, piperidine, pyrrolidine, imidazolidine, pyrazolidine, azetidine, or other 4- to 8-membered (alternatively 5- to 7-membered) cyclic or heterocyclic group, optionally with an amine, a carboxyl or an ester substituent. These secondary amides can be prepared on any scale and are purified by crystallization. Less reactive derivatives that do not include further functional groups can be used as chromogens; as they combine color and fluorescence with stable and static chemical structures, these are suitable as dyes, inks, paints, lasers, LEDs and in other compositions and uses.

Yet another aspect is a method to stain a tissue sample for the absence of a target. It has been recognized that if a certain portion of a tissue is stained with a chromogen of the present disclosure or DAB, then the portion of the tissue cannot be stained with a different color, unless the first stain is very weak and the second stain is very intense. It should be appreciated that it is possible to make a double stain of co-localized targets in mixed colors.

However, in such case of co-localized targets, the first chromogen reduces the number of antigens available for recognition by the second antibody and also reduces the number of the first primary antibodies (not recognized by HRP visualization in the first step) that might be visualized in a different color in the second step.

This effect can be performed to stain for the absence of a target such as a marker. This was observed on in using two of the present chromogenic conjugates to stain colon carcinomas. Colon tissue is normally positive for Cytokeratin 18. Colon tissue was stained using a method comprising staining cytokeratin 18 with a chromogenic conjugate of a first color, then staining with a second chromogenic conjugate of a second color to stain all cytokeratins in the colon tissue. For example, the first and second chromogenic conjugate may precipitate at the same binding agent, and they may contact the colon tissue simultaneously or sequentially. Alternatively, this may be accomplished by having two different binding agents, one of which is specific for cytokeratin 18, ant the other is pan-specific for cytokeratin (both normal colon and carcinomas are positive for cytokeratins), wherein a first of the two chromogenic conjugates precipitates at a first binding agent and a second of the two chromogenic conjugates precipitates a second binding agent. After staining colon carcinoma tissue with first and second chromogenic conjugates of distinct colors, it was observed that in many carcinomas, small areas were identified by the second chromogenic conjugate, in that they were stained in the second color. If the carcionomas were stained in the first color only, these areas could easily be overlooked and the sample could incorrectly be deemed negative for Cytokeratin 18, even though the absence of a stain could have been caused by many factors, such as air bubbles during staining, necrotic tissue, bad fixation, or another cause. Thus, the technical effect of the second stain is that it positively confirms the absence of cytokeratin 18, indicating for example that the cells have been mutated and lost their ability to produce cytokeratin 18. It is known that colon carcinomas undergo such mutations. Therefore, this method of staining allows one to use first and second chromogenic conjugates to identify carcinomas that have such mutations.

Yet another aspect of the present disclosure is Compound 22 (Formula XIa) and other compounds of Formula XI:

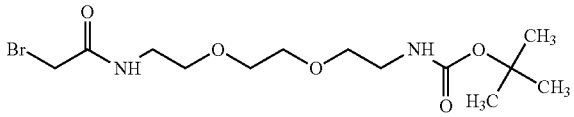

Formula XIa

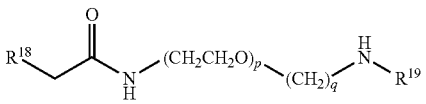

Formula XI wherein $R^{18}$ is a halogen; $R^{19}$ is a nitrogen atom protecting group (such as tert-butyloxycarbonyl (BOC) group; p is 0 to 4; and q is 0 to 4. Reaction between Compound 22 and rhodamines can provides rhodamine derivatives of the general formula VI:

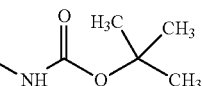

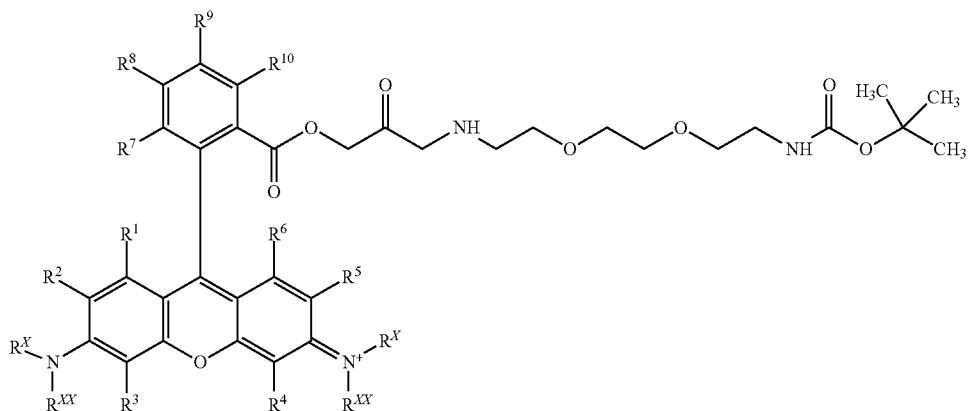

Similar rhodamine derivates can be prepared with other compounds according to formula XI.

In anhydrous solvents at approximately 100° C., the reactions run to completion with virtually no formation of any byproducts. In a single step these reactions provide rhodamine derivatives with enhanced water solubility, an extended linker an aa suitably protected primary amino group, that following deprotection with TFA may be reacted with HRP substrates to provide efficient chromogenic HRP substrates in just three steps.

Over twenty different chromogens were prepared from compound 22. Compound 22 reacted with the relatively lowly reactive native carboxylic acid group of every rhodamine and fluorescein tested. It reacted with the phenolic oxygens on fluorescein too. It reacted readily and selectively with piperazine amides of fluorescein and rhodamines. And as illustrated in formula X, compound 22 reacted with the phenolic group in Patent Blue V, next to two sulfonic acid groups.

Similarly, compound 22 or other compounds of Formula IX can be reacted with fluorescein to provide fluorescein derivatives.

REPRESENTATIVE EMBODIMENTS

A1. A chromogenic conjugate comprising (a) a chromogenic moiety, and (b) a peroxidase substrate moiety, wherein the chromogenic moiety and the peroxidase substrate moiety are linked together via a linker, wherein the conjugate is a compound of formula I:

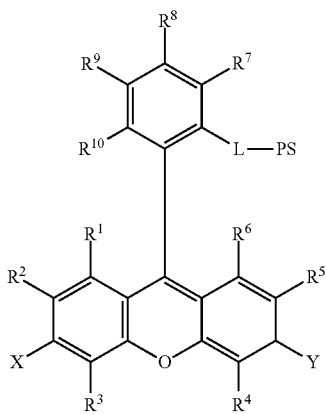

where X is —OH, —OR$^X$ or —NR$^X$R$^{XX}$,
where Y is =O or =N$^+$R$^Y$R$^{YY}$;
wherein R$^1$, R$^2$, R$^3$, R$^4$, R$^5$, R$^6$, R$^7$, R$^8$, R$^9$, R$^{10}$, R$^X$, R$^{XX}$, R$^Y$, and R$^Y$ are independently selected from hydrogen and a substituent having less than 40 atoms;
L is the linker which a compound comprising a chain of at least 5 consecutively connected atoms, such as 5 to 29 consecutive atoms; and
PS is a peroxidase substrate moiety. For example, in one embodiment X is —OH, —OR$^X$, and Y is =O. In another embodiment X is —NR$^X$R$^{XX}$, than the Y is =N$^+$R$^Y$R$^{YY}$.

A2. The chromogenic conjugate of the embodiment A1, wherein
R$^1$ is selected from hydrogen, R$^{11}$, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different R$^{13}$ or suitable R$^{14}$ groups, or alternatively, R$^1$ may be taken together with R$^2$ to form part of a benzo, naptho or polycyclic aryleno group which is optionally substituted with one or more of the same or different R$^{13}$ or suitable R$^{14}$ groups;
R$^2$ is selected from hydrogen, R$^{11}$, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different R$^{13}$ or suitable R$^{14}$ groups, or alternatively, R$^2$ may be taken together with Rt, to form part of a benzo, naptho or polycyclic aryleno group which is optionally substituted with one or more of the same or different R$^{13}$ or suitable R$^{14}$ groups, or alternatively, when X is —NR$^X$R$^{XX}$, R$^2$ may be taken together with R$^X$ to form a 5- or 6-membered ring which is optionally substituted with one or more of the same or different R$^{13}$ or suitable R$^{14}$ groups;
R$^X$, when present, is selected from hydrogen, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different $R^{13}$ or suitable $R^{14}$ groups, or, alternatively, $R^X$ may be taken together with $R^2$ to form a 5- or 6-membered ring which is optionally substituted with one or more of the same or different $R^{13}$ or suitable $R^{14}$ groups;

$R^{XX}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^{XX}$ may be taken together with $R^3$ to form a 5- or 6-membered ring which is optionally substituted with one or more of the same or different $R^{13}$ or suitable $R^{14}$ groups;

$R^3$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, when X is $-NR^XR^{XX}$, $R^3$ may be taken together with $R^{XX}$ to form a 5- or 6-membered ring which is optionally substituted with one or more of the same or different $R^{13}$ or suitable $R^{14}$ groups;

$R^4$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, when Y is $-N^+R^YR^{YY}$, $R^4$ may be taken together with $R^{yy}$ to form a 5- or 6-membered ring which is optionally substituted with one or more of the same or different $R^{13}$ or suitable $R^{14}$ groups; $R^{yy}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively $R^{yy}$ may be taken together with $R^4$ to form a 5- or 6-membered ring which is optionally substituted with one or more of the same or different $R^{13}$ or suitable $R^{14}$ groups;

$R^Y$, when present, is selected from hydrogen, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^Y$ may be taken together with $R^5$ to form a 5- or 6-membered ring optionally substituted with one or more of the same or different $R^{13}$ or suitable $R^{14}$ groups;

$R^{YY}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^{XX}$ may be taken together with $R^6$ to form a 5- or 6-membered ring which is optionally substituted with one or more of the same or different $R^{13}$ or suitable $R^{14}$ groups;

$R^5$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^5$ may be taken together with $R^6$ to form part of a benzo, naptho or polycyclic aryleno group which is optionally substituted with one or more of the same or different $R^{13}$ or suitable $R^{14}$ groups, or, alternatively, when Y is $-N^+R^YR^{YY}$, $R^5$ may be taken together with $R^y$ to form a 5- or 6-membered ring optionally substituted with one or more of the same or different $R^{13}$ or suitable $R^{14}$ groups;

$R^6$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, or, alternatively, $R^6$ together with $R^5$ may form part of a benzo, naptho or polycyclic aryleno group which is optionally substituted with one or more of the same or different $R^{13}$ or suitable $R^{14}$ groups;

$R^7$, $R^8$ and $R^9$ are each, independently of one another, selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups;

$R^{10}$ is selected from selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or suitable $R^{14}$ groups and (C6-C40) arylalkyl or heteroaryl alkyl optionally substituted with one or more of the same or different $R^{13}$ or suitable $R^{14}$ groups, halo, haloalkyl, $-OR^{12}$, $-SR^{12}$, $-SOR^{12}$, $-SO_2R^{12}$, and nitrile;

$R^{11}$ is selected from $-NR^{15}R^{15}$, $-OR^{16}$, $-SR^{16}$, halo, haloalkyl, $-CN$, $-NC$, $-OCN$, $-SCN$, $-NO$, $-NO_2$, $-N_3$, $-S(O)R^{16}$, $-S(O)_2R^{16}$, $-S(O)_2OR^{16}$, $-S(O)NR^{15}R^{15}$, $-S(O)_2NR^{15}R^{15}$, $-OS(O)R^{16}$, $-OS(O)_2R^{16}$, $-OS(O)_2NR^{15}R^{15}$, $-OP(O)_2R^{16}$, $-OP(O)_3R^{16}R^{16}$, $-P(O)_3R^{16}R^{16}$, $-C(O)R^{16}$, $-C(O)OR^{16}$, $-C(O)NR^{15}R^{15}$, $-C(NH)NR^{15}R^{15}$, $-OC(O)R^{16}$, $-OC(O)OR^{16}$, $-OC(O)NR^{15}R^{15}$ and $-OC(NH)NR^{15}R^{15}$;

$R^{12}$ is selected from (C1-C20) alkyls or heteroalkyls optionally substituted with lipophilic substituents, (C5-C20) aryls or heteroaryls optionally substituted with lipophilic substituents and (C2-C26) arylalkyl or heteroarylalkyls optionally substituted with lipophilic substituents;

$R^{13}$ is selected from hydrogen, (C1-C8) alkyl or heteroalkyl, (C5-C20) aryl or heteroaryl and (C6-C28) arylalkyl or heteroarylalkyl;

$R^{14}$ is selected from —$NR^{15}R^{15}$, =O, —$OR^{16}$, =S, —$SR^{16}$, =$NR^{16}$, =$NOR^{16}$, halo, haloalkyl, —CN, —NC, —OCN, —SCN, —NO, —$NO_2$, =$N_2$, —$N_3$, —S(O)$R^{16}$, —S(O)$_2R^{16}$, —S(O)$_2OR^{16}$, —S(O)$NR^{15}R^{15}$, —S(O)$_2NR^{15}R^{15}$, —OS(O)$R^{16}$, —OS(O)$_2R^{16}$, —OS(O)$_2NR^{15}R^{15}$, —OS(O)$_2OR^{16}$, —OS(O)$_2NR^{15}R^{15}$, —C(O)$R^{16}$, —C(O)$OR^{16}$, —C(O)$NR^{15}R^{15}$, —C(NH)$NR^{15}R^{15}$, —OC(O)$R^{16}$, —OC(O)$OR^{16}$, —OC(O)$NR^{15}R^{15}$ and —OC(NH)$NR^{15}R^{15}$;

each $R^{15}$ is independently hydrogen or $R^{16}$, or alternatively, each $R^{15}$ is taken together with the nitrogen atom to which it is bonded to form a 5- to 8-membered saturated or unsaturated ring which may optionally include one or more of the same or different additional heteroatoms and which may optionally be substituted with one or more of the same or different $R^{13}$ or $R^{16}$ groups;

each $R^{16}$ is independently $R^{13}$ or $R^{13}$ substituted with one or more of the same or different $R^{13}$ or $R^{17}$ groups; and each $R^{17}$ is selected from —$NR^{13}R^{13}$, —$OR^{13}$, =S, —$SR^{13}$, =$NR^{13}$, =$NOR^{13}$, halo, haloalkyl, —CN, —NC, —OCN, —SCN, —NO, —$NO_2$, =$N_2$, —$N_3$, —S(O)$R^{13}$, —S(O)$_2R^{13}$, —S(O)$_2OR^{13}$, —S(O)$NR^{13}R^{13}$, —S(O)$_2NR^{13}R^{13}$, —OS(O)$R^{13}$, —OS(O)$_2R^{13}$, —OS(O)$_2NR^{13}R^{13}$, —OS(O)$_2OR^{16}$, —OS(O)$_2NR^{13}R^{13}$, —C(O)$R^{13}$, —C(O)$OR^{13}$, —C(O)$NR^{13}R^{13}$, —C(NH)$NR^{15}R^{13}$, —OC(O)$R^{13}$, —OC(O)$OR^{13}$, —OC(O)$NR^{13}R^{13}$ and —OC(NH)$NR^{13}R^{13}$.

A3. The conjugate of any of embodiments A1 and A2, wherein $R^1$, $R^2$, $R^3$, $R^4$, $R^5$, $R^6$, $R^7$, $R^8$, $R^9$, and $R^{10}$, are independently selected from —H, -halogen, -methyl, -ethyl, -propyl, -isopropyl, -vinyl, —$SO_3H$, —$PO_3H$, —$NO_2$, —COOH, —$NH_2$, —CN, —OH, —OMe and —OEt.

A4. The conjugate of any of the embodiments A1-A3, wherein the chromogenic moiety is selected from the group consisting of rhodamines and fluoresceins, and salts thereof.

A5. The conjugate of any of the embodiments A1-A4, wherein one or more of the chromogenic moiety is selected from the group consisting of rhodamine, rhodamine 6G, tetramethylrhodamine, rhodamine B, rhodamine 101, rhodamine 110, fluorescein, and O-carboxymethyl fluorescein.

A6. The conjugate of any of the embodiments A1-A5, wherein the moiety is selected from rhodamine 116, rhodamine 123, rhodamine 19.

A7. The conjugate of any of the embodiments A1-A6, wherein the moiety is a rhodamine salt and comprises an anion selected from Cl$^-$, Br$^-$, TFA$^-$, and ClO$_4^-$.

A8. The conjugate of any of the embodiments A1-A7, wherein the chromogenic moiety is a 2'-piperazine amide derivative.

A9. The conjugate of any of the embodiments A1-A8, wherein $R^{10}$ is selected from the group consisting of alkyl, heteroalkyl, alkoxy, halo, haloalkyl, amino, alkylthio, cyano, isocyano, cyanato, mercaptocyanato, nitro, and sulfinyl.

A10. The chromogenic conjugate of any of embodiments A1 to A9, wherein the chromogenic conjugate is selected from the molecules shown in Table 1 and salts of the =N moiety.

A11. The conjugate according to any of embodiments A1-A10, wherein the peroxidase substrate moiety has the following formula:

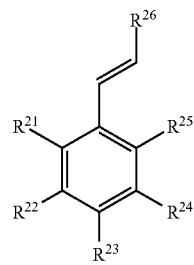

Formula II $R_{21}$ is —H, $R_{22}$ is —H, —O—X, or —N(X)$_2$;

$R_{23}$ is —OH;

$R_{24}$ is —H, —O—X, or —N(X)$_2$;

$R_{25}$ is —H, —O—X, or N(X)$_2$;

$R_{26}$ is —CON—(X)$_2$, —CONH(X), or COO(X);

wherein H is hydrogen; O is oxygen; N is nitrogen; and X is H, alkyl or aryl or a bond with L.

A12. The conjugate according to any of embodiments A1 to A11, wherein $R^{23}$ is —OH, and $R_{24}$ is —H.

A13. The conjugate according to any of embodiments A1 to A12, wherein either $R_{21}$ or $R_{25}$ is —OH, $R_{22}$ and $R_{24}$ are —H, and $R^{23}$ is —OH.

A14. The conjugate according to any of embodiments A1 to A13, wherein the peroxidase substrate is a residue of ferulic acid, cinnamic acid, caffeic acid, sinapinic acid, 2,4-dihydroxycinnamic acid or 4-hydroxycinnamic acid (coumaric acid).

A15. The conjugate according any of embodiments A1 to A14, wherein the linker is a compound that comprises 1 or 2 repeats of Formula III:

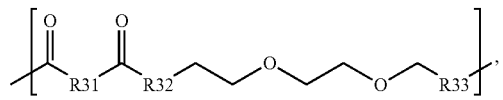

Formula III wherein $R^{31}$ is selected from methyl, ethyl, propyl, OCH$_2$, CH$_2$OCH$_2$, (CH$_2$OCH$_2$)$_2$, NHCH$_2$, NH(CH$_2$)$_2$, CH$_2$NHCH$_2$, cycloalkyl, alkyl-cycloalkyl, alkyl-cycloalkyl-alkyl, heterocyclyl (such as nitrogen-containing rings of 4 to 8 atoms), alkyl-heterocyclyl, alkyl-heterocyclyl-alkyl, and wherein no more than three consecutively repeating ethyloxy groups, and $R^{32}$ and $R^{33}$ are independently elected from NH and O.

A16. The conjugate of any of the embodiments A1-14, wherein the linker is selected from:

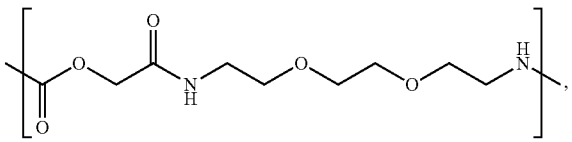

Formula IIIa

-continued

Formula IIIb

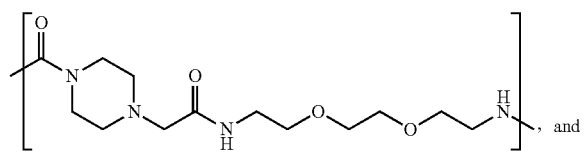
, and

Formula IIIc

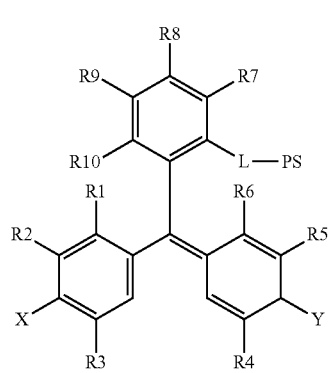

A17. A chromogenic conjugate according to Formula IX:

Formula IX

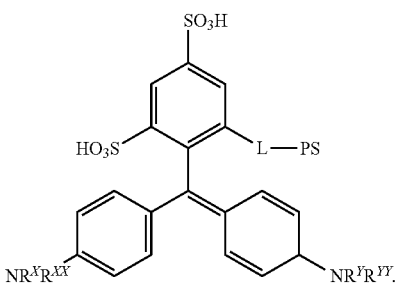

where X is —OH, —OR$^X$ or —NR$^X$R$^{XX}$,
where Y is =O or =N$^+$R$^Y$R$^{YY}$;
wherein R$^1$, R$^2$, R$^3$, R$^4$, R$^5$, R$^6$, R$^7$, R$^8$, R$^9$, R$^{10}$, R$^X$, R$^{XX}$, R$^Y$, and R$^{YY}$ are independently selected from hydrogen and a substituent having less than 40 atoms;

L is a linker comprising a linear chain of 5 to 29 consecutively connected atoms; and
PS is a peroxidase substrate moiety.

A18. The conjugate of embodiment A17, wherein the conjugate has the structure of Formula IXa:

Formula IXa

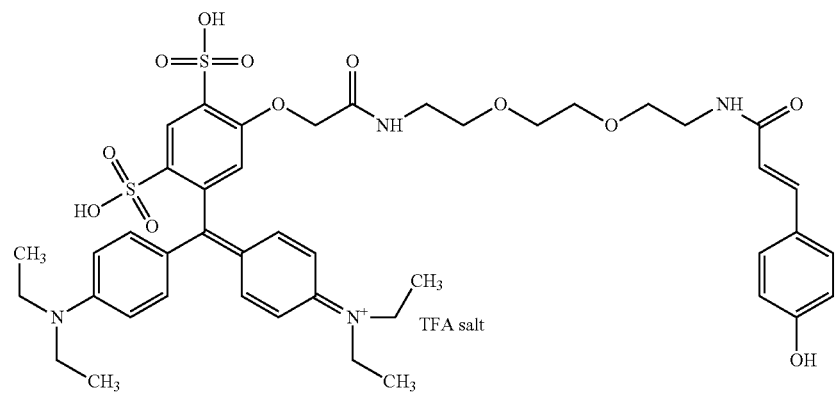

A19. The conjugate of embodiment A17, wherein the conjugate has the structure of Formula IXb:

Formula IXb

B1. A kit for detection of a target having peroxidase activity or linked to a peroxidase enzyme in a sample, the kit comprising at least one solution of a chromogenic conjugate according any of the foregoing embodiments or embodiments K1 to K5 or any of the conjugates of the Examples. The term "having peroxidase activity" means that the target either has an inherent peroxidase activity or a peroxidase activity which is chemically linked to the target, i.e. via a chemical bond, e.g. a target that does not have an inherent peroxidase activity is processed and chemically coupled to a peroxidase activity; the term "linked" in the present context means that a peroxidase activity is indirectly associated with the target, e.g. via a target binding agent that comprises/has a peroxidase activity, e.g. an antibody/nucleic acid probe-HRP conjugate.

B2. A kit according to embodiment B1, wherein the kit comprises two or more aqueous solutions, wherein each solution comprises a chromogenic conjugate according to any embodiment of the embodiments A1 to A19 or K1 to K5, wherein chromogenic conjugates of each of the two or more solutions differ from each other by one or more of their spectral characteristics.

B3. A kit according to embodiment B1, wherein the solution comprises at least two chromogenic conjugates of embodiments A1 to A19 or K1 to K5.

C1. A method for detection of a target in a sample by chromogenic detection, comprising:
- (i) incubating a sample supposedly comprising a target in an aqueous solution, wherein the target comprises peroxidase activity or the target is directly or indirectly linked to a peroxidase enzyme, wherein the aqueous solution comprises:
  - a) at least one (alternatively at least two, alternatively at least three, alternatively at least four, and/or no more than four, three or two) chromogenic conjugate according to any of embodiments A1 to A19 or K1 to K5,
  - b) a peroxide compound,
  at a time and temperature sufficient to form a colored precipitate of the chromogenic conjugate; and
- (ii) detecting the colored precipitate of the chromogenic conjugate in the sample, thereby detecting the target in the sample.

C2. The method of embodiment C1, wherein the colored precipitate is detected using a light microscope.

C3. The method of any of embodiments C1-C2, wherein the colored precipitate is detected by visual observation by a human observer.

C4. The method of any of embodiments C1-C3, wherein the colored precipitate is detected by an automated imager.

C5. The method according to any of embodiments C1-C4, wherein the aqueous solution comprises 0.001% to 0.005% hydrogen peroxide and between 0.1 mM and 10 mM of the at least one chromogenic conjugate.

C6. The method according to any of embodiments C1-C5, wherein the amount of the at least one chromogenic conjugate is from about 0.01 mM to about 10 mM, such as from about 0.05 mM to about 5 mM, such as from about 0.2 to about 2 mM, such as from about 0.4 to about 1 mM.

C7. The method according to any of embodiments C1-C6, wherein the peroxidase activity is associated with horse radish peroxidase.

C8. The method according to any of embodiments C1-C7, wherein horse radish peroxidase is directly or indirectly linked to the target.

C9. The method according to any of embodiments C1-C8, wherein the target is a polypeptide, nucleic acid, carbohydrate, lipid or a derivative thereof, molecular complex, particle, eukaryotic or prokaryotic cell or microorganism.

C10. The method according to any of embodiments C1-C9, wherein the sample is a biological sample, environmental sample, or chemical sample.

C11. The method according to embodiment C10, wherein the sample is immobilized onto a solid support.

C12. The method of any of embodiments C1-C11, further comprising directly or indirectly linking the target to an antibody linked to a peroxidase enzyme.

C13. The method of any of embodiments C1-C12, comprising one or more additional steps, such as a washing step; a step of quenching undesirable peroxidase activity; a step of incubating a sample with one or more additional binding agents, e.g. a binding agent capable of binding to another target in the same sample, or a binding agent capable of binding to the chromogen of a chromogenic conjugate.

C14. The method of any of embodiments C1-C13, wherein the sample comprises at least two different targets, or at least two different sub-populations of the same target, wherein the at least two targets or at least two different subpopulations of the same target comprise peroxidase activity or are directly or indirectly linked to a peroxidase enzyme, comprising
- (i) incubating the sample in an aqueous solution, wherein the aqueous solution comprises:
  - a1) a first chromogenic conjugate according to any of embodiment A1 to A19 or K1 to K5;
  - b1) a peroxide compound,
  at a time and temperature sufficient to form a colored precipitate of the fist chromogenic conjugate;
- (ii) incubating the sample (i) in an aqueous solution, wherein the aqueous solution comprises:
  - a2) a second chromogenic conjugate according to any of embodiment A1 to A19 or K1 to K5;
  - b2) a peroxide compound,
  at a time and temperature sufficient to form a colored precipitate of the second chromogenic conjugate; wherein the first chromogenic conjugate has a first chromogenic characteristic and the second chromogenic conjugate has a second chromogenic characteristic, and wherein the first and second chromogenic characteristics have one or more different spectral characteristics;
  - (iii) optionally, incubating the sample with further aqueous solutions of chromogenic conjugates to stain a third, a fourth, etc. target in the sample, wherein the further aqueous solutions comprise chromogenic conjugates that have chromogenic characteristics that allow distinguishing staining of the first, second, third, fourth, etc targets from each other by color;
  - (iv) detecting the first, second, third, fourth, etc. target, by detecting the colored precipitate of the corresponding chromogenic conjugate in the sample.

C15. The method according to any of embodiments C1-C14, wherein the peroxidase activity is linked to the target(s) via a target specific binding agent(s) comprising peroxidase enzyme, such as one or more HRP moieties.

C16. The method according to any of embodiments C1-C15, wherein the target(s) is a protein(s) or nucleic acid(s).

C17. The method according to any of embodiments C1-C16, wherein the sample is stained manually, automatically or semi-automatically.

C18. The method according to any of embodiments C1-C17, wherein the staining is evaluated by image analysis.

C19. The method according to any of embodiments C1-C18 wherein the target is a nucleic acid, and incubating the sample produces a chromogenic in situ hybridization.

C20. The method according to any of embodiments C1-C19, wherein the method comprises detecting two or more targets by a procedure comprising the following steps:
- providing peroxidase activity at a first target in a sample;
- contacting the sample with a first chromogenic conjugate having a first color;
- forming a first colored precipitate at the first target;
- removing the peroxidase activity from the first target;
- removing non-precipitated first chromogenic conjugate from the sample;
- providing peroxidase activity at a second target in the sample;
- contacting the sample with a second chromogenic conjugate having a second color;
- forming a second colored precipitate at the second target; and detecting the first colored precipitate and the second colored precipitate, thereby detecting the first and second targets in the sample.

D1. A method for performing chromogenic in situ hybridization, said method comprising:
contacting a nucleic acid target with a probe that hybridizes with the nucleic acid target under hybridization conditions, wherein the probe comprises (1) a nucleic acid sequence at least partially complementary to the nucleic acid target and (2) a peroxidase enzyme or a first member of a specific binding pair; wherein the target and probe form a complex;
when the probe comprises (2), contacting the complex with a second member of the specific binding pair, wherein the second member of the specific binding pair is directly or indirectly linked to a peroxidase enzyme and specifically binds to the first member;
incubating the complex with at least one of the chromogenic conjugates according to any of embodiments A1 to A19 or K1 to K5, for a time and temperature sufficient to form a color precipitate at the target; and
detecting the color precipitate.

D2. The method of embodiment D1, wherein the first member of the specific binding pair is an antigen or hapten, and the second member is an antibody or antibody fragment.

D3. The method of any of embodiments D1 or D2, wherein the target nucleic acid is present in a nucleic acid duplex, and further comprising the step of denaturing the nucleic acid duplex.

D4. The method of any of embodiments D1-D3, further comprising the step of denaturizing with one or more FITC-labeled PNA probes.

D5. The method of any of embodiments D1-D4, further comprising counterstaining with a non-specific stain such as haematoxilin.

D6. The method of any of embodiments D1 to D5, further comprising one or more of the following steps: deparaffinizing; washing with buffer before the contacting step; stringent washing after hybridization; blocking of endogenous peroxidase; washing and dehydrating after the incubating step.

D7. The method according to embodiment D3, wherein the probe is a nucleic acid analog segment that comprises a peptide-nucleic acid (PNA) backbone.

E1. A method of deposition of a chromogenic conjugate according to any of embodiments A1 to A19 or K1 to K5, in a target site comprising a peroxidase activity, said method comprising incubating said target site in a solution comprising said chromogenic conjugate and a peroxide compound, and thereby depositing said conjugate molecule in said target site.

E2. The method according to embodiment E1, wherein the peroxidase activity is associated with horse radish peroxidase (HRP) present in the target site.

E3 The method according to embodiments E1 or E2, wherein the target site comprises a target and a peroxidase enzyme directly or indirectly linked to the target.

E4. The method according to any embodiments E1or E3, wherein the target site comprises a biological marker.

E5. The method according to any embodiments E1or E4, comprises depositing at least two chromogenic conjugates conjugate according to any of embodiments A1 to A19 or K1 to K5 at the target site.

F1. A method of detecting two or more targets in a sample, said method comprising:
providing peroxidase activity at a first target in a sample;
contacting the sample with a first chromogenic conjugate;
forming a first colored precipitate at the first target;
removing the peroxidase activity from the first target;
removing non-precipitated first chromogenic conjugate from the sample;
providing peroxidase activity at a second target in the sample;
contacting the sample with a second chromogenic conjugate;
forming a second colored precipitate at the second target; and
detecting the first colored precipitate and the second colored precipitate, thereby detecting the first and second targets in the sample,
wherein at least one of the first chromogenic conjugate or the second chromogenic conjugate is selected from any of the chromogenic conjugates according any of embodiments A1-A16, and wherein the first chromogenic conjugate and the second chromogenic conjugate have one or more spectral characteristics that are different from each other.

F2. The method of embodiment F1, wherein the method further comprises: removing the peroxidase activity from the second target; removing non-precipitated second chromogenic conjugate from the sample; providing peroxidase activity at a third target in the sample; contacting the sample with a third chromogenic conjugate having one or more spectral characteristics which are and different from one or more of the spectral characteristics of each of the first and second chromogenic conjugate.

F3. The method of any of embodiments F1 to F2, wherein each of the first chromogenic conjugate and the second chromogenic conjugate is a conjugate according to any of embodiments A1 to A19 or K1 to K5.

F4. The method of any of embodiments F1 to F3, further comprising the elements recited in any of embodiments C1-C13 or C15-C19.

G1. A chromogenic medium comprising: a chromogenic conjugate according to any of embodiments A1 to A19 or K1 to K5; a salt comprising an organic cation, anion or both; a nonionic, non-denaturing detergent; wherein the medium has a pH from about 3 to about 9.

G2. The medium of embodiment G1 wherein the organic salt is selected from salts of substituted and unsubstituted imidazoles, substituted and unsubstituted pyridines, substituted and unsubstituted pyrimidines, substituted and unsubstituted pyrazines, substituted and unsubstituted pyridazines, and tertiary and quaternary amines.

G3. The medium of embodiments G1 or G2, wherein the organic salt is an imidazole salt.

G4. The medium of embodiments G1, G2 or G3, wherein the detergent is 4-nonylphenyl-polyethylene glycol.

G5. The medium of any of embodiments G1-G4 wherein the pH is from about 3 to about 6, or about 4 to about 7, or about 5 to about 8.

G6. The medium of any of embodiments G1 to G5, wherein the medium comprises 1 mM to 100 mM imidazole, alternatively 10 mM to 75 mM, alternatively 15 mM, 20 mM, 25 mM, 30 mM, 35 mM, 40 mM, 45 mM, 50 mM, 55 mM, 60 mM, 65 mM, 70 mM imidazole.

G7. The medium of any of embodiments G1 to G6, wherein the medium comprises N-Methyl pyrrolidone (NMP) or pyrrolidone.

G8. The medium of any of embodiments G1 to G7, wherein the medium comprises 0.1 to 2 mM of a chromogenic conjugate, 10 to 50 mM imidazole, 1% to 10% NMP, and 0.01% to 1% octylphenoxypolyetheneoxyethanol.

H1. A method for making a secondary amide (such as piperazine amide) of a rhodamine, the method comprising:

reacting a 2'-alkylcarboxymethyl derivative according to Formula IV:

Formula IV

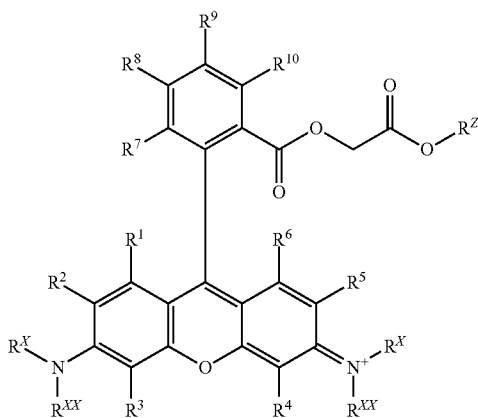

with an excess (preferably a moderate excess) of a secondary amine such as piperazine, at a suitable temperature (for example, from about 90° C. to about 110° C.) in an anhydrous solvent (such as acetonitrile or NMP) to form a secondary amide according to Formula Va:

Formula Va

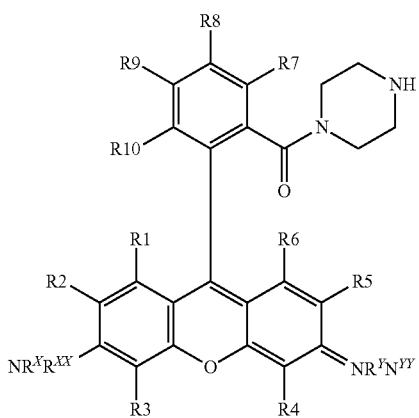

where $R^1$ to $R^{10}$, $R^X$, $R^{XX}$, $R^Y$ and $R^{YY}$ have the definitions set forth herein. Excess piperazine was removed by evaporation under reduced pressure and following a precipitation step with diethyl ether the piperazine amides could be isolated in high yield and purity, and no formation of rhodamine dimers was observed.

H2. The method of embodiment H1, wherein the 2'-alkylcarboxymethyl derivative and the secondary amine are reacted at a temperature of about 100° C. in acetonitrile or N-methyl pyrrolidone.

H3. The method according to embodiment H1 or H2, further comprising the steps of removing excess secondary amine by evaporation under reduced pressure and precipitating the secondary amide with diethyl ether. The secondary amide can be isolated in high yield and purity.

H4. The method of according to any of embodiments H1 to H3, wherein the secondary amide is substantially free of rhodamine dimers.

H5. The method of according to any of embodiments H1 to H5, further comprising producing the 2'-alkylcarboxymethyl derivative of Formula IV by a reacting a rhodamines and a 2-haloacetylester.

H6. The method according to any of embodiments H1 to H5, wherein the secondary amine is a piperazine, piperidine, pyrrolidine, imidazolidine, pyrazolidine, azetidine, or other 4- to 8-membered cyclic or heterocyclic group, optionally substituted with an amine, a carboxyl or an ester.

H7. The method according to any of embodiments H1 to H5, where the alkyl of the 2'-alkylcarboxymethyl derivative is selected from the group consisting of compounds 33R1 to 33R9, alternatively compounds 33R4 to 33R9, alternatively compounds 33R7 to 33R9.

H8. The method according to any of embodiments H1 to H5, where the secondary amine is selected from the group consisting of compounds 34A to 34L, alternatively compounds 34G to 34L, alternatively compounds 34J to 34L, alternatively compounds 34G to 34I.

I1. A method of staining a sample with a dichroic stain, said method comprising:

providing peroxidase activity at a first target in a sample;

contacting the sample with a first chromogenic conjugate at a first concentration (e.g., from 0.1 mM to 10 mM, or 1 mM), wherein the first chromogenic conjugate is selected from any of the chromogenic conjugates according any of embodiments A1 to A19 or K1 to K5;

forming a precipitate of the first chromogenic conjugate at the first target;

detecting a color of the precipitate;

measuring the target in the sample by the detected color, wherein a first detected color indicates a lower amount of the target, and a second detected color indicates a higher amount of the target.

I2. The method of embodiment I1, wherein the first chromogenic conjugate is Compound 2.

I3. The method according to any of embodiments I1 to I2, further comprising contacting the sample with a second chromogenic conjugate at a second concentration (e.g., from 0.03 mM to 10 mM, or 0.3 mM or 1 mM), wherein the first chromogenic conjugate and the second chromogenic conjugate have one or more spectral characteristics that are different from each other.

I4. The method according to any of embodiments I2 to I3, wherein the second chromogenic conjugate is selected from any of the chromogenic conjugate according any of embodiments A1-A16.

I5. The method according to any of embodiments I3 to I4, wherein the first chromogenic conjugate is Compound 9 and the second chromogenic conjugate is Compound 10.

I6. The method according to embodiment I5, further comprising contacting the sample with a third chromogenic conjugate at a third concentration (e.g., from 0.03 mM to 10 mM, or 0.3 mM or 1 mM), wherein the third chromogenic conjugate may be Compound 35.

I7. The method according to any of embodiments I3 to I4, wherein the first chromogenic conjugate is Compound 35 and the second chromogenic conjugate is Compound 10.

I8. The method according to any of embodiments I3 to I4, wherein the first chromogenic conjugate is Compound 5 and the second chromogenic conjugate is Compound 35.

J1. A compound of Formula XI:

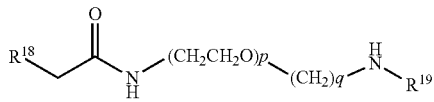
Formula XI wherein $R^{18}$ is a halogen; $R^{19}$ is a nitrogen atom protecting group (such as tert-butyloxycarbonyl (BOC) group; p is 0 to 4; and q is 0 to 4.

J2. The compound of embodiment J1, wherein $R^8$ is bromide; $R^{19}$ is a BOC group; p is 1 to 3; and q is 1 to 3.

J3. The compound of embodiment J2, having the structure of Formula XIa:

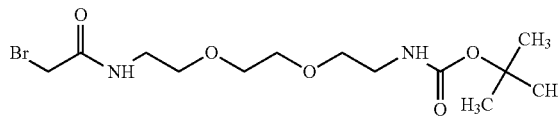
Formula XIa

J4. A method of making a chromogen comprising reacting a rhodamine (such as Rhodamine 6G or Rhodamine B), a fluorescein (such as fluorescein isothiocyanate, NHS-fluorescein, or O-carboxyfluorescein), or 2' ester or amide derivative or a a fluorescein, with a compound according to any of embodiments J1 to J3 to obtain an intermediate compound of Formula XII:

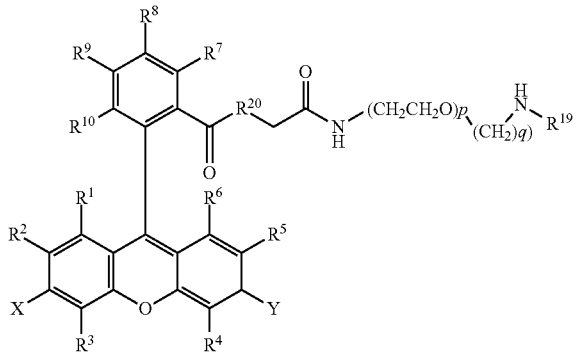
Formula XII where $R^{19}$ is a nitrogen atom protecting group (such as tert-butyloxycarbonyl (BOC) group; $R^{20}$ is O or NH; p is 0 to 4; and q is 0 to 4.

J5. An intermediate for synthesizing a chromogenic compound, wherein the intermediate is a compound according to Formula XII:

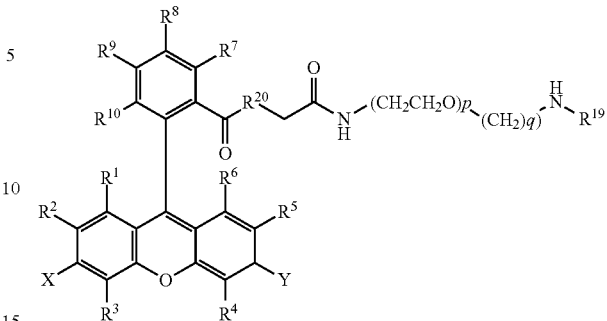
Formula XII where $R^{19}$ is a nitrogen atom protecting group (such as tert-butyloxycarbonyl (BOC) group; $R^{21}$ is O or NH; p is 0 to 4; and q is 0 to 4.

J6. An intermediate for synthesizing a chromogenic compound, wherein the intermediate is a compound according to Formula V or Va:

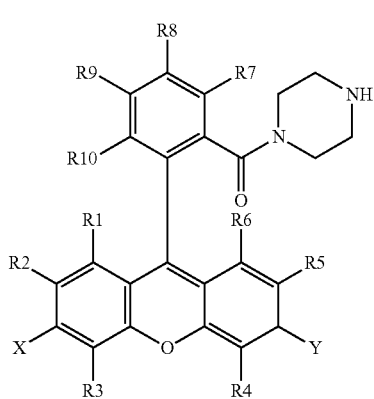
Formula V

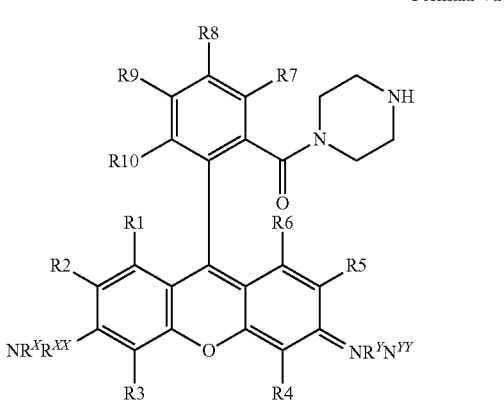
Formula Va where $R^1$ to $R^{10}$, $R^X$, $R^{XX}$, $R^Y$ and $R^{YY}$ have the definitions set forth herein.

J7. An intermediate for synthesizing a chromogenic compound, wherein the intermediate is a compound according to Formula XIII:

Formula XIII

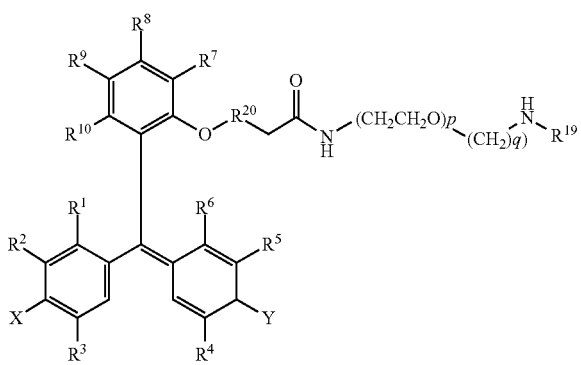

where $R^{19}$ is a nitrogen atom protecting group (such as tert-butyloxycarbonyl (BOC) group; $R^{20}$ is O or NH; p is 0 to 4; and q is 0 to 4.

J8. The intermediate of embodiment J7, wherein the intermediate is a compound according to Formula XIIIa:

Formula XIIIa

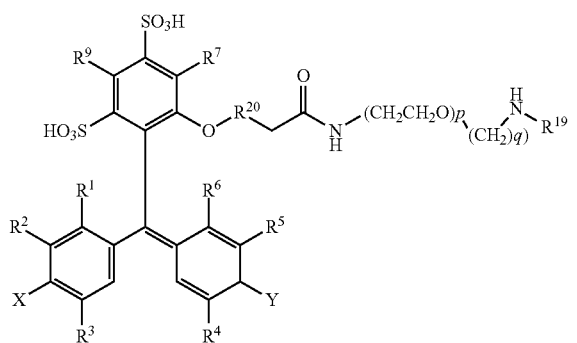

where $R^{19}$ is a nitrogen atom protecting group (such as tert-butyloxycarbonyl (BOC) group; $R^{21}$ is O or NH; p is 0 to 4; and q is 0 to 4.

K1. A conjugate having two chromogenic moieties according to Formula XIV:

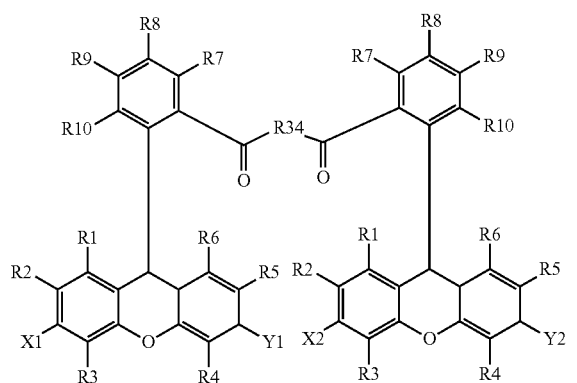

where X1 and X2 are selected from —OH, —OR$^X$ and —NR$^X$R$^{XX}$, and X1 and X2 are preferably different, where Y1 and Y2 are selected from =O or =N$^+$R$^Y$R$^{YY}$, and Y1 and Y2 are preferably different, wherein $R^1$, $R^2$, $R^3$, $R^4$, $R^5$, $R^6$, $R^7$, $R^8$, $R^9$, $R^{10}$, $R^X$, $R^{XX}$, $R^Y$, and $R^{YY}$ are independently selected from hydrogen and a substituent having less than 40 atoms, or are as defined elsewhere in the present disclosure; and where $R^{34}$ is selected from methyl, ethyl, propyl, OCH$_2$, CH$_2$OCH$_2$, (CH$_2$OCH$_2$)$_2$, NHCH$_2$, NH(CH$_2$)$_2$, CH$_2$NHCH$_2$, cycloalkyl, alkyl-cycloalkyl, alkyl-cycloalkyl-alkyl, heterocyclyl (such as nitrogen-containing rings of 4 to 8 atoms), alkyl-heterocyclyl, or alkyl-heterocyclyl-alkyl, preferably piperidinyl or piperazinyl.

K2. A FRET conjugate of Formula XIVa:

Formula XIVa

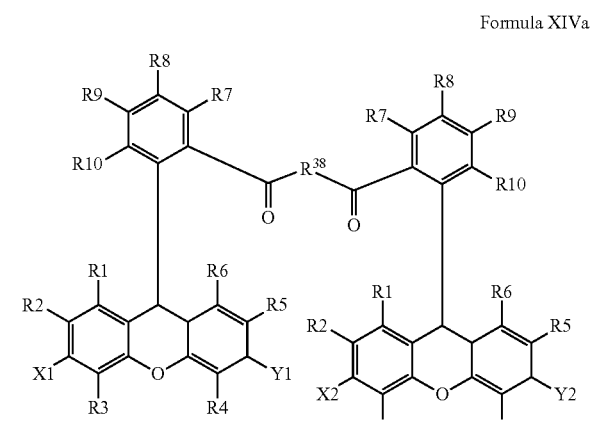

where X1 and X2 are selected from —OH, —OR$^X$ and —NR$^X$R$^{XX}$, and X1 and X2 are preferably different, where Y1 and Y2 are selected from =O or =N$^+$R$^Y$R$^{YY}$ and Y1 and Y2 are preferably different, wherein $R^1$, $R^2$, $R^3$, $R^4$, $R^5$, $R^6$, $R^7$, $R^8$, $R^9$, $R^{10}$, $R^X$, $R^{XX}$, $R^Y$, and $R^{YY}$ are independently selected from hydrogen and a substituent having less than 40 atoms, or are as defined elsewhere in the present disclosure; and where $R^{38}$ is 4- to 8-membered cycloalkyl or a 4- to 8-membered heterocyclyl (such as nitrogen-containing rings of 4 to 8 atoms), preferably piperidinyl or piperazinyl.

Preferred compounds of Formula XIVa are those where the emission of a first chromogenic moiety (e.g., a fluorescein derivative) and the absorbance of a second chromogenic moiety (e.g., a rhodamine derivative) overlap.

K3. The conjugate according to embodiment K1 or K2, wherein said conjugate comprises a first chromogenic moiety and a second chromogenic moiety, and the first chromogenic moiety is a carboxy-fluorescein, and the second chromogenic moiety is selected from rhodamine 6G and rhodamine B.

K4. The conjugate according to any of embodiments K1 to K3, where X1 is selected from —OH and —OR$^X$ and X2 is —NR$^X$R$^{XX}$, Y1 is =O, and Y2 is =N$^+$R$^Y$R$^{YY}$.

K5. The conjugate according to any of embodiments K1 to K4, wherein one or more of $R^1$ to $R^{10}$ (preferably $R^{10}$) is optionally attached to a linker (L), and the linker is optionally attached to a peroxidase substrate (PS).

K6. A method for detection of a target in a sample by fluorescent detection, comprising:
(i) incubating a sample supposedly comprising a target in an aqueous solution, wherein the target comprises peroxidase activity or the target is directly or indirectly linked to a peroxidase enzyme, wherein the aqueous solution comprises:

a FRET conjugate according to any of embodiments K2 to K5, wherein said FRET conjugate comprises a first chromogenic moiety and a second chromogenic moiety, and the first chromogenic moiety (e.g., a fluorescein derivative) has an absorbance spectrum, and the second chromogenic moiety (e.g., a rhodamine derivative) has an emission spectrum, and the light absorbance spectrum and the light emission spectrum overlap,
(ii) exciting the precipitate of the FRET conjugate;
(iii) detecting fluorescence from the emission spectrum in the sample, thereby detecting the target in the sample.
K7. The method according to embodiment K6, wherein the sample is incubated at a time and temperature sufficient to form a precipitate of the FRET conjugate.
K8. The method according to embodiment K6, wherein further comprising incubating the sample with at least two, or at least three, other fluorescent molecules. The other fluorescent molecules have a different color or absorbtion maximum than the FRET conjugate.
L1. A method for detection of a target by chromogenic detection in a sample comprising brown tissue, comprising:
(i) incubating a sample supposedly comprising a target in an aqueous solution, wherein the target comprises peroxidase activity or the target is directly or indirectly linked to a peroxidase enzyme,
wherein the aqueous solution comprises:
a) a chromogenic conjugate according to any of embodiments A1 to A19, or K1 to K5,
b) a peroxide compound,
at a time and temperature sufficient to form a colored precipitate of the chromogenic conjugate; wherein the cancerous cells are slecand
(ii) detecting the colored precipitate of the chromogenic conjugate in the sample, thereby detecting the target in the sample.
L2. The method according to embodiment L1, where the brown tissue is selected from tonsil, liver, melanoma, cells, lung cancer, or others.

EXAMPLES

Examples 1 to 26 are non-limiting demonstration of synthetic methods for conjugates and intermediates used in the making of some selected chromogenic conjugates, and their practical applications in detecting of molecular targets in IHC and ISH assay formats.

Example 1

Tert-Butyl N-[2-[2-(2-aminoethoxy)ethoxy]ethyl]carbamate (Compound 20) was prepared according to WO2007/015168.

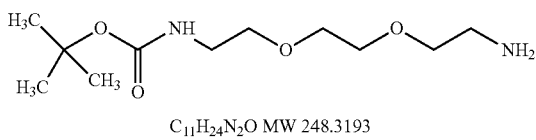

$C_{11}H_{24}N_2O$ MW 248.3193

Example 2

"Boc-L15" (compound 21) was prepared according to US20100055761.

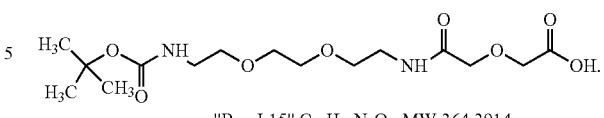

"Boc-L15" $C_{15}H_{28}N_2O_8$, MW 364.3914

Example 3

Tert-butyl-N-[2-[2-[2-[(2-bromoacetyl)amino]ethoxy]ethoxy]ethyl] carbamate (Compound 22) was prepared as follows: 214 mmol 2-bromoacetic acid anhydride in approx. 700 mL dichloromethane (DCM) was prepared by reacting 214 mmol dicyclohexylcarbodiimide (DCC) and 428 mmol bromoacetic acid in 600 mL DCM for 20 h at 4° C. and filtering off dicyclohexylurea (DCU) with DCM washes.

To 214 mmol 2-bromoacetic acid anhydride in approx. 700 mL DCM, prepared as described above, with ice cooling was added 321 mmol lutidine, then 214 mmol Compound 20 dissolved in 106 mL DCM was added drop wise with stirring over 30 min. After an additional 10 min, the ice cold reaction mixture was extracted with 400 mL, then 50 mL 1M citrate, pH 4.5 and finally 50 mL water. The DCM was evaporated off below 40° C. and two further portions of 200 mL DCM were evaporated off to give 84 g of oil to which was added 170 mL diethylether resulting in a further precipitation of DCU that was filtered off. Overnight at −18° C. produced a dense micro-crystalline off-white precipitate that was filtered off, washed with diethylether and dried in vacuum. Yield 60 g, 76% of 22. A single pure product by TLC, weakly UV active, strong ninhydrin reaction, rf. 0.5 in 5% methanol in ethyl acetate. Analysis by mass spectroscopy provided data consistent with bromine isotope pattern. The purity was >99% by HPLC@210 nm.

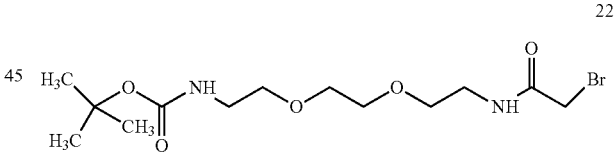

tert-butyl-N-[2-[2-[2-[( 2-bromoacetyl)amino]ethoxy]ethoxy]ethyl]carbamate, $C_{13}H_{25}BrN_2O_5$ MW 369.252

Example 4

Rhodamine 6G hydrochloride (Compound 23) was prepared as follows: 50 g Rhodamine 6G ethyl ester hydrochloride, Sigma-Aldrich catalogue #R[4127], was hydrolyzed by refluxing in 320 mL water, 30 mL 10 M sodium hydroxide and 350 mL ethanol for 45 min. The reaction mixture was cooled and acidified with 75 mL 4 M HCl to produce an intensely red precipitate that was filtered off, washed extensively with water and dried in vacuum at 90° C. over sodium hydroxide pellets. The yield was 46 g Rhodamine 6G hydrochloride, 99.3% pure by HPLC@260.

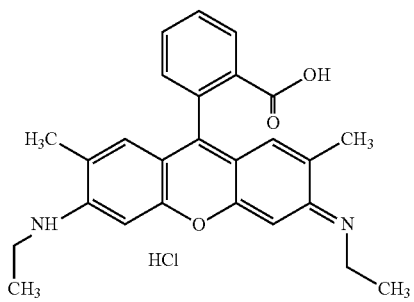

Rhodamine 6G Hydrochloride

The name "Rhodamine 6G" is the trivial and commercial name for the ethyl ester. The free acid is available as perchlorate from Sigma Aldrich under the name "Rhodamine 19". To avoid confusion with trivial, abbreviated and/or commercial names that might change with substitution pattern, this parent structure will be referred to as "Rhodamine 6G" throughout this application, disregarding trivial names for specific derivatives.

Example 5

TetraMethyl Rhodamine was prepared by sulfuric acid-catalyzed condensation of phthalic anhydride and 3-(Dimethylamino)-phenol analogous to prior art methods. Following the extractive work-up, it was further purified by chromatography with 25% methanol in DCM to give 17 g of 98% HPLC pure product@ 260 nm. Rhodamine B base #234141, Rhodamine 101 inner salt #83694 and Rhodamine 110 chloride #83695 were from Sigma-Aldrich.

Example 6

This example describes an exemplary method of synthesis of ethyl-carboxymethyl Rhodamine B Bromide (Compound 24).

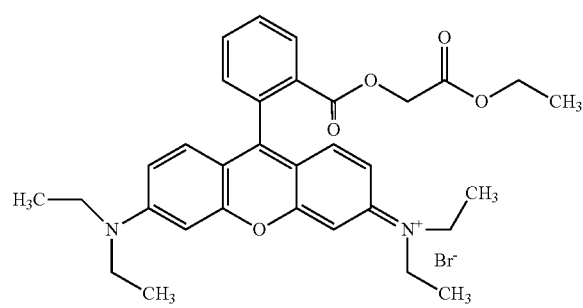

Ethyl-carboxymethyl-RhodamineB Bromide 4.42 g (10 mmol) Rhodamine B base (Sigma Aldrich) was added to a 250 mL flask with 9 mL acetonitril and 3.5 mL N,N-diisopropylethylamine (DIPEA) (20 mmol). The solution was stirred at 90° C. until all had dissolved and then 1.67 mL ethyl bromoacetate (15 mmol) was added. After further 1 hour reaction at 90° C. the reaction mixture was cooled to room temperature and 100 mL diethyl ether was added drop-wise producing a fine dark powder precipitate. It was filtered off, washed with 2×20 mL diethyl ether and dried overnight in vacuum. This gave a dark purple powder of 6.93 g (98%) with 99% HPLC purity @260 nm.

Example 7

This example describes an exemplary method of synthesis of Rhodamine B piperazine amide bromide (Compound 25).

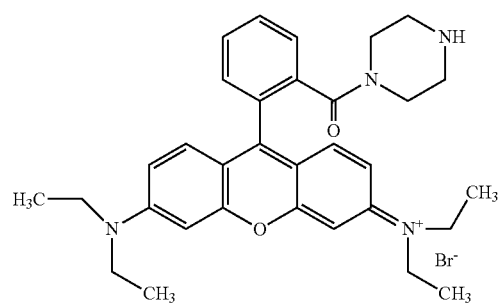

RhodamineB piperazin amide Bromide 10 g Compound 24 (16 mmol) and 10 g piperazine were dissolved in 40 mL acetonitrile and reacted with stirring at 90° C. for 1½ hour under nitrogen. Acetonitrile and excess piperazine were evaporated off at 70-80° C. on a rotary evaporator. Further two 25 mL portions of acetonitrile were added and again evaporated off to drive out remaining piperazine. Lastly the product was dissolved in 25 mL acetonitrile and 100 mL diethyl ether was added drop-wise under stirring, producing a fine dark powder. It was filtered off and dried in a desiccator with oil pump overnight to give a purple-golden solid. The yield was 7.64 g (82%) with a purity of 98% by HPLC @260 nm.

The piperazine amides of Rhodamine 6G and TetraMethylRhodamine were prepared as Compound 25, via the respective Ethyl-Carboxymethyl esters followed by reaction with piperazine.

Example 8

This example describes an exemplary method of synthesis of TetramethylRhodamine-Pip-L12-Cou (Compound 7). 100 mg TetraMethylRhodamine piperazine amide hydrobromide (see Example 7) and 100 mg Compound 22 were suspended in 1 mL NMP and 50 microL DIPEA. After 4 hours at 80° C. the reaction mixture was precipitated with diethyl ether to give the intermediate TetraMethylRhodamine-Pip-L12-Boc. This was dissolved in 1.5 mL TFA for 30 min to remove the Boc-group, precipitated with diethyl ether and reacted with COMU ((1-Cyano-2-ethoxy-2-oxo-ethylidenaminooxy)dimethylamino-morpholino-carbenium hexafluorophosphate) activated coumaric acid for 10 min, followed by HPLC purification. The yield was 73 mg (50%).

Example 9

This example describes an exemplary method of synthesis of Rhodamine 6G-Et-Pip-L12-Cou (Compound 14). 100 mg of Rhodamine 6G was reacted with 3 equivalents of N-hydroxy-succinimide, 3 equivalents diisopropyl carbodiimide and 3 equivalents of N-Boc-N'-[2-hydrdoxyethyl]-piperazine in NMP over night at 80° C. This gave the intermediate Rhodamine 6G-Et-Pip-Boc:

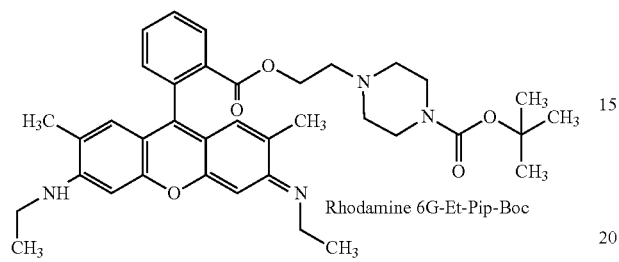

Rhodamine 6G-Et-Pip-Boc

This crude intermediate was isolated by precipitation with diethyl ether, then deprotected with TFA, precipitated with diethyl ether, alkylated with Compound 22, Boc deprotected, and finally reacted with COMU activated coumaric acid and HPLC purified. The yield was 7 mg Compound 14, approx 5% for all steps five combined.

Example 10

This example describes an exemplary method of synthesis of Rhodamine 6G-L12-Boc (Compound 26).

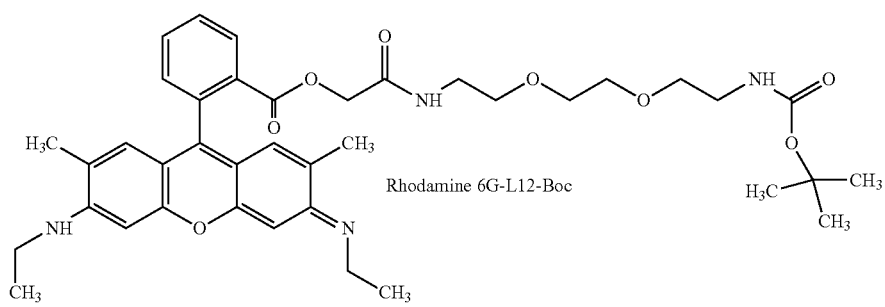

Rhodamine 6G-L12-Boc 2.07 g Rhodamine 6G inner salt and 5.0 mmol Compound 23 were dissolved in 15 mL of anhydrous NMP and 1.7 mL DIPEA and (two equiv.) at 100° C. Once all had dissolved, 2.76 g Compound 22 (1.5 equiv.) was added and the reaction mixture stirred at 100° C. for three hours. The mixture was cooled to room temperature, and with vigorous stirring 200 mL ethyl acetate was added drop-wise, precipitation commencing after approx. half the ethyl acetate had been added. The mixture was gently stirred at 4° C. over night to produce a bright red precipitate that was filtered off, washed with a little cold ethyl acetate and dried over night in vacuum. This produced 3.4 g Compound 26, with a yield of 99%, and a purity of 97% by HPLC@260 nm.

Example 11

This example describes an exemplary method of synthesis of Rhodamine 6G-L12-TFA salt (Compound 27).

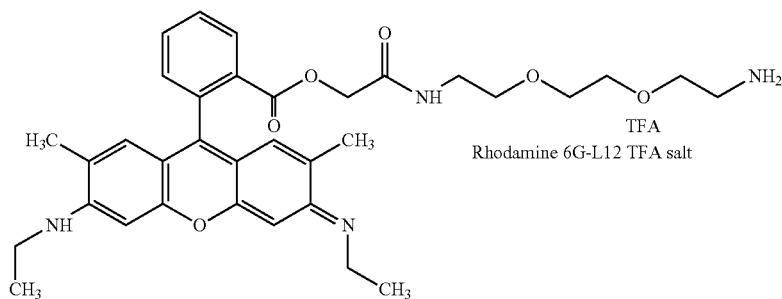

Rhodamine 6G-L12 TFA salt

27

2 g Compound 26 (Rhodamine 6G-L12-Boc) was dissolved in 12 mL TFA at room temperature. After 30 min, first 100 mL ethyl acetate and then 100 mL diethyl ether were added with ice cooling. This produced a deep red, extremely hygroscopic, precipitate that was filtered off and washed with a little diethyl ether and immediately dried in vacuum. The yield was 1.05 g (50%) with a purity of 97% by HPLC@260 nm.

Example 12

This example describes an exemplary method of synthesis of Rhodamine 6G-L12-Cou (Compound 2). 100 mg Compound 27 was dissolved in 1 mL NMP. 41 mg coumaric acid and 100 mg COMU (0.95 equiv.) were dissolved in 0.5 mL NMP and activated by 43 microL DIPEA (1 equiv.) for 30 seconds. The activated mixture was added to the solution of Compound 27, immediately followed by further 100 microliters DIPEA. The reaction was complete in 10 min and the product precipitated with 15 mL diethyl ether. It was partially dissolved in 50 mL of 2% TFA and 25% acetonitrile in water and purified by RP-HPLC. Each product-containing fraction was analyzed by mass spectroscopy and the pure fractions were pooled and freeze-dried. The yield was 40 mg (38%). Compound 2 has been tested for mutagenicity, and results indicate it does not have significant mutagenicity. Compound 2 is tested in LD50 experiments on rats and is expected to have low toxicity, especially compared to DAB.

Example 13

Compound 1 (Rhodamine 110-L12-Cou); Compound 3 (TetraRhodamine-L12-Cou); Compound 4 (RhodamineB-L12-Cou) and Compound 5 (Rhodamine 101-L12-Cou) were prepared in similar manner as Compound 2 (see Example 12), through direct alkylation of the starting rhodamine compound with Compound 22 in NMP with excess DIPEA at 100° C. for 3-4 h, followed by diethylether precipitation. The intermediates were Boc-deprotected for 30-60 min in neat TFA and precipitated as TFA salts by addition of diethyl ether. Reaction with COMU (activated coumaric acid) followed by HPLC purification gave the final chromogenic conjugates.

Example 14

In this example, other 4-hydroxy-coumaric acid derivatives of Rhodamine 6G (Compounds 16-19) were prepared in a similar manner to the method of preparing Compound 2 (Example 12) via COMU mediated coupling to the TFA salt Compound 27. Compound 16 (Rhodamine 6G-L12-Caf) was prepared from Compound 27 and COMU activated caffeic acid; Compound 17 (Rhodamine 6G-L12-2,4-OH-Cin) was prepared from Compound 27 and COMU activated 2,4-dihydroxy cinnamic acid; Compound 18 (Rhodamine 6G-L12-Fer) was prepared from Compound 27 and COMU activated ferulic acid; Compound 19 (Rhodamine 6G-L12-Sin) was prepared from Compound 27 and COMU activated sinnamic acid. In all preparations, the COMU activation of the cinnamic acid derivatives was performed in NMP with a slight excess of the free cinnamic acids and exactly one equivalent of DIPEA. As was done in the preparation of Compound 2, Compound 27 was dissolved in NMP, the activated cinnamic acids were added, and then an excess of DIPEA. This minimized side reactions on the unprotected hydroxyl groups.

Example 15

This example describes exemplary methods of synthesis of chromogenic conjugates with shortened and extended linkers. Compound 15 (Rhodamine 101-L27-Cou) were prepared by adding a coupling step with Compound 21 (Boc-L15-OH). To 70 mg, approx 0.1 mmol, of Compound 27 suspended in 0.5 mL NMP was added 0.13 mmol of Compound 21 (Boc-L15-OH) activated with 0.95 equivalents COMU and 1 equivalent DIPEA. After 10 min the intermediate Rhodamine 6G-L27-Boc was precipitated with 15 mL diethyl ether; then dissolved in neat TFA for 30 min to remove the Boc group, followed by diethyl ether precipitation and finally reaction with COMU activated coumaric acid. Compound 13 was prepared in similar manner to Compound 2, by alkylation of Rhodamine 6G with N-(2-bromoacetyl)-N'-Boc-ethylenediamine, followed by TFA mediated Boc deprotection and coupling with COMU activated coumaric acid.

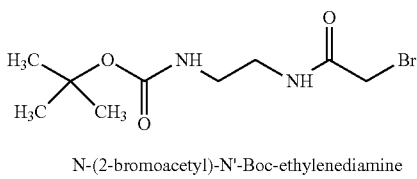

N-(2-bromoacetyl)-N'-Boc-ethylenediamine

Example 16

This example describes exemplary methods of synthesis of fluorescein-based chromogenic conjugates. Compound 9, Compound 10 and the 2,7-dichloro fluorescein-based Compound 11 were prepared in a similar manner to the preparation of the rhodamines (see Examples 12-13) through alkylation of the parent fluorescein with Compound 22.

Example 17

This example describes exemplary methods of synthesis of Compound 28 (Flu-L12-Boc). 1.66 g Fluorescein and 1.85 g Compound 22 (1 equivalent) were dissolved in 3 mL NMP and 1.3 mL DIPEA (1.5 equivalents) and stirred overnight at 100° C. The reaction mixture was taken up in 50 mL DCM and extracted twice with 5 mL saturated NaHCO$_3$ and 45 mL water. The DCM phase was reduced to an intense red oil that was purified by chromatography on 100 mL silica. The desired product, Compound 28 (Flu-L12-Boc), eluded as the last major product with 15% MeOH in DCM. The yield was 465 mg (15%). In contrast to the monoether Compound 29, Compound 28, with the same mass, retained a distinct absorption around 460 nm even under acidic condition, whereas Compound 29 collapsed into a colorless spirolactone. The two bis-alkylated products, namely the colored ether-ester Compound 30, and the substantially colorless di-ether spirolactone 31, could be characterized by mass and color.

Example 18

This example describes exemplary methods of synthesis of Compound 10 (Flu-L12-Cou). 62 mg Compound 28 (Flu-L12-Boc) was dissolved in 0.5 mL TFA at room temperature. After 30 min the deprotected intermediate Flu-L12 was isolated by precipitation with 8 mL diethylether. It was dissolved in 0.3 mL NMP and reacted with 2 equivalents COMU-activated coumaric acid in 0.4 mL NMP. After 10 minutes the crude product was precipitated with diethyl ether and HPLC purified. The yield was 40 mg (60%).

Compound 11 (2,7-Dichloro-Flu-L12-Cou) was prepared in the same manner as Compound 10, starting from 2,7-Dichloro Fluorescein and Compound 22. Isolation and characterization of the correct isomer was done by mass/UV, Boc-deprotection and coupling to coumaric acid.

Example 19

This example describes exemplary methods of synthesis of Compound 9 ((O-carboxymethyl)-Flu-L12-Cou). 310 mg Compound 28 was reacted in 1 mL NMP and 170 microL DIPEA with 111 microL tert-Butyl bromoacetate (1.5 equiv.) for 4 hours at 100° C. The reaction mixture was applied

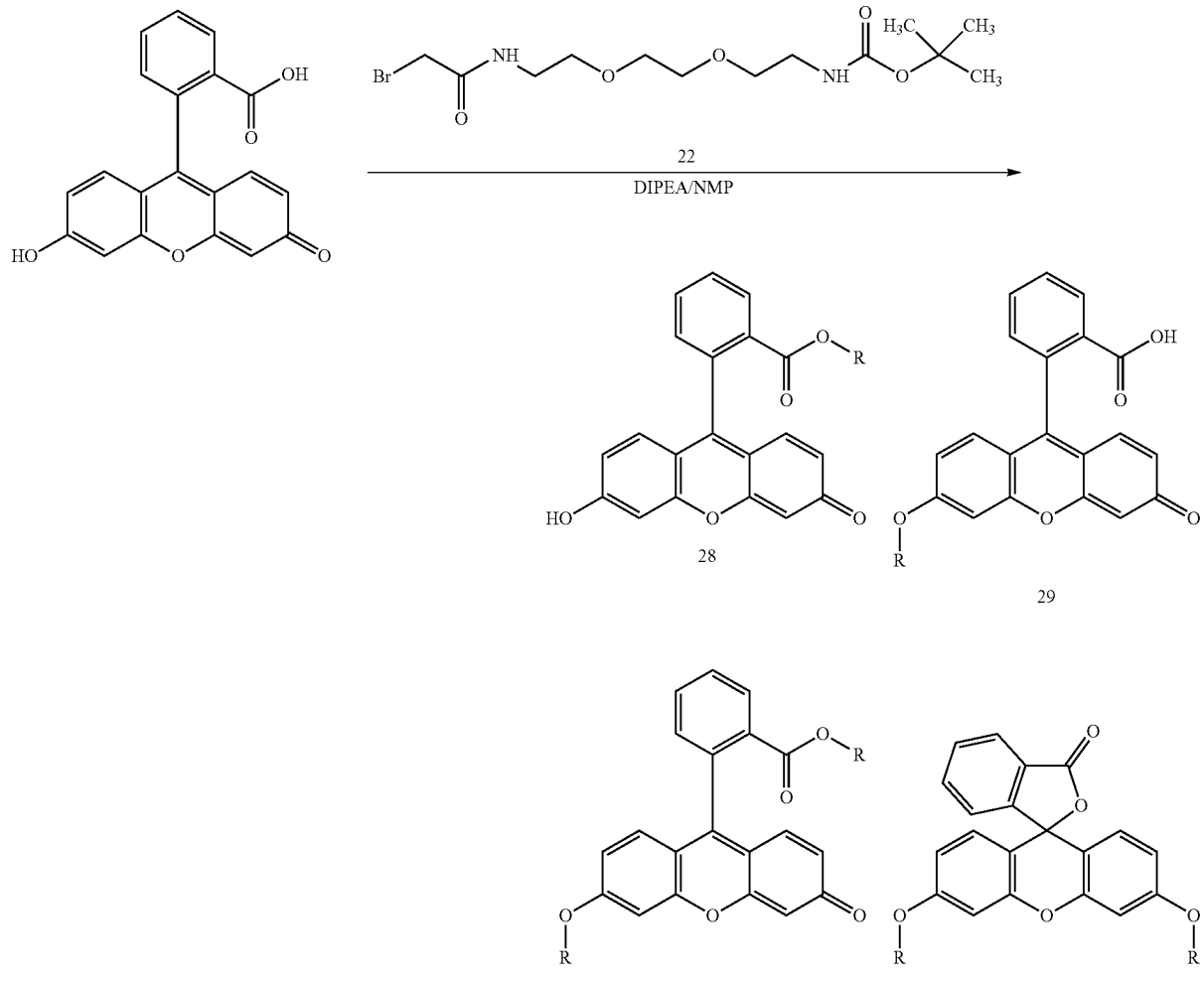

R = "L12—Boc" = CH$_2$C(O)NH(CH$_2$)$_2$O(CH$_2$)$_2$O(CH$_2$)$_2$NH—Boc directly to a small silica column, the intermediate Compound 32, (O-tert-Butylcarboxymethyl)-Flu-L12-Boc eluded with 10% MeOH in DCM. The yield was 220 mg (60%).

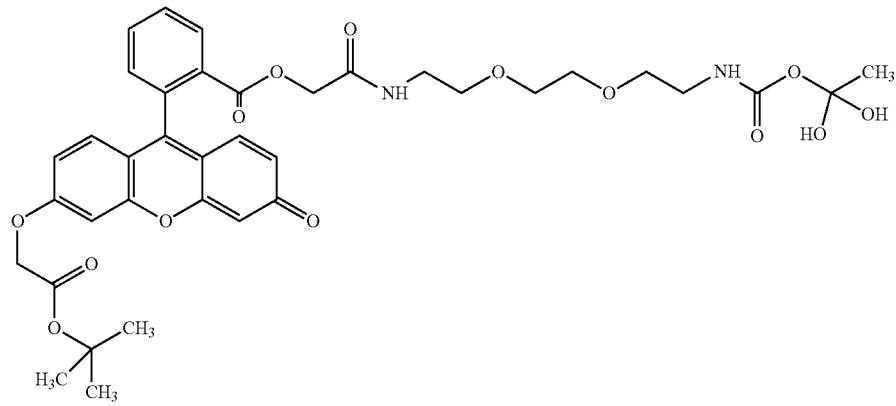

(O-tert-Butyl-carboxymethyl)-Flu-L12-Boc 73 mg Compound 32 was dissolved in 0.5 mL TFA. After 1 hour mass spectroscopy showed that the Boc group and the tert-Butyl ester had both been cleanly removed. The intermediate was precipitated with diethyl ether and reacted with COMU activated coumaric acid and HPLC purified to give 29 mg Compound 9 (40%).

Example 20

This example describes exemplary methods of synthesis of Compound 12 (Flu-Pip-L12-Cou). Fluorescein piperazin amide was prepared according to reference 3. 400 mg Fluorescein piperazine amide and 370 mg Compound 22 (1 equivalent) were dissolved in 2 mL NMP and 340 microL DIPEA and reacted for 1 hour at 60° C. Column chromatography allowed isolation of 240 mg Flu-Pip-L12-Boc (35%). 69 mg of this intermediate was Boc-deprotected with TFA and reacted with COMU activated coumaric acid, followed by HPLC purification to give 40 mg (55%) of Compound 12 (Flu-Pip-L12-Cou).

Example 21

This example describes IHC testing using many of the chromogenic conjugates described herein. The IHC testing was performed with Dako reagents and instruments and according to the manufacturer's instructions. Compounds 1-19 were initially HPLC purified to +98% purity before being assayed in these IHC tests.

As a pretreatment, multi-sample slides with FFPE human tissues, including 10 different types of normal tissues and carcinomas, and FFPE slides with Her2 control cell lines expressing 5 different levels of Her2 protein, were deparaffinized in xylene and alcohol, then target retrieved in Dako PT-Link module according to manufacturer instructions and stained on Dako Autostainer Link.

Target retrieval was also tested in microwave oven (10 minutes boiling in HEPES pH 8, target retrieval) in combination with staining on Autostainer Plus. The Autostainer stained by applying reagents to horizontally placed slides at room temperature.

Alternatively all pretreatment and staining was performed automated on-board Dako Omnis. The Omnis stains by applying reagents in a capillary gap between the slide and a lid and agitates the lid to mix reagents. This is performed at 32° C.

The samples were stained using the following protocol. Dako RTU primary antibodies (FLEX—IR series) were used according to manufacturer's instruction. For HER2 stains, a monoclonal Rabbit antiHER2 was used in 1 mg/L. To visualize the primary antibodies, Dako Envision+Dual link HRP visualization (K4061) was used, which comprises both Goat-anti-Mouse-HRP and Goat-anti-Rabbit-HRP conjugates. The stains were developed with DAB as a reference, and Compounds 1 to 19 were tested on these samples as alternatives to DAB.

An exemplary staining protocol comprised: (1) Blocking of endogenous peroxidase with Dako (52023) peroxidase block, 5 min. (2) Primary RTU antibody, 20 min. (3) Envision+Dual Link HRP, 20 min. (4) DAB (Dako K3468) or one of the present chromogenic conjugates, 5 min. (5) Counterstain with haematoxilin (Dako 53301), 5 min. Between each step, a wash was performed with a wash buffer (Dako 53006). The slides were dehydrated and cover slipped on Sakura TissueTech Film coverslipper.

It was observed that the chromogen substrate buffer usually used for DAB gave unsatisfactory results with the present chromogenic conjugates. Better results were obtained with a buffer composition comprising 50 mM imidazole:HCl pH 6.8 with 0.1% NP40-Non-idet as detergent. Extensive titration with hydrogen peroxide revealed a broad concentration range with no visible difference between 0.002% 0.003% and 0.004%.

Several different derivatives of Rhodamine 6G were prepared and tested. Comparison between Compound 2 and Compounds 16-19 with five different 4-hydroxy cinnamic acid derivatives revealed that Compound 16 with caffeic acid and Compound 19 with sinnapic acid performed poorly. Compound 18 with ferulic acid performed acceptably, Compound 17 with 2,4-dihydroxy cinnamic acid gave strong stains but also some background. Compound 2 with 4-hydroxy cinnamic acid performed the best of the five chromogenic conjugates, giving both strong and crisp stains with no background. Other chromogenic moieties were subsequently prepared with 4-hydroxy cinnamic acid as the peroxidase substrate moiety.

At 0.5 mM, Compound 2 fully matched DAB in intensity and crispness across a variety of primary antibodies staining both membranous, cytoplasmatic and nuclear markers in substantially the same pattern and with same High Expression/Low Expression balance as DAB. In stating that DAB was matched in intensity, it is with the proviso that this refers to the staining and detection of low and medium expression targets. This is what primarily determines the clinical usefulness.

Figure 2:
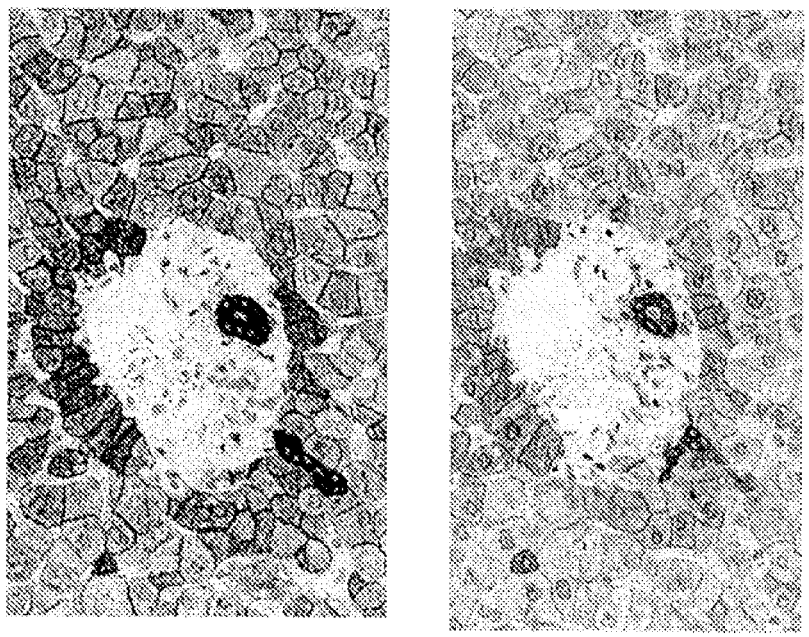
FIG. 2 is a pictomicrograph of CK-PAN stained liver tissue. The photo on the left was also stained with DAB; the photo on the right was stained with Compound 2.
Figure 3:
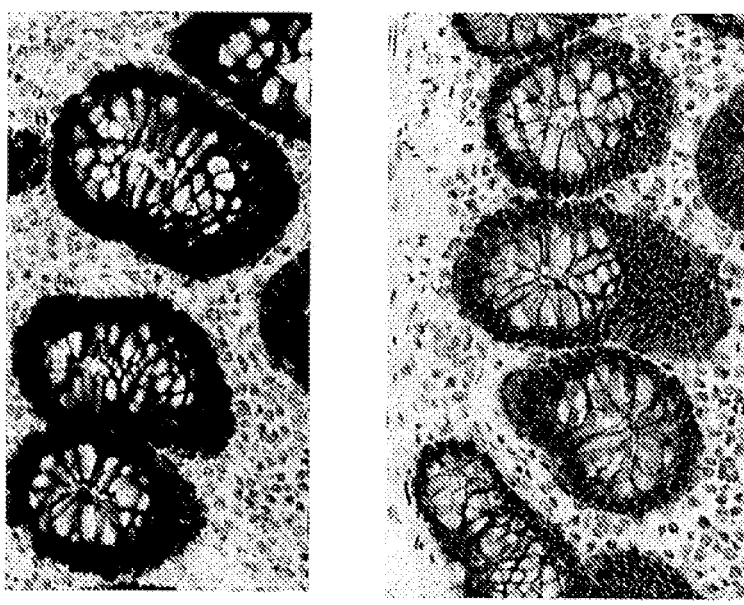
FIG. 3 is a pictomicrograph of CDX-2 stained normal colon tissue. The photo on the left was stained with DAB; the photo on the right was stained with Compound 2.

Very high expression targets in many cases appeared almost black with DAB, whereas the very present chromogenic conjugates are spectrally narrow, and still allowed passage of light at wavelengths where they do not absorb. For this reason, several trained observers including a certified pathologist, found that Compound 2 actually performed better and more dynamically in the high expression range where DAB tended to over-stain and blackout morphological details. This is reflected in the photomicrographs of FIGS. 1-3. FIG. 1 is a photomicrograph of Ki67 stained tonsil tissue. The photo on the left was stained with Compound 2 (described below); the photo on the right was stained with DAB. FIG. 2 is a pictomicrograph of CK-PAN stained liver tissue. The photo on the left was also stained with DAB; the photo on the right was stained with Compound 2. FIG. 3 is a pictomicrograph of CDX-2 stained normal colon tissue. The photo on the left was stained with DAB; the photo on the right was stained with Compound 2.

A comparison of Compound 2 to the other rhodamine 6G derivatives with different linkers between rhodamine 6G and coumaric acid showed great similarities in spectral properties. Only Compound 6 having a piperazine amide stands out by absorbing at 536 nm, around 5 nm above the esters comprising Compounds 2, 13, 14 and 15 all with abs max within 531-533 nm. Compounds 6, 14 and 15 had significantly increased solubility in the substrate buffer relative to Compound 2, whereas Compound 13 with a shortened linker, had reduced solubility. Addition of NMP to the buffer in all cases increased chromogen solubility. See result table below of the solubility of 2, 13 and 15 as function of percentage of NMP as organic co solvent, 0% representing neat aqueous buffer 50 mM imidazole:HCl, pH 6.8, 3% and 10% said percent.

TABLE 3

| Compound | Linker | 0% | 3% | 10% NMP |
|---|---|---|---|---|
| 13 | L6 | 0.5 mM | 0.9 mM | 1.8 mM |
| 2 | L12 | 1.0 mM | 1.2 mM | 3.6 mM |
| 15 | L27 | 1.7 mM | 1.9 mM | 6-7 mM |

Example 22

This example describes different colors provided by different embodiments of the present chromogenic conjugates. When tested in 0.4 to 1 mM the following chromogens worked well: Compound 2 (0.5 mM), Compound 13 (1 mM) and Compound 14 (1 mM) produced red stains that matched DAB in intensity and crispness. Compound 6 produced slightly purplish red stains that matched DAB in intensity and crispness. Compound 4 (0.4 mM) produced purple stains that matched DAB in intensity and crispness. Compound 3 (1 mM) produced slightly redish purple stains that more than matched DAB in intensity and crispness. Compound 8 (1 mM) produced slightly bluish purple stains that more than matched DAB in intensity and crispness. Compound 15 (1 mM) produced deep blue stains that more than matched DAB in intensity and crispness. Compound 9 (1 mM) produced slightly greenish yellow stains that almost matched DAB in intensity.

Example 23

This example demonstrates a method for immunohistochemical staining of three different target proteins using the present conjugates. The exemplary triple staining method employed DAB in combination with Compounds 2 and 8, on a Dako Autostainer at room temperature. The steps of the method included:
1. Blocking of endogenous peroxidase with peroxidase block (Dako S2023), 5 min.
2. antiKi67 RTU antibody (Dako IR626), 20 min
3. Envision+dual Link HRP (Dako K4061), 20 min
4. DAB (Dako K3468) 5 min.
5. HRP quenching with peroxidase block (Dako S2023) with addition of 5 mg/mL alphacyano cinnamic acid, 5 min.
6. antiCD20cy RTU antibody (Dako IR604), 20 min
7. Envision+dual Link HRP (Dako K4061), 20 min
8. 0.5 mM compound 2 in 50 mM imidazole:HCl pH 6.8, 0.003% hydrogen peroxide and 2.5% NMP, 5 min.
9. HRP quenching with peroxidase block (Dako S2023) with addition of 5 mg/mL alphacyano cinnamic acid, 5 min.
10. antiHer2 (Dako vial ST301 from HercepTest kit SK001) 20 min
11. Envision+dual Link HRP (Dako K4061), 20 min
12. 0.5 mM compound 8 in 50 mM imidazole:HCl pH 6.8, 0.003% hydrogen peroxide and 2.5% NMP, 5 min.
13. Counter stain with haematoxylin (Dako S3301)

This staining protocol produced a brown ki67 nuclear stain (DAB) with some cells stained in all tissues, a purple CD20 membrane stain (Compound 8) predominantly in tonsils and a red Her2 membrane stain (Compound 2) in mamma carcinoma and colon in combination with blue nuclei (haemotoxilin). Control experiments with single and double stains confirmed that the triple stain correctly produced the same pattern as was observed with individual stains. It was found that the addition of alphacyano cinnamic acid to the peroxidase block greatly enhanced its HRP quenching efficiency; i.e. there was no noticeable color spillover at all, the DAB was not in any way tainted by the subsequent purple and red stains, nor was the purple stain in any way tainted by the subsequent red stain. All four colors including blue haematoxilin contrasted unequivocally to each other.

The chromogenic conjugates disclosed herein contrast well to brown DAB and, with the exception of the two blue conjugates (Compound 5 and Compound 15) based on rhodamine 101, they contrast well to haematoxilin too. In combination with the possibility of very efficiently quenching HRP activity, and their narrow absorption spectra, this makes the present chromogenic conjugates disclosed herein exceptionally suited for multiplex staining and analysis.

Example 24

This example describes this use of different embodiments of the present chromogenic conjugates in Chromogen In Situ Hybridization (CISH). These chromogenic conjugates and the fact that they are HRP substrates rather than Alkaline Phosphatase substrates is shown to be especially useful for CISH applications.

Slides with multiple human tissue samples were subjected to the following fast CISH protocol:
1. Deparafination in xylene, then Ethanol
2. 10 min boiling in microwave oven.
3. Wash with buffer, water and then dehydration in Ethanol.
4. Denaturizing with IQFISHHER2 (DakoGM333, comprising FITC-labeled PNA centromer 17 probes) 10 min at 66° C.

5. Hybridization 15 min at 45° C.
6. Stringent wash 10 min at 63° C.
7. Wash buffer at room temperature.
8. Blocking of endogenous peroxidase with Dako (52023) peroxidase block, 5 min.
9. a. 20 nM antiFITC-HRP or b. 20 nM antiFITC-Alkaline Phosphatase for 20 min.
10. a. 1 mM 2 in substrate buffer pH 6.8, 0.003% hydrogen peroxide for 5 min or b. LiquidPermanentRed (Dako K0640) for 10 min.
11. Counterstain with haematoxilin (Dako 53301), 5 min.
12. Wash with water and dehydration for 1 min in absolute Ethanol.

The slides that were incubated with antiFITC-HRP in step 9 were stained with Compound 2 in step 10, and the slides incubated with antiFITC-AlkalinePhosphatase were stained with LiquidPermantRed. The stained slies are shown in FIG. 1. This protocol was not according to manufacturer's instructions, as incubation time is reduced and no proteolytic pretreatment is used.

Results: The slides stained with antiFITC-AP and LiquidPermanentRed showed small but clear and distinct dotty signals in Tonsil tissue formalin fixed for 6 hours, and very small dots in some areas of Tonsil tissue fixed for 24 hours. In no other types of tissue were signals consistently detected.

The slides stained with antiFITC-HRP and Compound 2 produced large and distinct dots in both Tonsil tissues and the expected 1-2 distinct dots in all other tissues including normal Liver, Pancreas, Renal, Colon and Cerebellum as well as in Mamma Carcinoma, Melanoma and Carcinoid. Only in one tissue, Malignant Colon Carcinoma, the dots were very small.

While the same number of nuclei is detected with Ki67, and weak liver membranes likewise are stained equally with DAB and Compound 2, the small high expression structures in liver and especially the CDX-2 Colon structures are over stained with DAB, totally covering the entire cells, while nuclei stand clearly out when stained with Compound 2.

This example illustrates the highly useful nature of the present chromogenic conjugates in conjunction with appropriate HRP conjugates in methods of analysis by CISH. As HRP is a significantly smaller enzyme (40 kDa vs. 140 kDa for Alkaline Phosphatase) it penetrates better into even deep into nuclei and, in conjunction with the intense chromogens disclosed herein, performs very well even with very short hybridization and incubation steps.

Example 25

A new chromogen was produced to further produce dichroic chromogens. This new chromogen is referred to as Compound 35 and has the following formula IX:

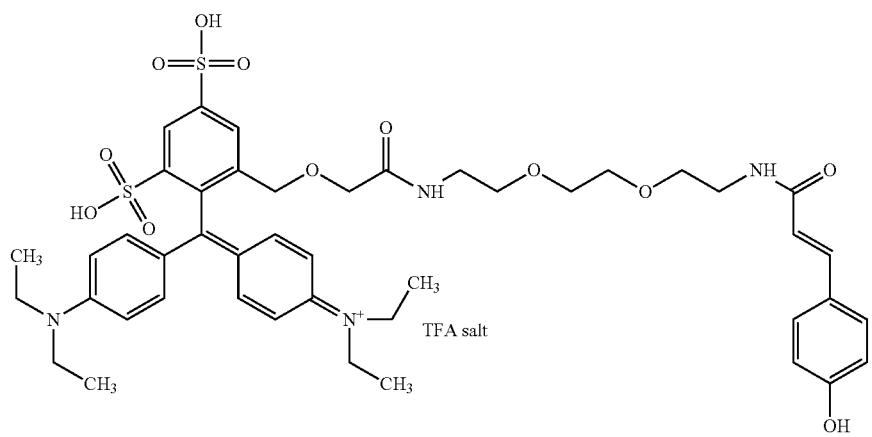

Formula IX

Compound 35 was prepared from patent Blue V sodium salt and compound 22 of the present disclosure. Patent Blue V sodium salt, 116 mg, 0.2 mmol, and Compound 22, 154 mg, 0.4 mmol, were reacted together in 1 mL NMP and 170 microL DIPEA, 1 mmol at 100° C. for 16 hours. The intermediate product was precipitated with 7 mL diethyl ether and dissolved in 1 mL TFA. After 1 hour, the intermediate was again precipitated as fine blue dust with 7 mL diethyl ether and washed several times with diethyl ether. It was dried and dissolved in 3 mL NMP with addition of 600 microL DIPEA and reacted with 600 microL 0.5 mM coumaric anhydride. After 10 minutes of reaction, the mixture was precipitated with 25 mL diethyl ether and purified by preparative HPLC as TFA salt. Yield (assuming molar coefficient of extraction of 80.000 @ 640 nm) 46 mg, 26% for the three steps. $C_{44}H_{54}N_4O_{12}S_2$ (cationic salt) calc. 896.0565 found 895.91. Compound 35 had an absorbance maximum at 640 nm in neutral water.

The following synthetic scheme illustrates making compound 35 from the intermediates of Formula X and the intermediate Compound 22:

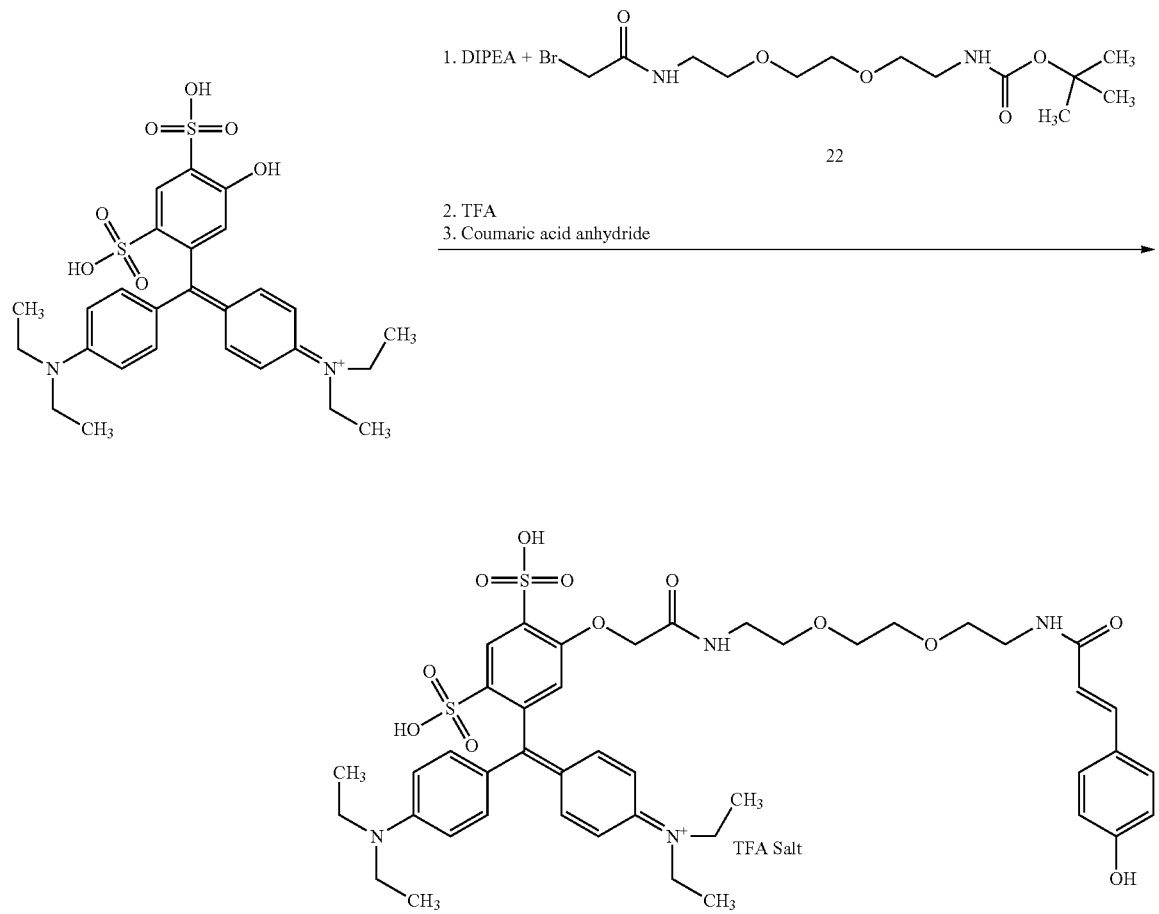

Compound 35: Cyan Chromogen, Patent Blue V-O-L12-Cou

Example 26

This example demonstrates that Compound 35 can be mixed with other chromogens, including but not limited to other chromogenic conjugates disclosed herein. These mixtures of yellow and cyan chromogens produce in-between shades of yellowish, bluish or pure balanced green. Mixtures of yellow and magenta allow preparation of in-between orange and red colors. And mixtures of magenta and cyan produce shades of increasingly bluish purple, blue and bluish cyan. Thus, Compound 35 and other cyan chromogens can be mixed with chromogens of other colors to produce stains of pure colors (rainbow colors) as well as all colors of the purple line that lie in-between red and blue.

This example also describes several examples (referred to as example dichroic orange and dichroic red) of mixing dichronic chromogens to produce chromogens that change hue with concentration are described below. In such examples, a chromogen buffer composed of: 50 mM imidazole, pH 6.8, 10% NMP, 0.1% NP40-Nonidet, 0.01% Benzalkonium chloride, 0.03% hydrogen peroxide. The examples also include example Yellow, green, blue that are also mixtures that produce desirable colors.

Example Yellow: 1 mM compound 9 mixed with 0.3 mM compound 10 produced clear bright yellow stains at low intensities and deep sunflower yellow stains at high intensities that contrasted extremely well to blue hematoxylin. The brownish hue of compound 10 at high concentrations alone was avoided, as was the unpleasing greenish yellow of compound 9 alone. Because these chromogens are so spectrally narrow, a combination of two chromogens better matches the absorbance of the broad retinal color receptors. In other words, the combination of chromogens mixed together in this ratio produced a stain and precipitate that has almost constant absorbance from 430 to 500 nm and experiences a sharp drop off at higher wavelengths.

Example Green: 1 mM compound 9 mixed with 0.3 mM compound 10+0.3 mM compound 35 (cyan) produced a beautiful bright green that at low intensities appeared somewhat faint and very bright. At higher intensities, saturation increased, resulting in a very intense yet vibrant green. The combined yellow chromogens peak at 487 nm and the cyan peaks at 642 nm. At low intensities, some blue and red light is transmitted too, but in a balanced fashion. As intensities increase and saturation of the yellow and cyan is reduced, the perceived saturation of the green is increased as less, but proportionally more green light is transmitted.

Example Blue: 1 mM compound 5 mixed with 1 mM compound 35 (cyan) produced bright yet extremely intense sky blue stains. Again, as with Example Yellow, the effect is that by mixing two closely spaced spectrally narrow chromogens, an almost perfect match with the red and green absorbing cones of the human eye is produced, leaving almost perfectly blue light. It is not the best contrast to blue hematoxylin, but the hematoxylin stained nuclei suddenly looked somewhat reddish in contrast to this blue. This is because hematoxylin has a small element of red transmission, too, which suddenly becomes apparent when contrasted to this pure blue.

Example Cyan: A perfect blue and green could be made with mixtures including Compound 35, the new cyan chromogen showing its great utility. But like greenish yellow alone, cyan alone is perceived as somewhat weak in low intensities and unpleasing to the human eye in high intensities. Even 1-2 mM of Compound 32 alone in chromogen buffer did not produce convincing results. This is understandable since both chromogens absorb at the periphery of our color vision only, allowing free transmission of most light at low intensities.

It is expressly contemplated that any chromogenic conjugates in the present disclosure can be used in any of the methods of use, compositions, and kits-of-parts in the present disclosure.

In the present disclosure, numeric ranges are inclusive of the numbers defining the range. In the present disclosure, wherever the word "comprising" is found, it is contemplated that the words "consisting essentially of" or "consisting of" may be used in its place. It should be recognized that chemical structures and formula may be elongated or enlarged for illustrative purposes.

Unless defined otherwise, all technical and scientific terms used herein have the same meaning as commonly understood by those working in the fields to which this disclosure pertain.

All patents and publications referred to herein are expressly incorporated by reference. The citation of any publication is for its disclosure prior to the filing date and should not be construed as an admission that the present claims are not entitled to antedate such publication. Further, the dates of publication provided can be different from the actual publication dates which can be independently confirmed.

In view of this disclosure it is noted that the methods and apparatus can be implemented in keeping with the present teachings. Further, the various components, materials, structures and parameters are included by way of illustration and example only and not in any limiting sense. In view of this disclosure, the present teachings can be implemented in other applications and components, materials, structures and equipment to implement these applications can be determined, while remaining within the scope of the appended claims.

We claim:

1. A composition comprising:
   (a) a mixture of at least a first chromogen and at least a second chromogen, wherein said chromogens are mixed in a ratio which produces a desired color and wherein said first chromogen comprises
     (a) a chromogenic moiety, and
     (b) a peroxidase substrate moiety,
     wherein the chromogenic moiety and the peroxidase substrate moiety are linked together via a linker to form a conjugate, wherein the conjugate is a compound of Formula I:

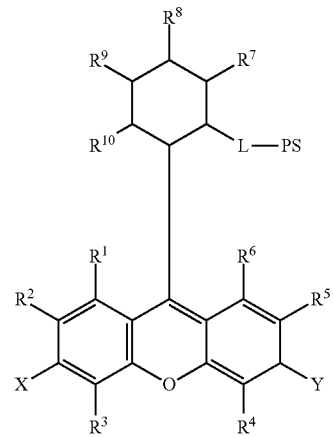

Formula I where X is —OH, —OR$^X$ or —NR$^X$R$^{XX}$,
where Y is =O, =NR$^Y$, or =N$^+$R$^Y$R$^{YY}$,
wherein R$^1$, R$^2$, R$^3$, R$^4$, R$^5$, R$^6$, R$^7$, R$^8$, R$^9$, R$^{10}$, R$^X$, R$^{XX}$, R$^Y$, and R$^{YY}$ are independently selected from hydrogen and a substituent having less than 40 atoms;
L is a linker comprising a linear chain of 5 to 29 consecutively connected atoms; and
PS is a peroxidase substrate moiety.

2. The composition of claim 1, wherein
R$^1$ is selected from hydrogen, R$^{11}$, (C1-C20) alkyl or heteroalkyl optionally substituted with one or more of the same or different R$^{14}$ groups, (C5-C20) aryl or heteroaryl optionally substituted with one or more of the same or different R$^{13}$ or suitable R$^{14}$ groups and (C6-C40) arylalkyl or heteroaryl alkyl optionally substituted with one or more of the same or different R$^{13}$ or R$^{14}$ groups, or alternatively, R$^1$ may be taken together with R$^2$ to form part of a benzo, naptho or polycyclic aryleno group which is optionally substituted with one or more of the same or different R$^{13}$ or R$^{14}$ groups;

R$^2$ is selected from hydrogen, R$^{11}$, (C1-C20) alkyl or heteroalkyl optionally substituted with one or more of the same or different R$^{14}$ groups, (C5-C20) aryl or heteroaryl optionally substituted with one or more of the same or different R$^{13}$ or R$^{14}$ groups and (C6-C40) arylalkyl or heteroaryl alkyl optionally substituted with one or more of the same or different R$^{13}$ or R$^{14}$ groups, or alternatively, R$^2$ may be taken together with R$^1$, to form part of a benzo, naptho or polycyclic aryleno group which is optionally substituted with one or more of the same or different R$^{13}$ or R$^{14}$ groups, or alternatively, when X is —NR$^X$R$^{XX}$, R$^2$ may be taken together with R$^X$ to form a 5- or 6-membered ring which is optionally substituted with one or more of the same or different R$^{13}$ or R$^{14}$ groups;

R$^X$, when present, is selected from hydrogen, (C1-C20) alkyl or heteroalkyl optionally substituted with one or more of the same or different R$^{14}$ groups, (C5-C20) aryl or heteroaryl optionally substituted with one or more of the same or different R$^{13}$ or R$^{14}$ groups and (C6-C40) arylalkyl or heteroaryl alkyl optionally substituted with one or more of the same or different R$^{13}$ or R$^{14}$ groups, or, alternatively, R$^X$ may be taken together with R$^2$ to form a 5- or 6-membered ring which is optionally substituted with one or more of the same or different $R^{13}$ or $R^{14}$ groups;

$R^{XX}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or $R^{14}$ groups and (C6-C40) arylalkyl or heteroaryl alkyl optionally substituted with one or more of the same or different $R^{13}$ or $R^{14}$ groups, or, alternatively, $R^X$ may be taken together with $R^3$ to form a 5- or 6-membered ring which is optionally substituted with one or more of the same or different $R^{13}$ or $R^{14}$ groups;

$R^3$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or $R^{14}$ groups and (C6-C40) arylalkyl or heteroaryl alkyl optionally substituted with one or more of the same or different $R^{13}$ or $R^{14}$ groups, or, alternatively, when X is $-NR^X R^{XX}$, $R^3$ may be taken together with $R^{XX}$ to form a 5- or 6-membered ring which is optionally substituted with one or more of the same or different $R^{13}$ or $R^{14}$ groups;

$R^4$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or $R^{14}$ groups and (C6-C40) arylalkyl or heteroaryl alkyl optionally substituted with one or more of the same or different $R^{13}$ or $R^{14}$ groups, or, alternatively, when Y is $-N+R^Y R^{YY}$, $R^4$ may be taken together with $R^{YY}$ to form a 5- or 6-membered ring which is optionally substituted with one or more of the same or different $R^{13}$ or $R^{14}$ groups; $R^{YY}$, when present, is selected from (C1-C20) alkyl or heteroalkyl optionally substituted with one or more of the same or different $R^{14}$ groups, (C5-C20) aryl or heteroaryl optionally substituted with one or more of the same or different $R^{13}$ or $R^{14}$ groups and (C6-C40) arylalkyl or heteroaryl alkyl optionally substituted with one or more of the same or different $R^{13}$ or $R^{14}$ groups, or, alternatively $R^{YY}$ may be taken together with $R^4$ to form a 5- or 6-membered ring which is optionally substituted with one or more of the same or different $R^{13}$ or $R^{14}$ groups;

$R^Y$, when present, is selected from hydrogen, (C1-C20) alkyl or heteroalkyl optionally substituted with one or more of the same or different $R^{14}$ groups, (C5-C20) aryl or heteroaryl optionally substituted with one or more of the same or different $R^{13}$ or $R^{14}$ groups and (C6-C40) arylalkyl or heteroaryl alkyl optionally substituted with one or more of the same or different $R^{13}$ or $R^{14}$ groups, or, alternatively, $R^Y$ may be taken together with $R^5$ to form a 5- or 6-membered ring optionally substituted with one or more of the same or different $R^{13}$ or $R^{14}$ groups;

$R^5$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or $R^{14}$ groups and (C6-C40) arylalkyl or heteroaryl alkyl optionally substituted with one or more of the same or different $R^{13}$ or $R^{14}$ groups, or, alternatively, $R^5$ may be taken together with $R^6$ to form part of a benzo, naptho or polycyclic aryleno group which is optionally substituted with one or more of the same or different $R^{13}$ or $R^{14}$ groups, or, alternatively, when Y is $-N+R^Y R^{YY}$, $R^5$ may be taken together with $R^Y$ to form a 5- or 6-membered ring optionally substituted with one or more of the same or different $R^{13}$ or $R^{14}$ groups;

$R^6$ is selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or $R^{14}$ groups and (C6-C40) arylalkyl or heteroaryl alkyl optionally substituted with one or more of the same or different $R^{13}$ or $R^{14}$ groups, or, alternatively, $R^6$ together with $R^5$ may form part of a benzo, naptho or polycyclic aryleno group which is optionally substituted with one or more of the same or different $R^{13}$ or $R^{14}$ groups;

$R^7$, $R^8$ and $R^9$ are each, independently of one another, selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or $R^{14}$ groups and (C6-C40) arylalkyl or heteroaryl alkyl optionally substituted with one or more of the same or different $R^{13}$ or $R^{14}$ groups;

$R^{10}$ is selected from selected from hydrogen, $R^{11}$, (C1-C20) alkyl or heteroalkyl optionally substituted with one or more of the same or different $R^{14}$ groups, (C5-C20) aryl or heteroaryl optionally substituted with one or more of the same or different $R^{13}$ or $R^{14}$ groups and (C6-C40) arylalkyl or heteroaryl alkyl optionally substituted with one or more of the same or different $R^{13}$ or $R^{14}$ groups, halo, haloalkyl, $-OR^{12}$, $-SR^{12}$, $-SOR^{12}$, $-SO_2R^{12}$, and nitrile;

$R^{11}$ is selected from $-NR^{15}R^{15}$, $-OR^{16}$, $-SR^{16}$, halo, haloalkyl, CN, $-NC$, $-OCN$, $-SCN$, $-NO$, $-NO_2$, $-N_3$, $-S(O) R^{16}$, $-S(O)_2R^{16}$, $-S(O)_2OR^{16}$, $-S(O)NR^{15}R^{15}$, $-S(O)_2NR^{15}R^{15}$, $-OS(O) R^{16}$, $-OS(O)_2R^{16}$, $-OS(O)_2NR^{15}R^{15}$, $-OP(O)_2R^{16}$, $-OP(O)_3R16R^{16}$, $-P(O)_3R16R^{16}$, $-C(O) R^{16}$, $-C(O) OR^{16}$, $-C(O) NR^{15}R^{15}$, $-C(NH) NR^{15}R^{15}$, $-OC(O) R^{16}$, $-OC(O) OR^{16}$, $-OC(O) NR^{15}R^{15}$ and $-OC(NH) NR^{15}R^{15}$;

$R^{12}$ is selected from (C1-C20) alkyls or heteroalkyls optionally substituted with lipophilic substituents, (C5-C20) aryls or heteroaryls optionally substituted with lipophilic substituents and (C2-C26) arylalkyl or heteroarylalkyls optionally substituted with lipophilic substituents;

$R^{13}$ is selected from hydrogen, (C1-C8) alkyl or heteroalkyl, (C5-C20) aryl or heteroaryl and (C6-C28) arylalkyl or heteroarylalkyl;

$R^{14}$ is selected from $-NR^{15}R^{15}$, $=O$, $-OR^{16}$, $=S$, $-SR^{16}$, $=NR^{16}$, $=NOR^{16}$, halo, haloalkyl, $-CN$, $-NC$, $-OCN$, $-SCN$, $-NO$, $-NO_2$, $=N_2$, $-N_3$, $-S(O) R^{16}$, $-S(O)_2R^{16}$, $-S(O)_2OR^{16}$, $-S(O)NR^{15}R^{15}$, $-S(O)_2NR^{15}R^{15}$, $-OS(O) R^{16}$, $-OS(O)_2R^{16}$, $-OS(O)_2NR^{15}R^{15}$, $-OS(O)_2OR^{16}$, $-OS(O)_2NR^{15}R^{15}$, $-C(O) R^{16}$, $-C(O) OR^{16}$, $-C(O) NR^{15}R^{15}$, $-C(NH) NR^{15}R^{15}$, $-OC(O) R^{16}$, $-OC(O) OR^{16}$, $-OC(O) NR^{15}R^{15}$ and $-OC(NH) NR^{15}R^{15}$, each $R^{15}$ is independently hydrogen or $R^{16}$, or alternatively, each $R^{15}$ is taken together with the nitrogen atom to which it is bonded to form a 5- to 8-membered saturated or unsaturated ring which may optionally include one or more of the same or different additional heteroatoms and which may optionally be substituted with one or more of the same or different $R^{13}$ or $R^{16}$ groups;

each $R^{16}$ is independently $R^{13}$ or $R^{13}$ substituted with one or more of the same or different $R^{13}$ or $R^{17}$ groups; and each $R^{17}$ is selected from —$NR^{13}R^{13}$, —$OR^{13}$, =S, —$SR^{13}$, =$NR^{13}$, =$NOR^{13}$, halo, haloalkyl, —CN, —NC, —OCN, —SCN, —NO, —$NO_2$, =$N_2$, —$N_3$, —S(O) $R^{13}$, —S(O)$_2R^{13}$, —S(O)$_2OR^{13}$, —S(O)$NR^{13}R^{13}$, —S(O)$_2NR^{13}R^{13}$, —OS(O) $R^{13}$, —OS(O)$_2R^{13}$, —OS(O)$_2NR^{13}R^{13}$, —OS(O)$_2OR^{16}$, —OS(O)$_2NR^{13}R^{13}$, —C(O) $R^{13}$, —C(O) $OR^{13}$, —C(O) $NR^{13}R^{13}$, —C(NH) $NR^{15}R^{13}$, —OC(O) $R^{13}$, —OC(O) $OR^{13}$, —OC(O) $NR^{13}R^{13}$ and —OC(NH) $NR_{13}R^{13}$.

3. The composition of claim 1, wherein the chromogenic moiety is selected from the group consisting of rhodamines and fluoresceins, and salts thereof.

4. The composition of claim 1, wherein the chromogenic moiety is selected from the group consisting of rhodamine, rhodamine 6G, tetramethylrhodamine, rhodamine B, rhodamine 101, rhodamine 110, fluorescein, and O-carboxymethyl fluorescein.

5. The composition of claim 1, wherein the chromogenic moiety is rhodamine or a rhodamine derivative.

6. The composition of claim 1, wherein the chromogenic moiety is rhodamine 6G.

7. The composition of claim 1, wherein the chromogenic conjugate is selected from the molecules shown in Table 1 and salts of the =N moieties.

8. The composition of claim 1, wherein the linker has 1-2 repeats of the following structure:

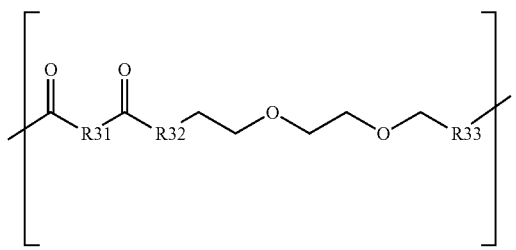

wherein $R^{31}$ is selected from $OCH_2$, $CH_2OCH_2$, alkyl-heterocyclyl, and alkyl-heterocyclyl-alkyl;

$R^{32}$ is NH;

$R^{33}$ is $CH_2NH$.

9. The composition of claim 1, wherein the peroxidase substrate moiety has the following formula:

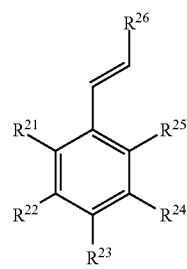

Formula II wherein $R^{21}$ is —H, $R^{22}$ is —H, —O—X, or —N(X)$_2$;

$R^{23}$ is —OH;

$R^{24}$ is —H, —O—X, or —N(X)$_2$;

$R^{25}$ is —H, —O—X, or —N(X)$_2$;

$R^{26}$ is C=O;

X is H, alkyl or aryl;

wherein the peroxidase substrate moiety is linked to the linker through $R^{26}$.

10. The composition of claim 1, wherein the peroxidase substrate is ferulic acid, cinnamic acid, caffeic acid, sinapinic acid, 2,4-dihydroxycinnamic acid or 4-hydroxycinnamic acid.

11. The composition of claim 1, wherein the peroxidase substrate is 4-hydroxycinnamic acid.

12. The composition of claim 8, wherein the linker is a compound that comprises 1 or 2 repeats of Formula IIIa, IIIb or IIIc:

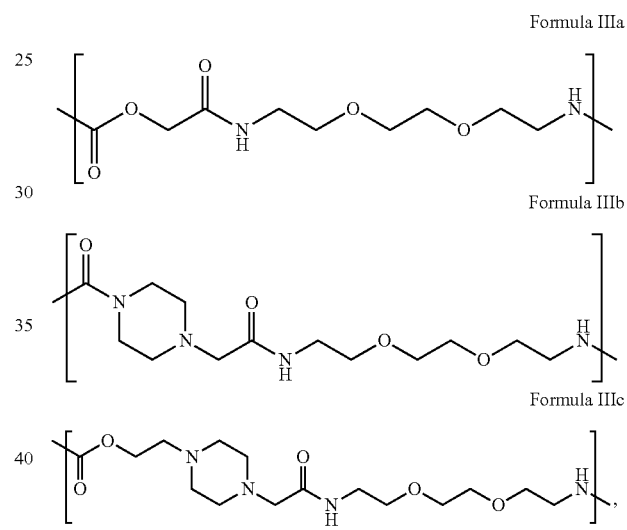

wherein the chromogenic moiety is attached to the linker at —C(O) in in Formula IIIa, IIIb or IIIc, and the peroxidase substrate moiety is attached to the linker at NH in Formula IIIa, IIIb or IIIc.

13. The composition of claim 9, wherein the linker is a compound that comprises Formula IIIa:

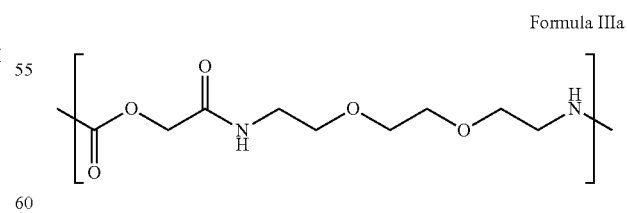

Formula IIIa wherein the chromogenic moiety is attached to the linker at the —C(O) at the left end of Formula IIIa, and the peroxidase substrate moiety is attached to the linker at the NH at the right end in Formula IIIa.

14. The composition of claim 13, wherein the chromogenic conjugate is selected from the group consisting of:

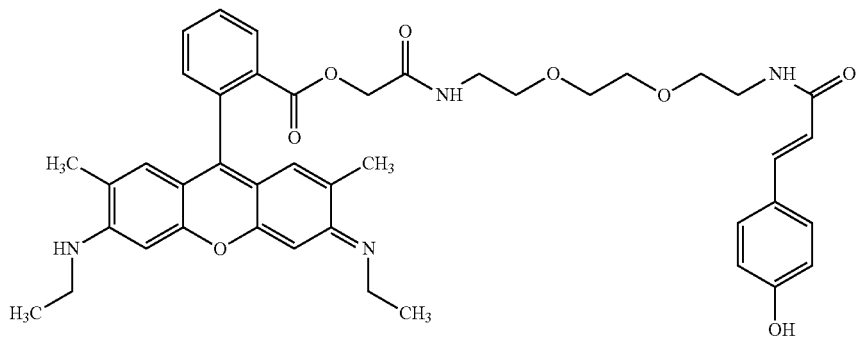 [SMILES: CC/N=c1\cc2oc3cc(NCC)c(C)cc3c(-c3ccccc3C(=O)OCC(=O)NCCOCCOCCNC(=O)/C=C/c3ccc(O)cc3)c-2cc1C]

and salts thereof.

15. The composition of claim 13, wherein the chromogenic conjugate is

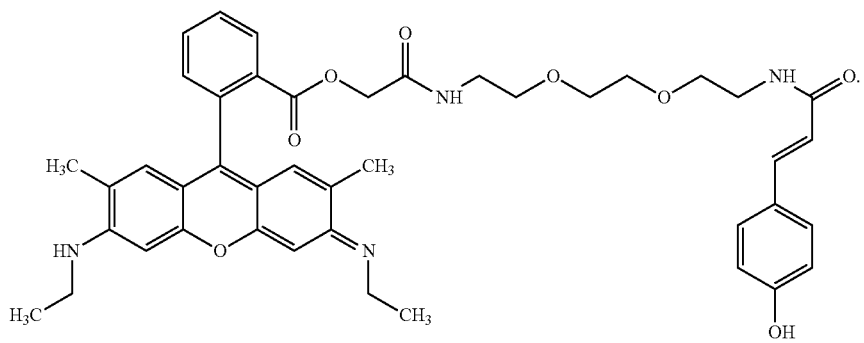 [SMILES: CC/N=c1\cc2oc3cc(NCC)c(C)cc3c(-c3ccccc3C(=O)OCC(=O)NCCOCCOCCNC(=O)/C=C/c3ccc(O)cc3)c-2cc1C]

16. The composition of claim 1, further comprising a solvent, and optionally one or more of (i) an organic modifier; (ii) an enzyme enhancer; (iii) an iron chelator; (iv) a detergent; (v) an anti-microbial agent; (vi) organic or inorganic salt; or (vii) an enzyme substrate.

17. A kit for detection of a target having peroxidase activity or linked to a peroxidase enzyme, in a sample, the kit comprising a composition according to claim 1.

18. A method for detection of a target in a sample by chromogenic detection, comprising:
incubating a sample supposedly comprising a target in an aqueous solution, wherein the target comprises peroxidase activity or the target is directly or indirectly linked to a peroxidase enzyme, wherein the aqueous solution comprises:
a) a composition according to claim 1; and
b) a peroxide compound, at a time and temperature sufficient to form a colored precipitate of the chromogenic conjugate;
detecting the colored precipitate of the chromogenic conjugate in the sample, thereby detecting the target in the sample.

19. A method of detecting two or more targets, comprising:
providing peroxidase activity at a first target in a sample;
contacting the sample with a composition according to claim 1 to form a first colored precipitate at the first target;
removing the peroxidase activity from the first target;
removing non-precipitated chromogens from the sample;
providing peroxidase activity at a second target in the sample;
contacting the sample with a second chromogenic conjugate;
forming a second colored precipitate at the second target; and
detecting the first colored precipitate and the second colored precipitate, thereby detecting the first and second targets in the sample,
wherein at least one of the first and second chromogenic conjugates is a conjugate according to claim 1, and wherein the first chromogenic conjugate molecule and the second chromogenic conjugate have one or more spectral characteristics that are different from each other.

20. The method of claim 19, wherein the method further comprises: removing the peroxidase activity from the second target; removing non-precipitated second chromogenic conjugate from the sample; providing peroxidase activity at a third target in the sample; contacting the sample with a third chromogenic conjugate having one or more spectral characteristics that are different from those of the first and second chromogenic conjugates.

21. The composition of claim 16, wherein the enzyme substrate comprises 3,3'-diaminobenzidine (DAB).

* * * * *